(12) United States Patent
Ueda et al.

(10) Patent No.: US 12,178,431 B2
(45) Date of Patent: Dec. 31, 2024

(54) INSTRUMENT ROLL CONTROL

(71) Applicant: Auris Health, Inc., Redwood City, CA (US)

(72) Inventors: Akira Bryan Ueda, San Francisco, CA (US); Adrian Tyler Hairrell, San Francisco, CA (US); Andre J. Castillo, Redwood City, CA (US)

(73) Assignee: Auris Health, Inc., Santa Clara, CA (US)

( * ) Notice: Subject to any disclaimer, the term of this patent is extended or adjusted under 35 U.S.C. 154(b) by 21 days.

(21) Appl. No.: 18/073,919

(22) Filed: Dec. 2, 2022

(65) Prior Publication Data

US 2023/0135444 A1 May 4, 2023

Related U.S. Application Data

(63) Continuation of application No. PCT/IB2022/051376, filed on Feb. 16, 2022.
(Continued)

(51) Int. Cl.
*A61B 17/00* (2006.01)
*A61B 17/072* (2006.01)

(52) U.S. Cl.
CPC ........... *A61B 17/07207* (2013.01); *A61B 2017/00398* (2013.01); *A61B 2017/07271* (2013.01)

(58) Field of Classification Search
CPC .... A61B 17/07207; A61B 2017/00398; A61B 2017/07271; A61B 1/00066; A61B 1/0052; A61B 1/00149; A61B 1/0016; A61B 1/012; A61B 1/2676; A61B 1/00043; A61B 1/05; A61B 1/0676; A61B 1/0684;
(Continued)

(56) References Cited

U.S. PATENT DOCUMENTS 3,212,590 A * 10/1965 Boyd ................. B25B 21/02
  81/464
3,859,821 A * 1/1975 Wallace ............... F16D 3/76
  464/89
(Continued)

FOREIGN PATENT DOCUMENTS

EP  2901960 A1  8/2015
JP  2016120277 A  7/2016
(Continued)

OTHER PUBLICATIONS

International Search Report for Appl. No. PCT/IB2022/051376, dated Jul. 22, 2022, 6 pages.
(Continued)

*Primary Examiner* — Robert F Long
(74) *Attorney, Agent, or Firm* — Vorys, Sater, Seymour and Pease LLP

(57) ABSTRACT

A medical instrument includes an elongate shaft defining a roll axis and a handle coupled to the elongate shaft. The handle includes a robotic drive input operable to rotate the elongate shaft with respect to the handle about the roll axis and a lockout mechanism movable between an engaged position in which the lockout mechanism impedes rotation of the elongate shaft with respect to the handle about the roll axis, and a disengaged position in which the lockout mechanism permits rotation of the elongate shaft with respect to the handle about the roll axis.

19 Claims, 23 Drawing Sheets

Related U.S. Application Data

(60) Provisional application No. 63/150,318, filed on Feb. 17, 2021.

(58) Field of Classification Search
CPC ............... A61B 1/07; A61B 2034/301; A61B 2034/303; A61B 90/98; A61B 2017/00207; A61B 2034/2051; A61B 2090/306; A61B 1/307; A61B 2017/2212; A61B 2090/309; A61B 17/221; A61B 34/30
USPC ........................................ 227/175.1–182.1
See application file for complete search history.

(56) References Cited

U.S. PATENT DOCUMENTS

| | | | | |
|---|---|---|---|---|
| 3,873,863 | A * | 3/1975 | Pew | H02K 7/145 |
| | | | | 310/90 |
| 4,179,632 | A * | 12/1979 | Harvell | H02K 7/145 |
| | | | | 403/324 |
| 4,207,898 | A * | 6/1980 | Becht | A61B 17/115 |
| | | | | 227/76 |
| 4,651,591 | A * | 3/1987 | Wurst | B25J 9/08 |
| | | | | 475/9 |
| 5,765,652 | A * | 6/1998 | Mathis | B25F 5/001 |
| | | | | 173/217 |
| 6,312,322 | B1 * | 11/2001 | Chang | B24B 23/03 |
| | | | | 451/344 |
| 6,389,921 | B1 * | 5/2002 | Nada | B25J 19/0029 |
| | | | | 901/29 |
| 10,368,954 | B2 | 8/2019 | Brisson et al. | |
| 10,603,126 | B2 | 3/2020 | Karguth et al. | |
| 10,617,420 | B2 * | 4/2020 | Shelton, IV | A61B 34/30 |
| 2003/0188861 | A1 * | 10/2003 | Doyle | E21B 23/01 |
| | | | | 166/241.1 |
| 2007/0175957 | A1 * | 8/2007 | Shelton, IV | A61B 34/76 |
| | | | | 227/178.1 |
| 2009/0108048 | A1 * | 4/2009 | Zemlok | A61B 17/105 |
| | | | | 227/176.1 |
| 2009/0206128 | A1 * | 8/2009 | Hueil | A61B 17/07207 |
| | | | | 227/176.1 |
| 2011/0290854 | A1 * | 12/2011 | Timm | A61B 17/0684 |
| | | | | 227/178.1 |
| 2011/0290855 | A1 * | 12/2011 | Moore | A61B 34/30 |
| | | | | 227/176.1 |
| 2013/0023868 | A1 * | 1/2013 | Worrell | A61B 17/07207 |
| | | | | 606/205 |
| 2013/0081838 | A1 * | 4/2013 | Tully | B25B 23/1453 |
| | | | | 173/168 |
| 2013/0098966 | A1 * | 4/2013 | Kostrzewski | A61B 17/07207 |
| | | | | 606/1 |
| 2013/0296886 | A1 * | 11/2013 | Green | A61B 34/70 |
| | | | | 606/130 |
| 2014/0257333 | A1 | 9/2014 | Blumenkranz | |
| 2014/0263569 | A1 * | 9/2014 | Williams | A61B 17/105 |
| | | | | 227/180.1 |
| 2014/0276723 | A1 | 9/2014 | Parihar et al. | |
| 2014/0305992 | A1 * | 10/2014 | Kimsey | A61B 17/282 |
| | | | | 227/176.1 |
| 2015/0075830 | A1 * | 3/2015 | Zhang | B24B 23/022 |
| | | | | 173/213 |
| 2015/0080924 | A1 * | 3/2015 | Stulen | A61B 17/320092 |
| | | | | 606/169 |
| 2016/0016320 | A1 * | 1/2016 | Rothfuss | A61B 34/30 |
| | | | | 74/490.06 |
| 2016/0033540 | A1 * | 2/2016 | Drynkin | G01N 35/0099 |
| | | | | 901/2 |
| 2016/0338667 | A1 * | 11/2016 | Noonan | A61B 8/467 |
| 2016/0338787 | A1 * | 11/2016 | Popovic | A61B 1/00042 |
| 2016/0374672 | A1 * | 12/2016 | Bear | H02J 7/00 |
| | | | | 606/219 |
| 2018/0168644 | A1 * | 6/2018 | Shelton, IV | A61B 90/03 |
| 2018/0333155 | A1 * | 11/2018 | Hall | A61B 90/90 |
| 2019/0038279 | A1 * | 2/2019 | Shelton, IV | A61B 17/068 |
| 2019/0125468 | A1 * | 5/2019 | Adams | A61B 34/30 |
| 2019/0183594 | A1 * | 6/2019 | Shelton, IV | A61B 34/71 |
| 2019/0231451 | A1 | 8/2019 | Lambrecht et al. | |
| 2020/0060516 | A1 | 2/2020 | Baez, Jr. | |
| 2020/0138529 | A1 * | 5/2020 | Ragosta | A61B 90/00 |
| 2020/0405407 | A1 * | 12/2020 | Shelton, IV | A61B 34/37 |
| 2021/0145522 | A1 * | 5/2021 | DeBuys | A61M 25/0136 |
| 2021/0197363 | A1 * | 7/2021 | Zimmer | B25J 15/04 |
| 2021/0393348 | A1 * | 12/2021 | Beckman | B25J 5/02 |
| 2022/0167973 | A1 * | 6/2022 | Shelton, IV | A61B 17/072 |
| 2022/0202517 | A1 * | 6/2022 | Overmyer | A61B 34/30 |
| 2022/0226048 | A1 * | 7/2022 | Beckman | A61B 17/07207 |
| 2022/0226051 | A1 * | 7/2022 | Johnson | A61B 17/29 |
| 2022/0249182 | A1 * | 8/2022 | Definis | A61B 17/128 |
| 2022/0304549 | A1 * | 9/2022 | Iijima | A61B 1/00114 |
| 2023/0119621 | A1 * | 4/2023 | Mancuso | B23B 31/1071 |
| | | | | 166/377 |
| 2023/0302620 | A1 * | 9/2023 | Dubnicka | B25F 5/001 |

FOREIGN PATENT DOCUMENTS

| | | |
|---|---|---|
| KR | 1020090128633 A | 12/2009 |
| WO | 2014143502 A1 | 9/2014 |

OTHER PUBLICATIONS

Written Opinion for Appl. No. PCT/IB2022/051376, dated Jul. 22, 2022, 9 pages.

International Preliminary Report on Patentability for Appl. No. PCT/IB2022/051376, dated Aug. 22, 2023, 10 pages.

* cited by examiner

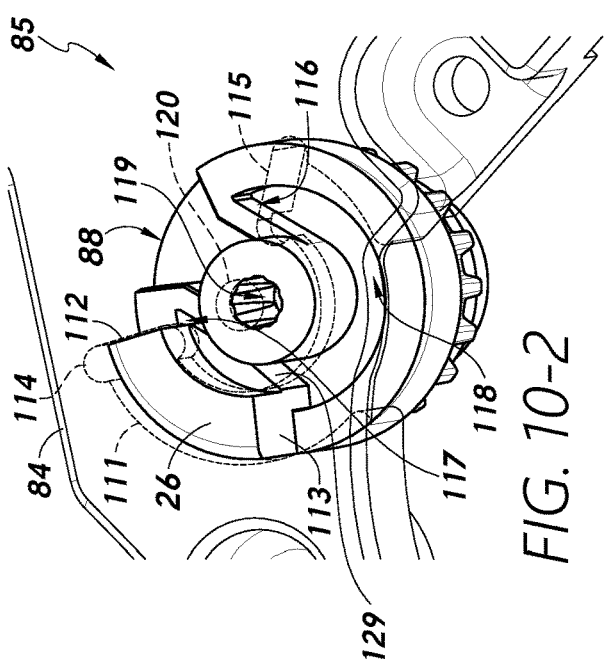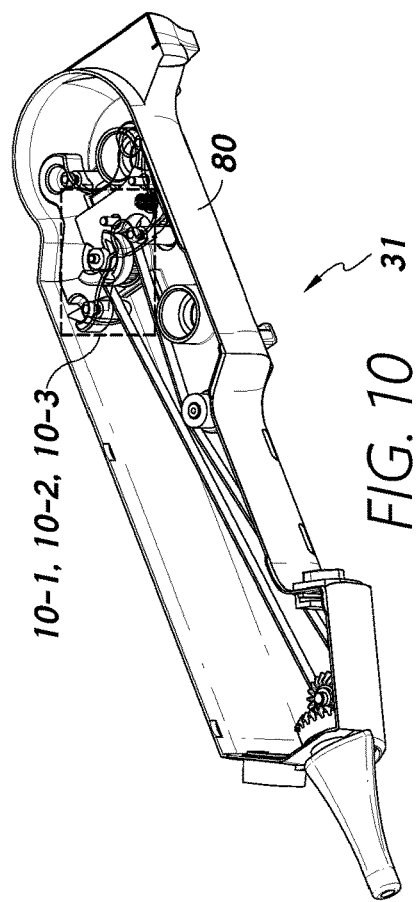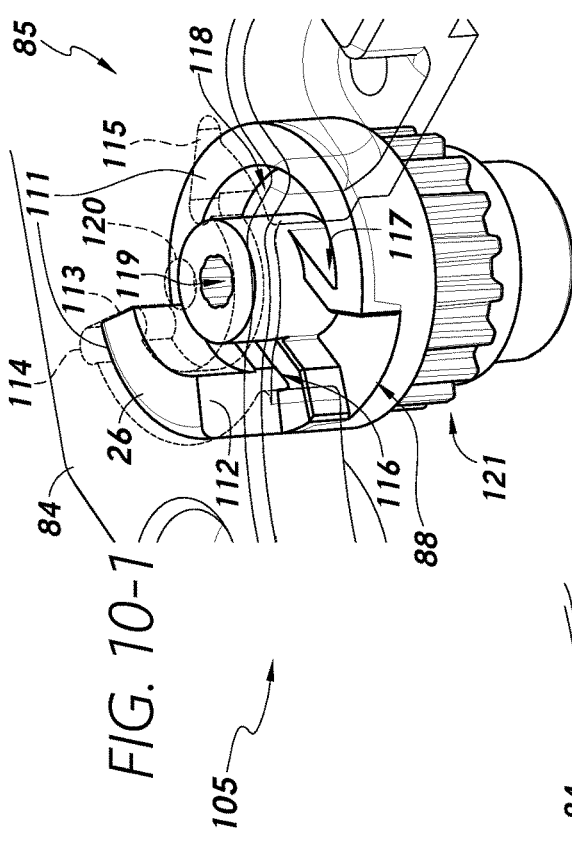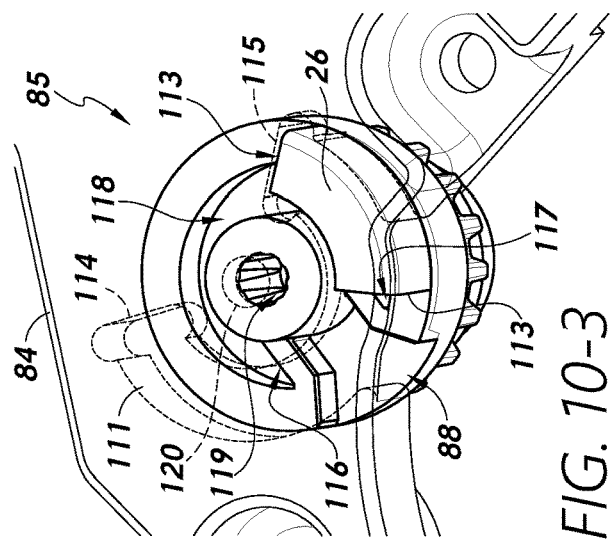

MANUAL AND ROBOTIC SHAFT ROTATION 1500
```
┌─────────────────────────┐
│ MANUALLY ROTATE SHAFT   │ 1502
│ RELATIVE TO HANDLE TO   │
│ HOME/LOCKING POSITION   │
└─────────────────────────┘
            │
            ▼
┌─────────────────────────┐
│ MANUALLY ROLL SHAFT BY  │ 1504
│    ROTATING HANDLE      │
└─────────────────────────┘
            │
            ▼
        ( FIG. 15-2 )
```
FIG. 15-1
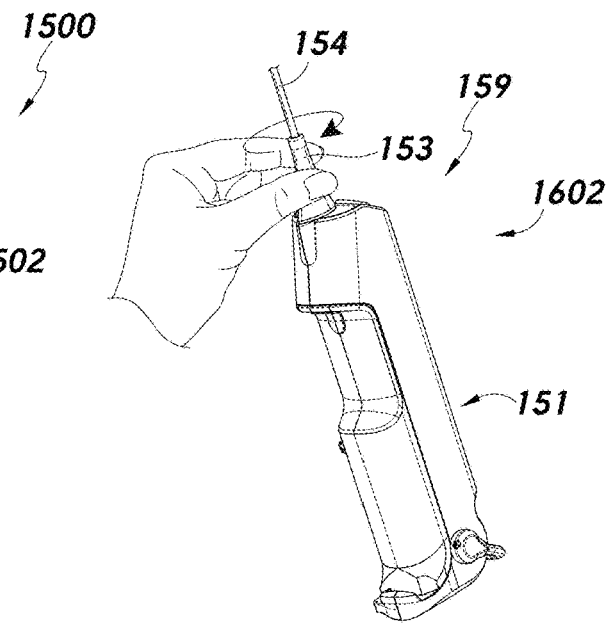
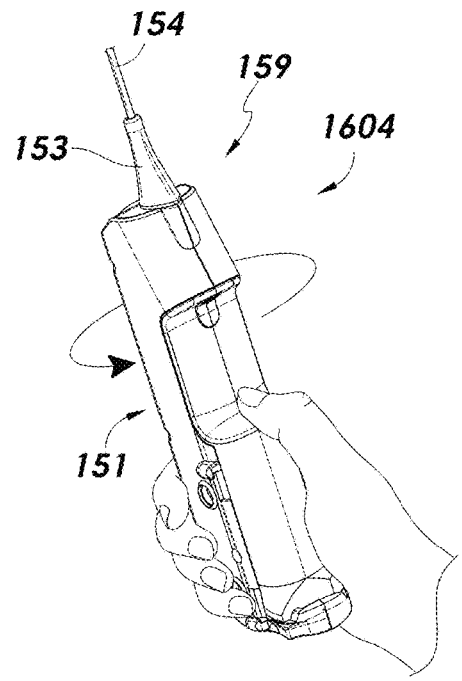
FIG. 16-1

MANUAL AND ROBOTIC SHAFT ROTATION 1500
FIG. 15-1
↓
DOCK HANDLE ON ROBOTIC END EFFECTOR / ADAPTER — 1506
↓
UNLOCK ROLL AXLE IN HANDLE — 1508
↓
ROBOTICALLY ROLL SHAFT — 1510
↓
RETURN SHAFT TO HOME ROLL POSITION — 1512
↓
FIG. 15-3
FIG. 15-2
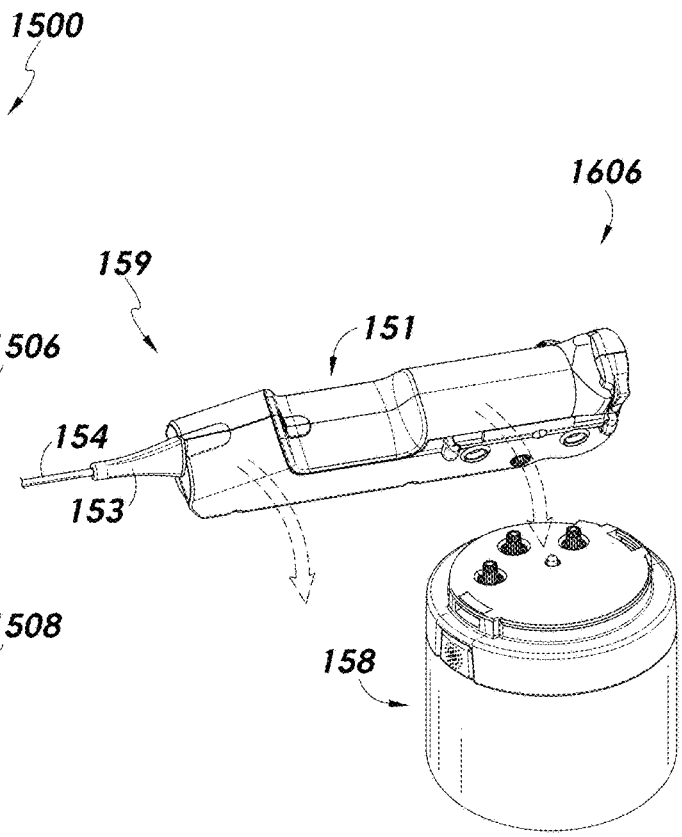
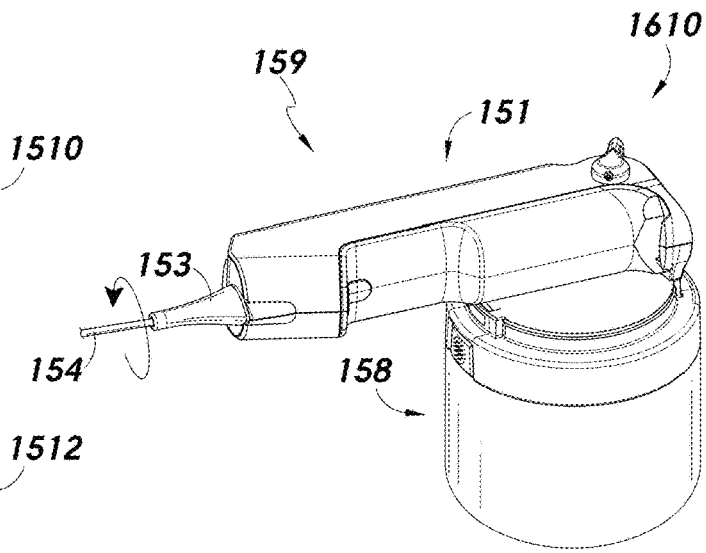
FIG. 16-2

MANUAL AND ROBOTIC SHAFT ROTATION

1500

↓
UNLATCH HANDLE TO LOCK SHAFT ROLL — 1514

INSTRUMENT ROLL CONTROL

RELATED APPLICATION(S)

This application is a continuation of International Patent Application No. PCT/IB2022/051376, filed Feb. 16, 2022, entitled INSTRUMENT ROLL CONTROL, which claims priority to U.S. Provisional Application No. 63/150,318, filed Feb. 17, 2021, entitled INSTRUMENT ROLL CONTROL, the disclosures of which are hereby incorporated by reference in their entirety.

BACKGROUND

Certain robotic medical procedures can involve the use of shaft-type instruments, such as endoscopes, which may be inserted into a patient through an orifice (e.g., a natural orifice) and advanced to a target anatomical site. Such medical instruments can be manually rotatable, such that the shaft of the instrument rolls about an axis thereof.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIGS. 4-1 and 4-2 illustrate medical system components that may be implemented in any of the medical systems of FIGS. 1-3 in accordance with one or more embodiments.

FIGS. 10, 10-1, 10-2, and 10-3 show perspective views of a roll axle assembly in accordance with one or more embodiments.

FIG. 10-4 shows an exploded view of the roll axle assembly shown in FIGS. 10-1, 10-2, and 10-3 according to one or more embodiments.

FIGS. 13-1 and 13-2 show perspective views of certain instrument handle components including an axle catch in accordance with one or more embodiments.

FIGS. 14-1 and 14-2 show a roll-lock feature for an instrument in unlocked and locked configurations/states, respectively, in accordance with one or more embodiments.

FIGS. 15-1, 15-2, and 15-3 provide a flow diagram for a process for rolling an instrument shaft in accordance with one or more embodiments.

FIGS. 16-1, 16-2, and 16-3 show certain images corresponding to various blocks, states, and/or operations associated with the process of FIGS. 15-1, 15-2, and 15-3, respectively, in accordance with one or more embodiments.

DETAILED DESCRIPTION

Figure 1:
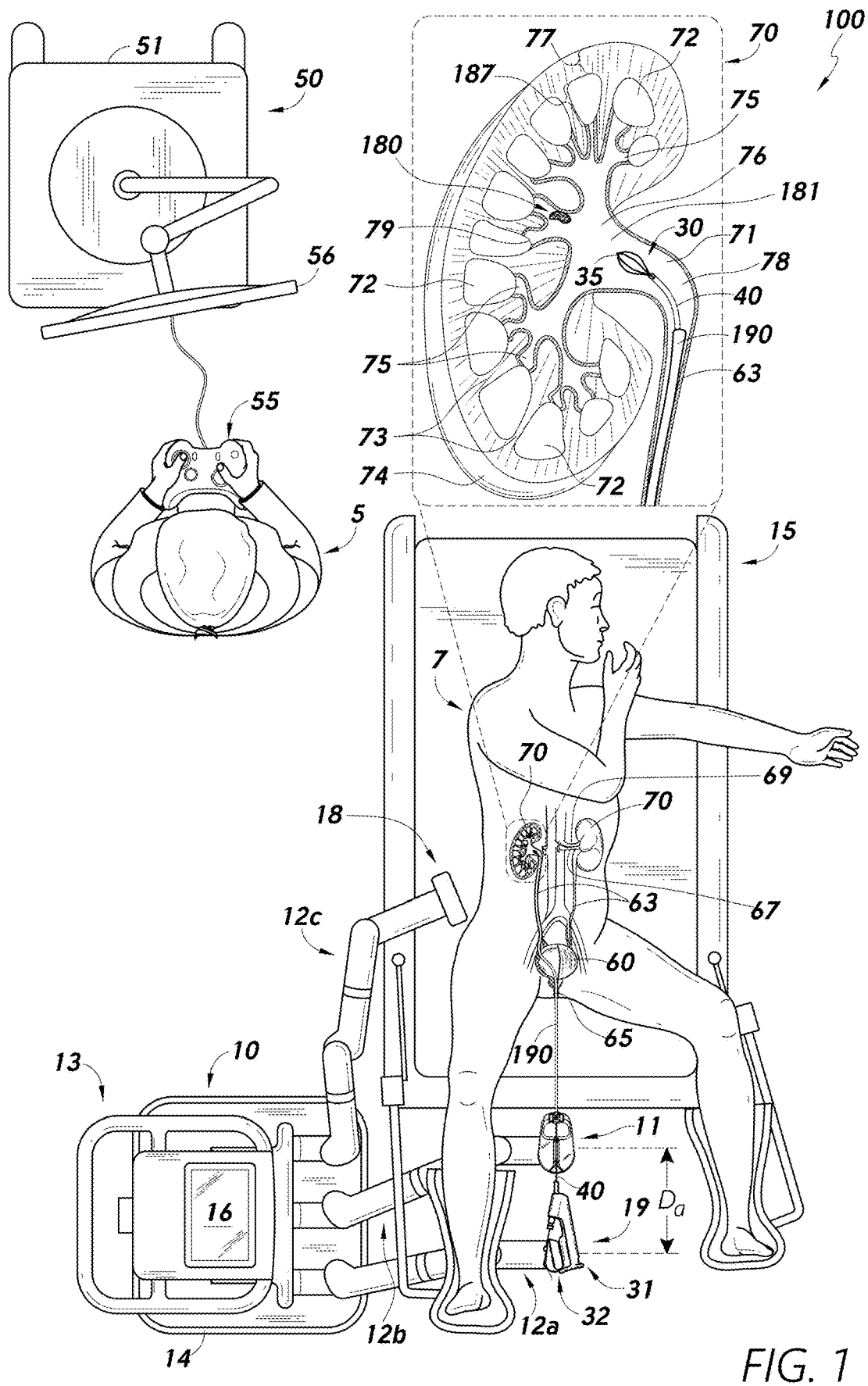
FIG. 1 illustrates an embodiment of a robotic medical system including a shaft-type instrument coupled to a robotic end effector in accordance with one or more embodiments.

The headings provided herein are for convenience only and do not necessarily affect the scope or meaning of the claimed invention. Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Although certain spatially relative terms, such as "outer," "inner," "upper," "lower," "below," "above," "vertical," "horizontal," "top," "bottom," "lateral," and similar terms, are used herein to describe a spatial relationship of one device/element or anatomical structure to another device/element or anatomical structure, it is understood that these terms are used herein for ease of description to describe the positional relationship between element(s)/structures(s), such as with respect to the illustrated orientations of the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa. It should be understood that spatially relative terms, including those listed above, may be understood relative to a respective illustrated orientation of a referenced figure.

Certain reference numbers are re-used across different figures of the figure set of the present disclosure as a matter of convenience for devices, components, systems, features, and/or modules having features that may be similar in one or more respects. However, with respect to any of the embodiments disclosed herein, re-use of common reference numbers in the drawings does not necessarily indicate that such features, devices, components, or modules are identical or similar. Rather, one having ordinary skill in the art may be informed by context with respect to the degree to which usage of common reference numbers can imply similarity between referenced subject matter. Use of a particular reference number in the context of the description of a particular figure can be understood to relate to the identified device, component, aspect, feature, module, or system in that particular figure, and not necessarily to any devices, components, aspects, features, modules, or systems identified by the same reference number in another figure. Furthermore, aspects of separate figures identified with common reference numbers can be interpreted to share characteristics or to be entirely independent of one another. In some contexts features associated with separate figures that are identified by common reference numbers are not related and/or similar with respect to at least certain aspects.

The present disclosure provide systems, devices, and methods for implementing and controlling roll of an instrument shaft, such as a medical endoscope. With respect to medical instruments described in the present disclosure, the term "instrument" is used according to its broad and ordinary meaning and may refer to any type of tool, device, assembly, system, subsystem, apparatus, component, or the like. In some contexts herein, the term "device" may be used substantially interchangeably with the term "instrument." Furthermore, the term "shaft" is used herein according to its broad and ordinary meaning and may refer to any type of elongate cylinder, tube, scope (e.g., endoscope), prism (e.g., rectangular, oval, elliptical, or oblong prism), wire, or similar, regardless of cross-sectional shape. It should be understood that any reference herein to a "shaft" or "instrument shaft" can be understood to possibly refer to an endoscope.

Medical Procedures

Although certain aspects of the present disclosure are described in detail herein in the context of renal, urological, and/or nephrological procedures, such as kidney stone removal/treatment procedures, it should be understood that such context is provided for convenience and clarity, and robotic and manual instrument shaft roll concepts disclosed herein are applicable to any suitable medical procedures, such as robotic bronchoscopy. However, as mentioned, description of the renal/urinary anatomy and associated medical issues and procedures is presented below to aid in the description of the inventive concepts disclosed herein.

In certain medical procedures, such as ureteroscopy procedures, elongate medical instruments that access the treatment site through an access sheath may be utilized to remove debris, such as kidney stones and stone fragments or other refuse or contaminant(s), from the treatment site. Kidney stone disease, also known as urolithiasis, is a medical condition that involves the formation in the urinary tract of a solid piece of material, referred to as "kidney stones," "urinary stones," "renal calculi," "renal lithiasis," or "nephrolithiasis." Urinary stones may be formed and/or found in the kidneys, the ureters, and the bladder (referred to as "bladder stones"). Such urinary stones can form as a result of mineral concentration in urinary fluid and can cause significant abdominal pain once such stones reach a size sufficient to impede urine flow through the ureter or urethra. Urinary stones may be formed from calcium, magnesium, ammonia, uric acid, cystine, and/or other compounds or combinations thereof.

Several methods can be used for treating patients with kidney stones, including observation, medical treatments (such as expulsion therapy), non-invasive treatments (such as extracorporeal shock wave lithotripsy (ESWL)), minimally-invasive or surgical treatments (such as ureteroscopy and percutaneous nephrolithotomy ("PCNL")), and so on. In some approaches (e.g., ureteroscopy and PCNL), the physician gains access to the stone, the stone is broken into smaller pieces or fragments, and the relatively small stone fragments/particulates are extracted from the kidney using a basketing device and/or aspiration.

In some procedures, surgeons may insert an endoscope (e.g., ureteroscope) into the urinary tract through the urethra to remove urinary stones from the bladder and ureter. Typically, a ureteroscope includes a camera at its distal end configured to enable visualization of the urinary tract. The ureteroscope can also include, or allow for placement in a working channel of the ureteroscope, a lithotripsy device configured to capture or break apart urinary stones. During a ureteroscopy procedure, one physician/technician may control the position of the ureteroscope, while another physician/technician may control the lithotripsy device(s).

In some procedures, such as procedures for removing relatively large stones/fragments, physicians may use a percutaneous nephrolithotomy ("PCNL") technique that involves inserting a nephroscope through the skin (i.e., percutaneously) and intervening tissue to provide access to the treatment site for breaking-up and/or removing the stone(s). A percutaneous-access device (e.g., nephroscope, sheath, sheath assembly, and/or catheter) used to provide an access channel to the target anatomical site (and/or a direct-entry endoscope) may include one or more fluid channels for providing irrigation fluid flow to the target site and/or aspirating fluid from the target site (e.g., through passive outflow and/or active suction).

For ureteroscopic procedures, a physician may implement a procedure to break a relatively large kidney stone into a relatively smaller fragments to facilitate extraction thereof. For example, certain instruments may be utilized to break the stone into smaller fragments, such as by lasing, or through other application of cleaving force to the kidney stone. According to some procedures, a basketing device/system may be used to capture the relatively smaller stone fragment(s) and extract them from the treatment site out of the patient. Generally, when a stone is captured, the surgeon may wish to quickly extract the stone through the uretereral access sheath prior to opening the basket to deposit/drop the stone into a specimen collection structure or area, after which the basket may be closed and reinserted (e.g., within a working channel of an endoscope/ureteroscope) through the access sheath for the purpose of extracting remaining stones or stone fragments, should there be any.

Robotic-assisted ureteroscopic procedures can be implemented in connection with various medical procedures, such as kidney stone removal procedures, wherein robotic tools can enable a physician/urologist to perform endoscopic target access as well as percutaneous access/treatment. Advantageously, aspects of the present disclosure relate to systems, devices, and methods for robotically controlling axial rotation/rolling of endoscopes/ureteroscopes to improve procedural efficiency and efficacy.

Medical System

FIG. 1 illustrates an example medical system 100 for performing various medical procedures in accordance with aspects of the present disclosure. The medical system 100 may be used for, for example, endoscopic (e.g., ureteroscopic) procedures. As referenced and described above, certain ureteroscopic procedures involve the treatment/removal of kidney stones. In some implementations, kidney stone treatment can benefit from the assistance of certain robotic technologies/devices. Robotic medical solutions can provide relatively higher precision, superior control, and/or superior hand-eye coordination with respect to certain instruments compared to strictly-manual procedures. For example, robotic-assisted ureteroscopic access to the kidney in accordance with some procedures can advantageously enable a urologist to individually perform both endoscope control and basketing control.

Although the system 100 of FIG. 1 is presented in the context of a ureteroscopic procedure, it should be understood that the principles disclosed herein may be implemented in any type of endoscopic procedure. Furthermore, several of the examples described herein relate to object removal procedures involving the removal of kidney stones from a kidney. The present disclosure, however, is not limited only to kidney stone removal. For example, the following description is also applicable to other surgical or medical operations or medical procedures concerned with the removal of objects from a patient, including any object that can be removed from a treatment site or patient cavity (e.g., the esophagus, ureter, intestine, eye, etc.) via percutaneous and/or endoscopic access, such as, for example, gallbladder stone removal, lung (pulmonary/transthoracic) tumor biopsy, or cataract removal.

The medical system 100 includes a robotic system 10 (e.g., mobile robotic cart) configured to engage with and/or control a medical instrument 19 (e.g., ureteroscope) including a proximal handle 31 and a shaft 40 coupled to the handle 31 at a proximal portion thereof to perform a direct-entry procedure on a patient 7. The term "direct-entry" is used herein according to its broad and ordinary meaning and may refer to any entry of instrumentation through a natural or artificial opening in a patient's body. For example, with reference to FIG. 1, the direct entry of the scope/shaft 40 into the urinary tract of the patient 7 may be made via the urethra 65.

It should be understood that the direct-entry instrument 19 may be any type of shaft-based medical instrument, including an endoscope (such as a ureteroscope), catheter (such as a steerable or non-steerable catheter), nephroscope, laparoscope, or other type of medical instrument. Embodiments of the present disclosure relating to ureteroscopic procedures for removal of kidney stones through a ureteral access sheath (e.g., the ureteral access sheath 190 are also applicable to solutions for removal of objects through percutaneous access, such as through a percutaneous access sheath. For example, instrument(s) may access the kidney percutaneously through, for example, a percutaneous access sheath to capture and remove kidney stones. The term "percutaneous access" is used herein according to its broad and ordinary meaning and may refer to entry, such as by puncture and/or minor incision, of instrumentation through the skin of a patient and any other body layers necessary to reach a target anatomical location associated with a procedure (e.g., the calyx network of the kidney 70).

The medical system 100 includes a control system 50 configured to interface with the robotic system 10, provide information regarding the procedure, and/or perform a variety of other operations. For example, the control system 50 can include one or more display(s) 56 configured to present certain information to assist the physician 5 and/or other technician(s) or individual(s). The medical system 100 can include a table 15 configured to hold the patient 7. The system 100 may further include an electromagnetic (EM) field generator 18, which may be held by one or more of the robotic arms 12 of the robotic system 10 or may be a stand-alone device. Although the various robotic arms 12 are shown in various positions and coupled to various tools/devices, it should be understood that such configurations are shown for convenience and illustration purposes, and such robotic arms may have different configurations over time and/or at different points during a medical procedure. Furthermore, the robotic arms 12 may be coupled to different devices/instruments than shown in FIG. 1, and in some cases or periods of time, one or more of the arms may not be utilized or coupled to a medical instrument (e.g., instrument manipulator/coupling). Roll of the shaft 40 may be controlled robotically and/or manually, such as through operation of an end effector associated with the robot arm 12a, wherein such operation may be controlled by the control system 50 and/or robotic system 10. The term "end effector" is used herein according to its broad and ordinary meaning and may refer to any type of robotic manipulator device, component, and/or assembly. Where an adapter, such as a sterile adapter, is coupled to a robotic end effector or other robotic manipulator, the term "end effector" may refer to the adapter (e.g., sterile adapter), or any other robotic manipulator device, component, or assembly associated with and/or coupled to the end effector. In some contexts, the combination of a robotic end effector and adapter may be referred to as an instrument manipulator assembly, wherein such assembly may or may not also include a medical instrument (or instrument handle/base) physically coupled to the adapter and/or end effector. The terms "robotic manipulator" and "robotic manipulator assembly are used according to their broad and ordinary meanings, and may refer to a robotic end effector and/or sterile adapter or other adapter component coupled to the end effector, either collectively or individually. For example, "robotic manipulator" or "robotic manipulator assembly" may refer to an instrument device manipulator (IDM) including one or more drive outputs, whether embodied in a robotic end effector, sterile adapter, and/or other component(s).

In an example use case, if the patient 7 has a kidney stone (or stone fragment) 180 located in a kidney 70, the physician may execute a procedure to remove the stone 180 through the urinary tract (63, 60, 65). In some embodiments, the physician 5 can interact with the control system 50 and/or the robotic system 10 to cause/control the robotic system 10 to advance and navigate the medical instrument shaft 40 (e.g., a scope) from the urethra 65, through the bladder 60, up the ureter 63, and into the renal pelvis 71 and/or calyx network of the kidney 70 where the stone 180 is located. The physician 5 can further interact with the control system 50 and/or the robotic system 10 to cause/control the advancement of a basketing device 30 through a working channel of the instrument shaft 40, wherein the basketing device 30 is configured to facilitate capture and removal of a kidney stone or stone fragment. The control system 50 can provide information via the display(s) 56 that is associated with the medical instrument 40, such as real-time endoscopic images captured therewith, and/or other instruments of the system 100, to assist the physician 5 in navigating/controlling such instrumentation.

The renal anatomy is described herein for reference with respect to certain medical procedures relating to aspects of the present inventive concepts. The kidneys 70, shown roughly in typical anatomical position in FIG. 1, generally comprise two bean-shaped organs located on the left and right sides, respectively, in the retroperitoneal space. In adult humans, the kidneys are generally about 11 cm in height/length. The kidneys receive blood from the paired renal arteries 69; blood exits the kidney via the paired renal veins 67. Each kidney 70 is fluidly coupled with a respective ureter 63, which generally comprises a tube that carries excreted urine from the kidney 70 to the bladder 60.

The kidneys 70 are typically located relatively high in the abdominal cavity and lie in a retroperitoneal position at a slightly oblique angle. The asymmetry within the abdominal cavity, generally caused by the position of the liver, results in the right kidney (shown in detail in FIG. 1) typically being slightly lower and smaller than the left, and being placed slightly more to the middle than the left kidney. On top of each kidney is an adrenal gland (not shown). The upper parts of the kidneys 70 are partially protected by the $11^{th}$ and $12^{th}$ ribs (not shown). Each kidney, with its adrenal gland, is generally surrounded by two layers of fat: the perirenal fat present between renal fascia and renal capsule and pararenal fat superior to the renal fascia.

The kidneys 70 participate in the control of the volumes of various body fluid compartments, fluid osmolality, acid-base balance, various electrolyte concentrations, and removal of toxins. The kidneys 70 provide filtration functionality by secreting certain substances and reabsorbing others. Examples of substances secreted into the urine are hydrogen, ammonium, potassium and uric acid. In addition, the kidneys also carry out various other functions, such as hormone synthesis, and others.

A recessed area on the concave border of the kidney 70 is the renal hilum 181, where the renal artery 69 (not shown in the detailed view of the kidney 70) enters the kidney 70 and the renal vein 67 (not shown in detailed view) and ureter 63 leave. The kidney 70 is surrounded by tough fibrous tissue, the renal capsule 74, which is itself surrounded by perirenal fat, renal fascia, and pararenal fat. The anterior (front) surface of these tissues is the peritoneum, while the posterior (rear) surface is the transversalis fascia.

The functional substance, or parenchyma, of the kidney 70 is divided into two major structures: the outer renal cortex 77 and the inner renal medulla 187. These structures take the shape of a plurality of generally cone-shaped renal lobes, each containing renal cortex surrounding a portion of medulla called a renal pyramid 72. Between the renal pyramids 72 are projections of cortex called renal columns 73. Nephrons (not shown in detail in FIG. 1), the urine-producing functional structures of the kidney, span the cortex 77 and medulla 187. The initial filtering portion of a nephron is the renal corpuscle, which is located in the cortex and is followed by a renal tubule that passes from the cortex deep into the medullary pyramids. Part of the renal cortex, a medullary ray, is a collection of renal tubules that drain into a single collecting duct.

The tip/apex, or papilla 79, of each renal pyramid empties urine into a respective minor calyx 75; minor calyces 75 empty into major calyces 76, and major calyces 76 empty into the renal pelvis 71, which transitions to the ureter 63. The manifold-type collection of minor and major calyces may be referred to herein as the "calyx network" of the kidney. At the hilum 181, the ureter 63 and renal vein 67 exit the kidney and the renal artery 69 enters. Hilar fat and lymphatic tissue with lymph nodes surround these structures. The hilar fat is contiguous with a fat-filled cavity called the renal sinus. The renal sinus collectively contains the renal pelvis 71 and calyces 75, 76 and separates these structures from the renal medullary tissue. The funnel/tubular-shaped anatomy associated with the calyces can be referred to as the infundibulum/infundibula. That is, an infundibulum generally leads to the termination of a calyx where a papilla is exposed within the calyx.

With further reference to the medical system 100, the medical instrument shaft 40 (e.g., scope, directly-entry instrument, etc.) can be advanced into the kidney 70 through the urinary tract. Specifically, a ureteral access sheath 190 may be disposed within the urinary tract to an area near the kidney 70. The shaft 40 may be passed through the ureteral access sheath 190 to gain access to the internal anatomy of the kidney 70, as shown. Once at the site of the kidney stone 180 (e.g., within a target calyx 75 of the kidney 70 through which the stone 180 is accessible), the medical instrument 19 and/or shaft 40 thereof can be used to channel/direct the basketing device 30 to the target location. Once the stone 180 has been captured in the distal basket portion 35 of the basketing device/assembly 30, the utilized ureteral access path may be used to extract the kidney stone 180 from the patient 7.

The various scope/shaft-type instruments disclosed herein, such as the shaft 40 of the system 100, can be configured to navigate within the human anatomy, such as within a natural orifice or lumen of the human anatomy. The terms "scope" and "endoscope" are used herein according to their broad and ordinary meanings, and may refer to any type of elongate (e.g., shaft-type) medical instrument having image generating, viewing, and/or capturing functionality and being configured to be introduced into any type of organ, cavity, lumen, chamber, or space of a body. A scope can include, for example, a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), colonoscope (e.g., for accessing the colon and/or rectum), borescope, and so on. Scopes/endoscopes, in some instances, may comprise an at least partially rigid and/or flexible tube, and may be dimensioned to be passed within an outer sheath, catheter, introducer, or other lumen-type device, or may be used without such devices.

Figure 2:
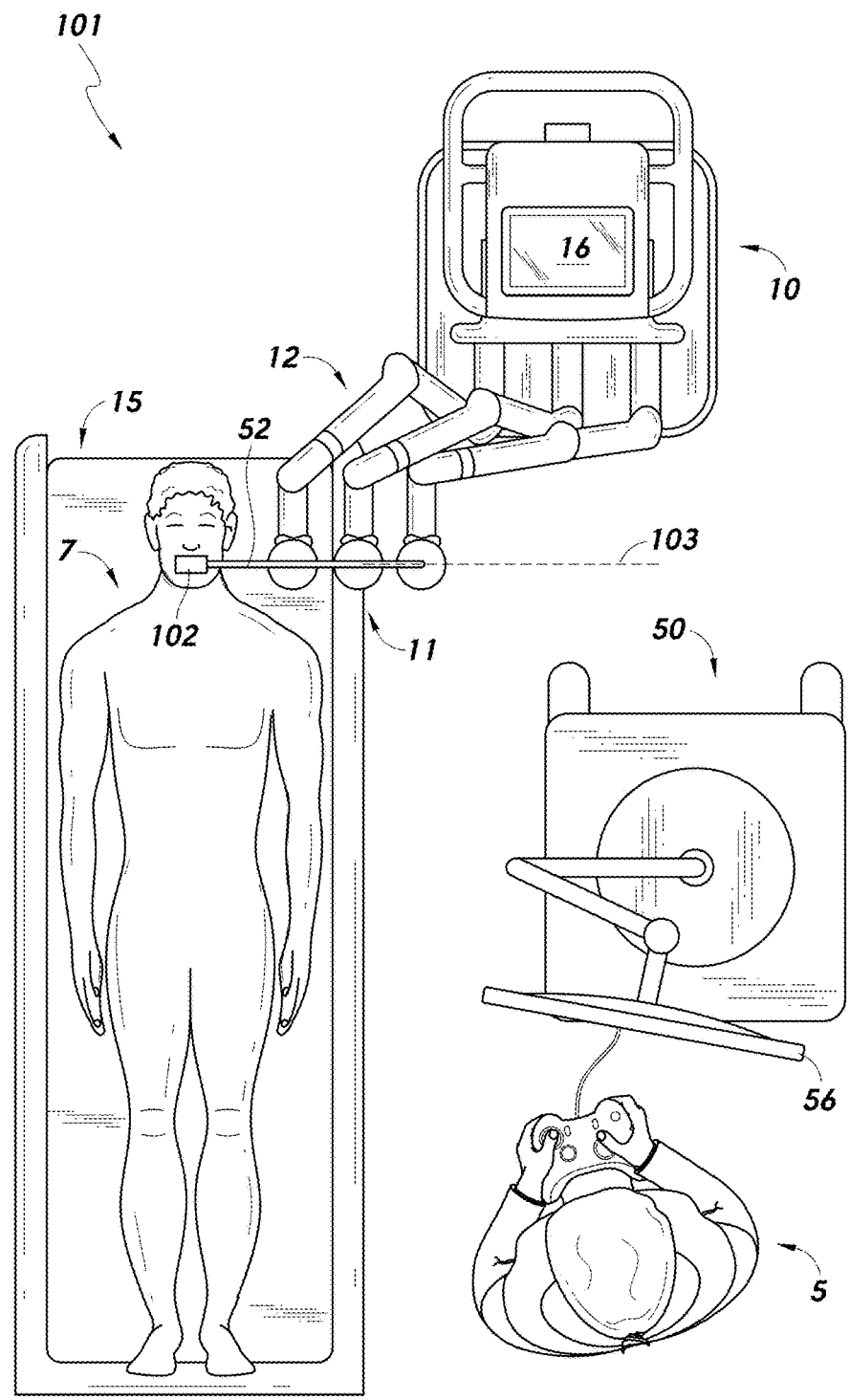
FIG. 2 illustrates a robotic system arranged for diagnostic and/or therapeutic bronchoscopy in accordance with one or more embodiments.

FIG. 2 illustrates a cart-based robotic system 101 arranged for diagnostic and/or therapeutic bronchoscopy in accordance with one or more embodiments. During a bronchoscopy, the arm(s) 12 of the robotic system 10 may be configured to drive a medical instrument shaft 52, such as a steerable endoscope, which may be a procedure-specific bronchoscope for bronchoscopy, through a natural orifice access point (e.g., the mouth of the patient 7 positioned on a table 15 in the present example) to deliver diagnostic and/or therapeutic tools. As shown, the robotic system 10 (e.g., cart) may be positioned proximate to the patient's upper torso in order to provide access to the access point. Similarly, the robotic arms 12 may be actuated to position the bronchoscope/shaft 52 relative to the access point. The arrangement in FIG. 2 may also be utilized when performing a gastro-intestinal (GI) procedure with a gastroscope, a specialized endoscope for GI procedures.

Once the robotic system 10 is properly positioned, the robotic arms 12 may insert the steerable endoscope 52 into the patient robotically, manually, or a combination thereof. The steerable endoscope 52 may comprise at least two telescoping parts, such as an inner leader portion and an outer sheath portion, each portion coupled to a separate instrument feeder from the set of instrument feeders and/or instrument handles 111, each instrument feeder/handle being coupled to the distal end of a respective robotic arm 12. This linear arrangement of the feeder(s)/handle(s) 111 can create a "virtual rail" 103 that may be repositioned in space by manipulating the one or more robotic arms 12 into different angles and/or positions. One or more of the instrument feeder(s)/handle(s) 111 can be configured to implement robotic roll of the shaft and may be configured according to one or more embodiments disclosed herein for such purpose.

The endoscope 52 may be directed down the patient's trachea and lungs after insertion using precise commands from the robotic system 10 until reaching the target operative site. For example, the endoscope 52 may be directed to deliver a biopsy needle to a target, such as, for example, a lesion or nodule within the lungs of a patient. The needle may be deployed down a working channel that runs the length of the endo scope to obtain a tissue sample to be analyzed by a pathologist. Depending on the pathology results, additional tools may be deployed down the working channel of the endoscope for additional biopsies. For example, when a nodule is identified as being malignant, the endoscope 52 may endoscopically deliver tools to resect the potentially cancerous tissue. In some instances, diagnostic and therapeutic treatments can be delivered in separate procedures. In those circumstances, the endoscope 52 may also be used to deliver a fiducial to "mark" the location of the target nodule as well. In other instances, diagnostic and therapeutic treatments may be delivered during the same procedure.

In the system 101, a patient introducer 102 is attached to the patient 7 via a port (not shown; e.g., surgical tube). The curvature of the introducer 102 may enable the robotic system 10 to manipulate the instrument 52 from a position that is not in direct axial alignment with the patient-access port, thereby allowing for greater flexibility in the placement of the robotic system 10 within the room. Further, the curvature of the introducer 102 may allow the robotic arms 12 of the robotic system 10 to be substantially horizontally aligned with the patient introducer 102, which may facilitate manual movement of the robotic arm(s) 12 if needed. The control system 50 and/or robotic cart 10 can include control circuitry configured to implement scope roll control as described herein.

Figure 3:
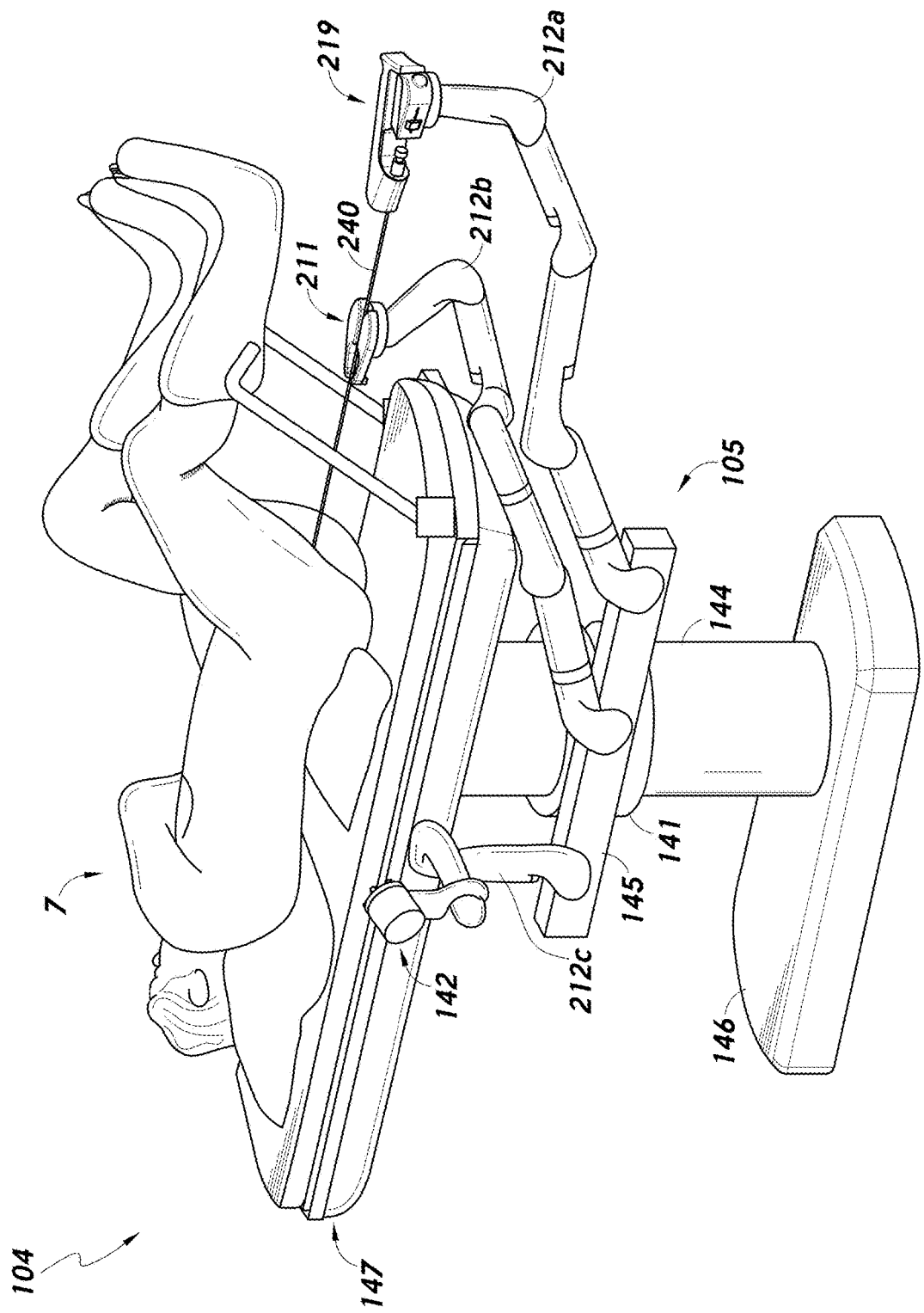
FIG. 3 illustrates a table-based robotic system in accordance with one or more embodiments.

FIG. 3 illustrates a table-based robotic system 104 in accordance with one or more embodiments of the present disclosure. The system 104 incorporates robotic components 105 with a table/platform 147, thereby allowing for a reduced amount of capital equipment within the operating room compared to some cart-based robotic systems, which can allow greater access to the patient 7 in some instances. Much like in the cart-based systems, the instrument device manipulator assemblies associated with the robotic arms 212 of the system 104 may generally comprise instruments and/or instrument feeders that are designed to manipulate an elongated medical instrument/shaft, such as a catheter 48 or the like, along a virtual rail or path.

As shown, the robotic-enabled table system 104 can include a column 144 coupled to one or more carriages 141 (e.g., ring-shaped movable structures), from which the one or more robotic arms 212 may emanate. The carriage(s) 141 may translate along a vertical column interface that runs at least a portion of the length of the column 144 to provide different vantage points from which the robotic arms 212 may be positioned to reach the patient 7. The carriage(s) 141 may rotate around the column 144 in some embodiments using a mechanical motor positioned within the column 144 to allow the robotic arms 212 to have access to multiples sides of the table 104. Rotation and/or translation of the carriage(s) 141 can allow the system 104 to align the medical instruments, such as endoscopes and catheters, into different access points on the patient. By providing vertical adjustment, the robotic arms 212 can advantageously be configured to be stowed compactly beneath the platform 147 of the table system 104 and subsequently raised during a procedure.

The robotic arms 212 may be mounted on the carriage(s) 141 through one or more arm mounts 145, which may comprise a series of joints that may individually rotate and/or telescopically extend to provide additional configurability to the robotic arms 212. The column 144 structurally provides support for the table platform 147 and a path for vertical translation of the carriage(s) 141. The column 144 may also convey power and control signals to the carriage(s) 141 and/or the robotic arms 212 mounted thereon. The system 104 can include certain control circuitry configured to control driving and/or roll of the instrument shaft 240 using the instrument feeder 211, which may be coupled to an end effector of one of the arms 212, wherein the instrument feeder 211 is controlled to automatically modify axial driving speed with respect to the elongate instrument (e.g., endoscope) 48 based on a determined position of a distal end of the instrument 48. For example, when the distal end of the instrument 48 is positioned at a predetermined automatic pause location, the instrument feeder 211 can be controlled/driven to automatically pause/stop axial retraction to allow for specimen collection, as described in detail herein.

With reference to FIGS. 1-3 and FIG. 4-1, which shows an example embodiment of the control systems of any of FIGS. 1-3, the relevant control system 50 can be configured to provide various functionality to assist in performing a medical procedure. In some embodiments, the control system 50 can be coupled to the robotic system 10 and operate in cooperation therewith to perform a medical procedure on the patient 7. For example, the control system 50 can communicate with the robotic system 10 via a wireless or wired connection (e.g., to control the robotic system 10). Further, in some embodiments, the control system 50 can communicate with the robotic system 10 to receive position data therefrom relating to the position of the distal end of the scope 40, access sheath 190, or basketing device 30. Such positional data relating to the position of the scope 40, access sheath 190, or basketing device 30 may be derived using one or more electromagnetic sensors associated with the respective components, scope image processing functionality, and/or based at least in part on robotic system data (e.g., arm position data, known parameters/dimensions of the various system components, etc.). Moreover, in some embodiments, the control system 50 can communicate with the table 15 to position the table 15 in a particular orientation or otherwise control the table 15. In some embodiments, the control system 50 can communicate with the EM field generator 18 to control generation of an EM field in an area around the patient 7 and/or around the instrument feeder 11.

Figures 1, 4:
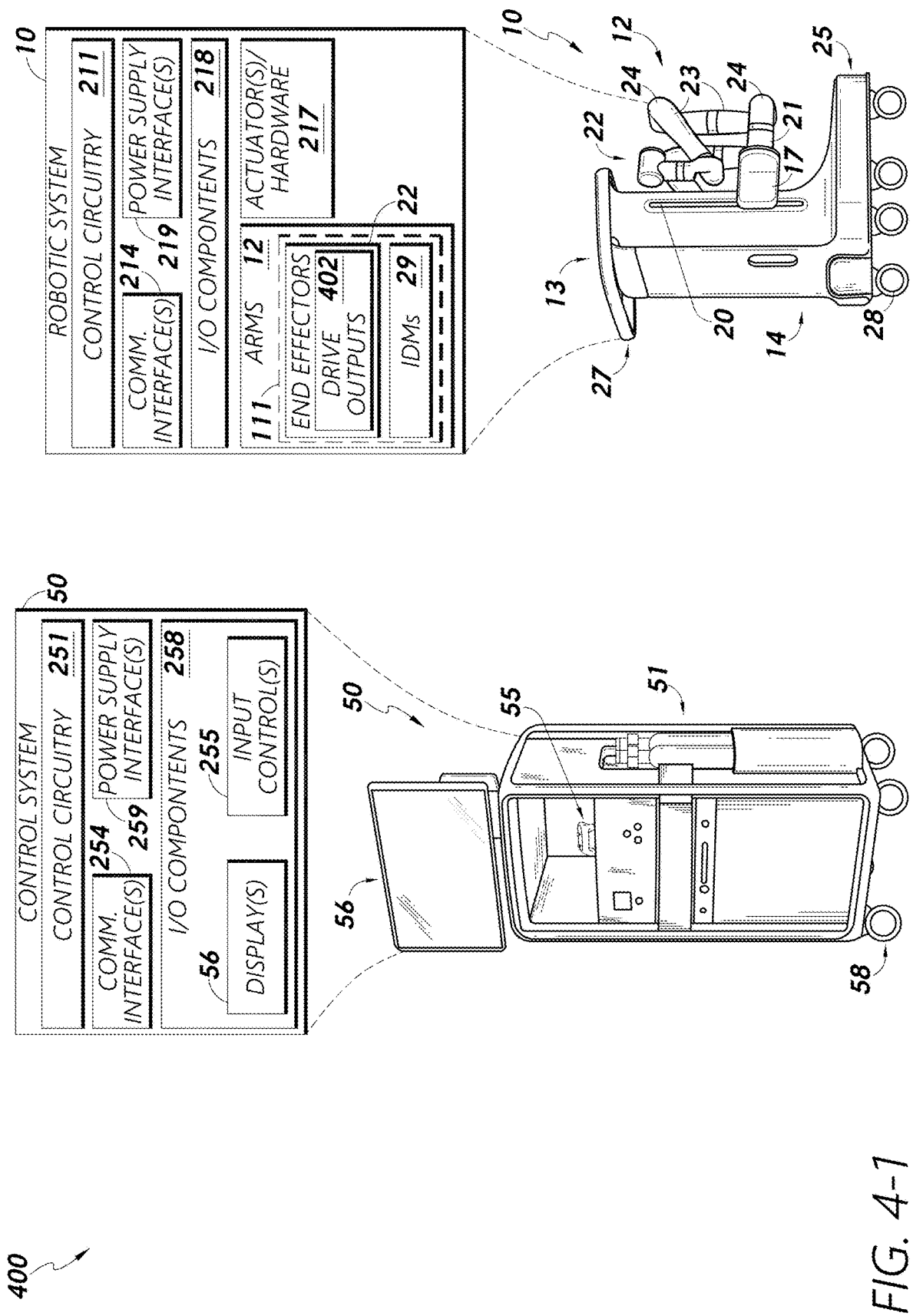
Figures 2, 4:
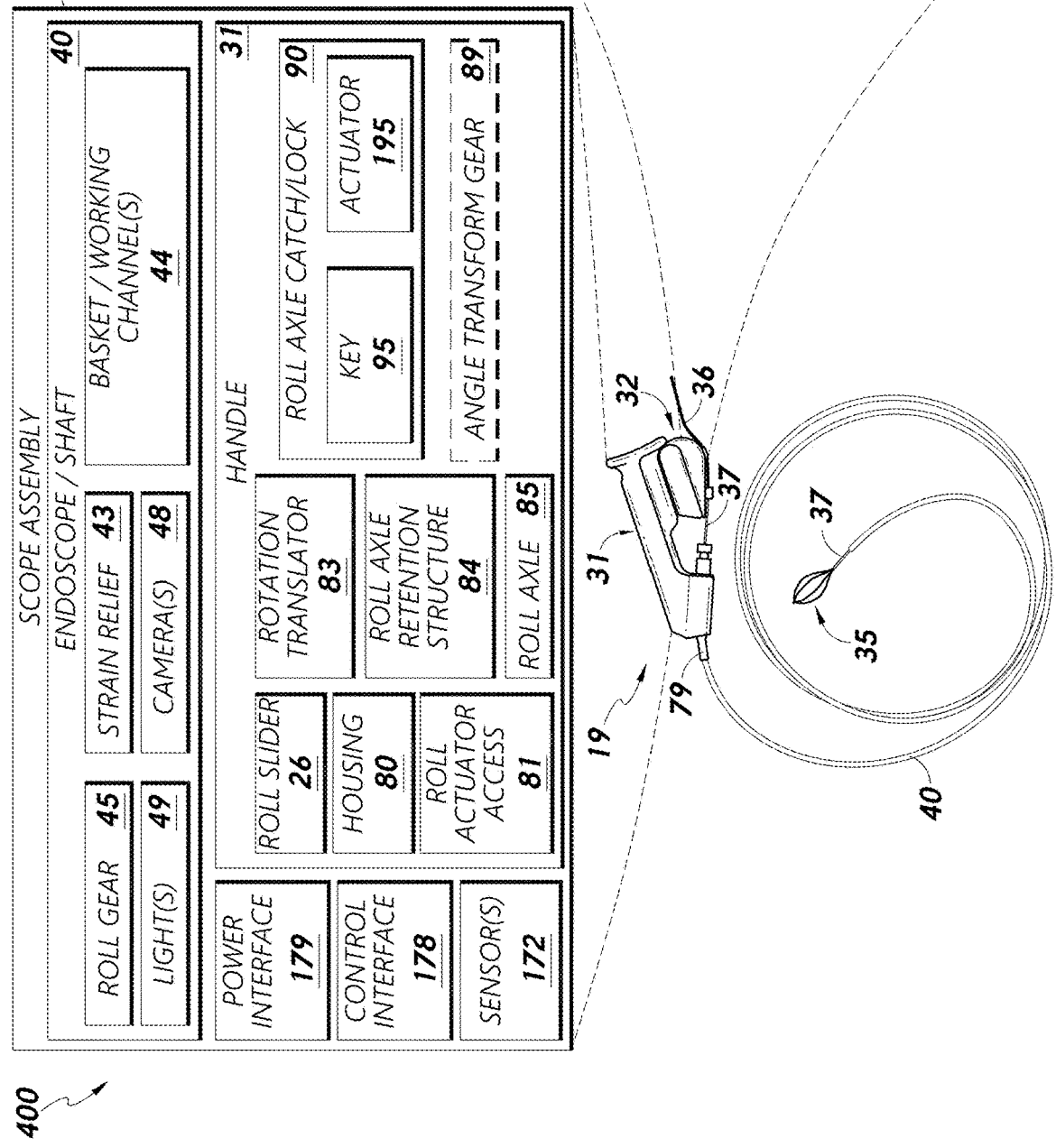

FIG. 4-1 further shows an example embodiment of the robotic systems of any of FIGS. 1-3. The robotic system 10 can be configured to at least partly facilitate execution of a medical procedure. The robotic system 10 can be arranged in a variety of ways depending on the particular procedure. The robotic system 10 can include one or more robotic arms 12 configured to engage with and/or control, for example, the scope 40 and/or the basketing device/system 30 to perform one or more aspects of a procedure. As shown, each robotic arm 12 can include multiple arm segments 23 coupled to joints 24, which can provide multiple degrees of movement/freedom. In the example of FIG. 1, the robotic system 10 is positioned proximate to the patient's legs and the robotic arms 12 are actuated to engage with and position the scope 40 for access into an access opening, such as the urethra 65 of the patient 7. When the robotic system 10 is properly positioned, the scope 40 can be inserted into the patient 7 robotically using the robotic arms 12, manually by the physician 5, or a combination thereof. With reference to FIG. 1, a scope-driver/feeder instrument coupling 11 (i.e., instrument device manipulator (IDM)) can be attached to the distal end effector 22 of one of the arms 12b to facilitate robotic control/advancement of the scope 40. Another 12a of the arms may have associated therewith an instrument coupling/manipulator 19 that is configured to facilitate advancement and operation of the basketing device 30. The instrument coupling 19 may further provide a handle 31 for the scope 40, wherein the scope 40 is physically coupled to the handle 31 at a proximal end of the scope 40. The scope 40 may include one or more working channels through which additional tools, such as lithotripters, basketing devices, forceps, etc., can be introduced into the treatment site.

The robotic system 10 can be coupled to any component of the medical system 100, such as to the control system 50, the table 15, the EM field generator 18, the scope 40, the basketing system 30, and/or any type of percutaneous-access instrument (e.g., needle, catheter, nephroscope, etc.). In some embodiments, the robotic system 10 is communicatively coupled to the control system 50. For example, the robotic system 10 may be configured to receive control signals from the control system 50 to perform certain operations, such as to position one or more of the robotic arms 12 in a particular manner, manipulate the scope 40, manipulate the basketing system 30, and so on. In response, the robotic system 10 can control, using certain control circuitry 211, actuators 217, and/or other components of the robotic system 10, a component of the robotic system 10 to perform the operations. For example, the control circuitry 211 may control roll of the shaft/scope 40 by actuating drive output(s) 402 of the end effector 22 coupled to the instrument handle 31. In some embodiments, the robotic system 10 and/or control system 50 is/are configured to receive images and/or image data from the scope 40 representing internal anatomy of the patient 7 and/or portions of the access sheath or other device components.

The robotic system 10 generally includes an elongated support structure 14 (also referred to as a "column"), a robotic system base 25, and a console 13 at the top of the column 14. The column 14 may include one or more arm supports 17 (also referred to as a "carriage") for supporting the deployment of the one or more robotic arms 12 (three shown in FIG. 1). The arm support 17 may include individually-configurable arm mounts that rotate along a perpendicular axis to adjust the base of the robotic arms 12 for desired positioning relative to the patient.

The arm support 17 may be configured to vertically translate along the column 14. In some embodiments, the arm support 17 can be connected to the column 14 through slots 20 that are positioned on opposite sides of the column 14 to guide the vertical translation of the arm support 17. The slot 20 contains a vertical translation interface to position and hold the arm support 17 at various vertical heights relative to the robotic system base 25. Vertical translation of the arm support 17 allows the robotic system 10 to adjust the reach of the robotic arms 12 to meet a variety of table heights, patient sizes, and physician preferences. Similarly, the individually-configurable arm mounts on the arm support 17 can allow the robotic arm base 21 of robotic arms 12 to be angled in a variety of configurations.

The robotic arms 12 may generally comprise robotic arm bases 21 and end effectors 22, separated by a series of linking arm segments 23 that are connected by a series of joints 24, each joint comprising one or more independent actuators 217. Each actuator may comprise an independently-controllable motor. Each independently-controllable joint 24 can provide or represent an independent degree of freedom available to the robotic arm. In some embodiments, each of the arms 12 has seven joints, and thus provides seven degrees of freedom, including "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The robotic system base 25 balances the weight of the column 14, arm support 17, and arms 12 over the floor. Accordingly, the robotic system base 25 may house certain relatively heavier components, such as electronics, motors, power supply, as well as components that selectively enable movement or immobilize the robotic system. For example, the robotic system base 25 can include wheel-shaped casters 28 that allow for the robotic system to easily move around the operating room prior to a procedure. After reaching the appropriate position, the casters 28 may be immobilized using wheel locks to hold the robotic system 10 in place during the procedure.

Positioned at the upper end of column 14, the console 13 can provide both a user interface for receiving user input and a display screen 16 (or a dual-purpose device such as, for example, a touchscreen) to provide the physician/user with both pre-operative and intra-operative data. Potential pre-operative data on the console/display 16 or display 56 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 13 may be positioned and tilted to allow a physician to access the console from the side of the column 14 opposite arm support 17. From this position, the physician may view the console 13, robotic arms 12, and patient while operating the console 13 from behind the robotic system 10. As shown, the console 13 can also include a handle 27 to assist with maneuvering and stabilizing the robotic system 10.

The end effector 22 of each of the robotic arms 12 may comprise, or be configured to have coupled thereto, an instrument device manipulator (IDM) 29, which may be attached using a sterile adapter component in some instances. The combination of the end effector 22 and associated IDM, as well as any intervening mechanics or couplings (e.g., sterile adapter), can be referred to as a manipulator assembly 111. In some embodiments, the IDM 29 can be removed and replaced with a different type of IDM, for example, a first type 11 of IDM/instrument may be configured to manipulate an endoscope/shaft, while a second type 19 of IDM/instrument may be associated with the shaft (e.g., coupled to a proximal portion thereof) and configured to roll and/or articulate the shaft, and/or manipulate a basketing device. Another type of IDM/instrument may be configured to hold an electromagnetic field generator 18. An IDM can provide power and control interfaces. For example, the interfaces can include connectors to transfer pneumatic pressure, electrical power, electrical signals, and/or optical signals from the robotic arm 12 to the IDM. The IDMs 29 may be configured to manipulate medical instruments (e.g., surgical tools/instruments), such as the scope 40, using techniques including, for example, direct drives, harmonic drives, geared drives, belts and pulleys, magnetic drives, and the like. In some embodiments, the device manipulators 29 can be attached to respective ones of the robotic arms 12, wherein the robotic arms 12 are configured to insert or retract the respective coupled medical instruments into or out of the treatment site.

As referenced above, the system 100 can include certain control circuitry configured to perform certain of the functionality described herein, including the control circuitry 211 of the robotic system 10 and the control circuitry 251 of the control system 50. That is, the control circuitry of the systems 100, 101, 104 may be part of the robotic system 10, the control system 50, or some combination thereof. Therefore, any reference herein to control circuitry may refer to circuitry embodied in a robotic system, a control system, or any other component of a medical system, such as the medical systems 100, 101, and 104 shown in FIGS. 1-3, respectively. The term "control circuitry" is used herein according to its broad and ordinary meaning, and may refer to any collection of processors, processing circuitry, processing modules/units, chips, dies (e.g., semiconductor dies including one or more active and/or passive devices and/or connectivity circuitry), microprocessors, micro-controllers, digital signal processors, microcomputers, central processing units, field-programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry referenced herein may further include one or more circuit substrates (e.g., printed circuit boards), conductive traces and vias, and/or mounting pads, connectors, and/or components. Control circuitry referenced herein may further comprise one or more storage devices, which may be embodied in a single memory device, a plurality of memory devices, and/or embedded circuitry of a device. Such data storage may comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware and/or software state machine, analog circuitry, digital circuitry, and/or logic circuitry, data storage device(s)/register(s) storing any associated operational instructions may be embedded within, or external to, the circuitry comprising the state machine, analog circuitry, digital circuitry, and/or logic circuitry.

Figures 2, 3, 15, 16:
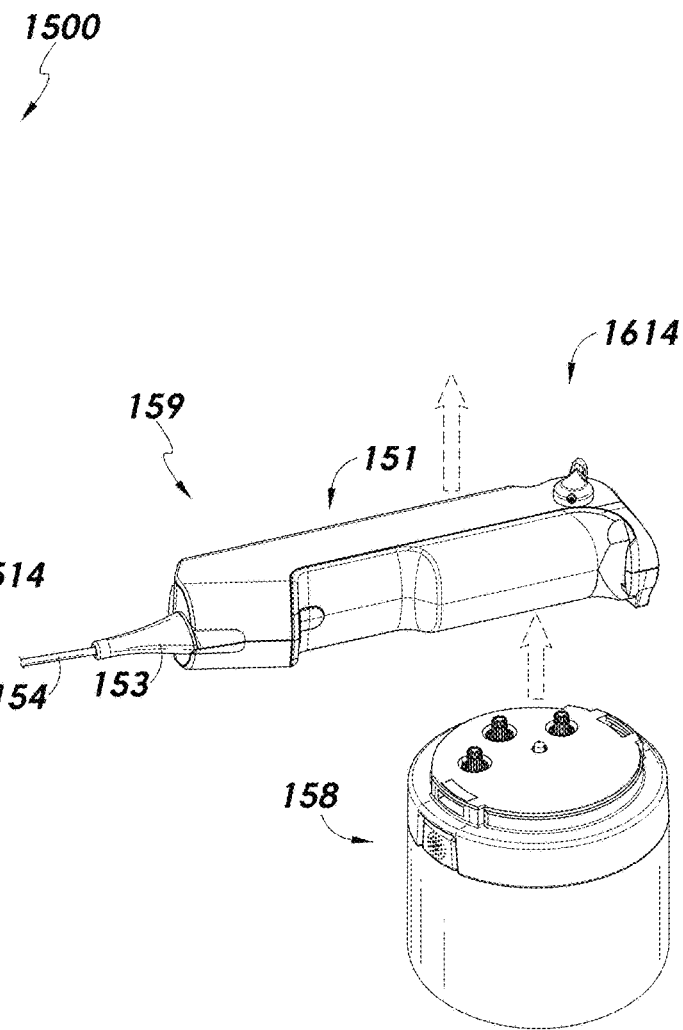

The control circuitry 211, 251 may comprise computer-readable media storing, and/or configured to store, hard-coded and/or operational instructions corresponding to at least some of the steps and/or functions illustrated in one or more of the present figures and/or described herein. Such computer-readable media can be included in an article of manufacture in some instances. The control circuitry 211/251 may be entirely locally maintained/disposed or may be remotely located at least in part (e.g., communicatively coupled indirectly via a local area network and/or a wide area network). Any of the control circuitry 211, 251 may be configured to perform any aspect(s) of the various processes disclosed herein, including the processes shown in FIGS. 15-1 and 15-2, as described below.

With respect to the robotic system 10, at least a portion of the control circuitry 211 may be integrated with the base 25, column 14, and/or console 13 of the robotic system 10, and/or another system communicatively coupled to the robotic system 10. With respect to the control system 50, at least a portion of the control circuitry 251 may be integrated with the console base 51 and/or display unit 56 of the control system 50. It should be understood that any description herein of functional control circuitry or associated functionality may be understood to be embodied in the robotic system 10, the control system 50, or any combination thereof, and/or at least in part in one or more other local or remote systems/devices, such as control circuitry associated with a handle/base of a shaft-type instrument (e.g., endoscope) in accordance with any of the disclosed embodiments.

With further reference to FIG. 4-1, the control system 50 can include various I/O components 258 configured to assist the physician 5 or others in performing a medical procedure. For example, the input/output (I/O) components 258 can be configured to allow for user input to control/navigate the scope 40 and/or basketing system within the patient 7. In some embodiments, for example, the physician 5 can provide input to the control system 50 and/or robotic system 10, wherein in response to such input, control signals can be sent to the robotic system 10 to manipulate the scope 40 and/or catheter basketing system 30. The control system 50 can include one or more display devices 56 to provide various information regarding a procedure. For example, the display(s) 56 can provide information regarding the scope 40 and/or basketing system 30. For example, the control system 50 can receive real-time images that are captured by the scope 40 and display the real-time images via the display(s) 56. Additionally or alternatively, the control system 50 can receive signals (e.g., analog, digital, electrical, acoustic/sonic, pneumatic, tactile, hydraulic, etc.) from a medical monitor and/or a sensor associated with the patient 7, and the display(s) 56 can present information regarding the health or environment of the patient 7. Such information can include information that is displayed via a medical monitor including, for example, information relating to heart rate (e.g., ECG, HRV, etc.), blood pressure/rate, muscle bio-signals (e.g., EMG), body temperature, blood oxygen saturation (e.g., $SpO_2$), $CO_2$, brainwaves (e.g., EEG), environmental and/or local or core body temperature, and so on.

The various components of the system 100 can be communicatively coupled to each other over a network, which can include a wireless and/or wired network. Example networks include one or more personal area networks (PANs), local area networks (LANs), wide area networks (WANs), Internet area networks (IANs), cellular networks, the Internet, personal area networks (PANs), body area network (BANs), etc. For example, the various communication interfaces of the systems of FIG. 4-1 can be configured to communicate with one or more device/sensors/systems, such as over a wireless and/or wired network connection. In some embodiments, the various communication interfaces can implement a wireless technology such as Bluetooth, Wi-Fi, near-field communication (NFC), or the like. Furthermore, in some embodiments, the various components of the system 100 can be connected for data communication, fluid exchange, power exchange, and so on via one or more support cables, tubes, or the like.

The control system 50 and/or robotic system 10 can include certain user controls (e.g., controls 55), which may comprise any type of user input (and/or output) devices or device interfaces, such as one or more buttons, keys, joysticks, handheld controllers (e.g., video-game-type controllers), computer mice, trackpads, trackballs, control pads, and/or sensors (e.g., motion sensors or cameras) that capture hand gestures and finger gestures, touchscreens, and/or interfaces/connectors therefore. Such user controls are communicatively and/or physically coupled to respective control circuitry. In some embodiments, the user may engage the user controls 55 to command robotic shaft rotation/roll, as described herein.

FIG. 4-2 illustrates medical system components, including scope 519 and basketing 30 devices/assemblies 519 that may be implemented in any of the medical systems of FIGS. 1-3 in accordance with one or more embodiments. In some embodiments, the scope assembly 519 includes a handle or base 31 coupled to an endoscope 40. For example, the endoscope (i.e., "scope" or "shaft") can include an elongate shaft including one or more lights 49 and one or more cameras or other imaging devices 48. The scope 40 can further include one or more working channels 44, which may run a length of the scope 40. In some embodiments, such channel(s) may be utilized to provide access for elongate basketing wires/tines through the scope 40.

The basketing assembly 30 can comprise a basket 35 formed of one or more wire tines 36. For example, the basketing system 30 may comprise four wire tines disposed within a basketing sheath 37 over a length thereof, wherein the tines project from a distal end of the sheath 37 to form the basket form 35. The tines 36 further extend from the proximal end of the sheath 37. The tines 36 may be configured to be slidable within the basketing sheath 37, subject to some amount of frictional resistance. The tines 36 and the sheath 37 can be coupled to respective actuators 195 of a basket cartridge component 32. The basket cartridge 32 may be physically and/or communicatively coupled to the handle portion/component 31 of the scope assembly 519. The handle component 31 can be configured to be used to assist in basketing and/or scope control either manually or through robotic control.

The scope assembly 519 can be powered through a power interface 79 and/or controlled through a control interface 78, each or both of which may interface with a robotic arm/component of the robotic system 10. The scope assembly 519 may further comprise one or more sensors 72, such as pressure and/or other force-reading sensors, which may be configured to generate signals indicating forces experienced at/by one or more of the actuators 195 and/or other couplings of the scope/basket system 519.

The scope assembly 519 includes certain mechanisms for causing the shaft 40 to roll about an axis thereof (e.g., roll about an axis of the shaft at a base/proximal end thereof). For example, the shaft 40 may have associated with a proximal portion thereof a roll gear component 45. Such roll gear 45 may have one or more teeth or other feature(s) configured to mesh or engage with an actuator component associated with the handle 31 of the scope assembly 519. The scope assembly shaft 40 may be rolled/rotated by actuating the roll gear 45 using one or more actuator components (e.g., gears, belts, axles, etc.) associated with the handle 31. In some embodiments, the scope/shaft 40 includes a strain-relief component 43, which may include a rubber cone or other form/material configured to reduce the strain on the proximal portion/end of the shaft from bending of the shaft and/or to reduce the angle of bend at the proximal portion of the shaft.

The roll gear 45 of the shaft 40 may be disposed at least in part within the housing 80 of the handle 31. Furthermore, additional components configured to cause rolling/rotation of the roll gear 45 and shaft 40 may be disposed at least partially within the housing 80. In some embodiments, the handle 31 has associated therewith an externally-accessible/actuatable roll axle 85, which may comprise a drive input configured to be rotated about an axis when engaged with a drive output of a robotic end effector and/or adapter associated therewith. In some embodiments, the roll axle 85 has an axis that is transverse, orthogonal, and/or perpendicular to an axis of the roll gear 45 and/or shaft 40. Therefore, the handle 31 may further include an angle transform gear 89, which may be configured to translate/transform the rotation of the roll axle 85 to an axis that is parallel with the axis of the roll gear 45. The angle transform gear 89 may be, for example, a bevel gear in a mesh engagement with the roll axle 85 or the roll gear 45. The rotation/roll translator 83 may be configured to translate rotation of the roll axle 85 to rotation of the roll gear 45 through some sort of direct or indirect physical coupling between the roll axle 85 and the roll gear 45. For example, the roll translator 83 may comprise one or more belts, cables, rods, or the like. In some embodiments, the roll axle 85 is accessible via an aperture on an underside of the handle 31.

The scope assembly can further include a roll axle catch or lock means/mechanism 90, which may comprise a structure configured to be actuated to assume a locked configuration in which a key component 95 thereof is engaged with a mating feature of the roll axle 85, or to assume an unlocked position in which the key component 95 is not engaged with the mating feature of the roll axle 85. The roll axle catch 90 may further include an actuator component 91, which may be a unitary form with the body of the roll axle 90 and/or key feature 95. The actuator 91 may be accessible through an aperture or other access 81 in the housing 80, wherein the access 81 allows for actuation of the roll axle catch actuator 91 from external to the handle 31 and/or housing 80. The various components of the scope assembly 519 are described in greater detail below.

Scope Roll

Figure 5:
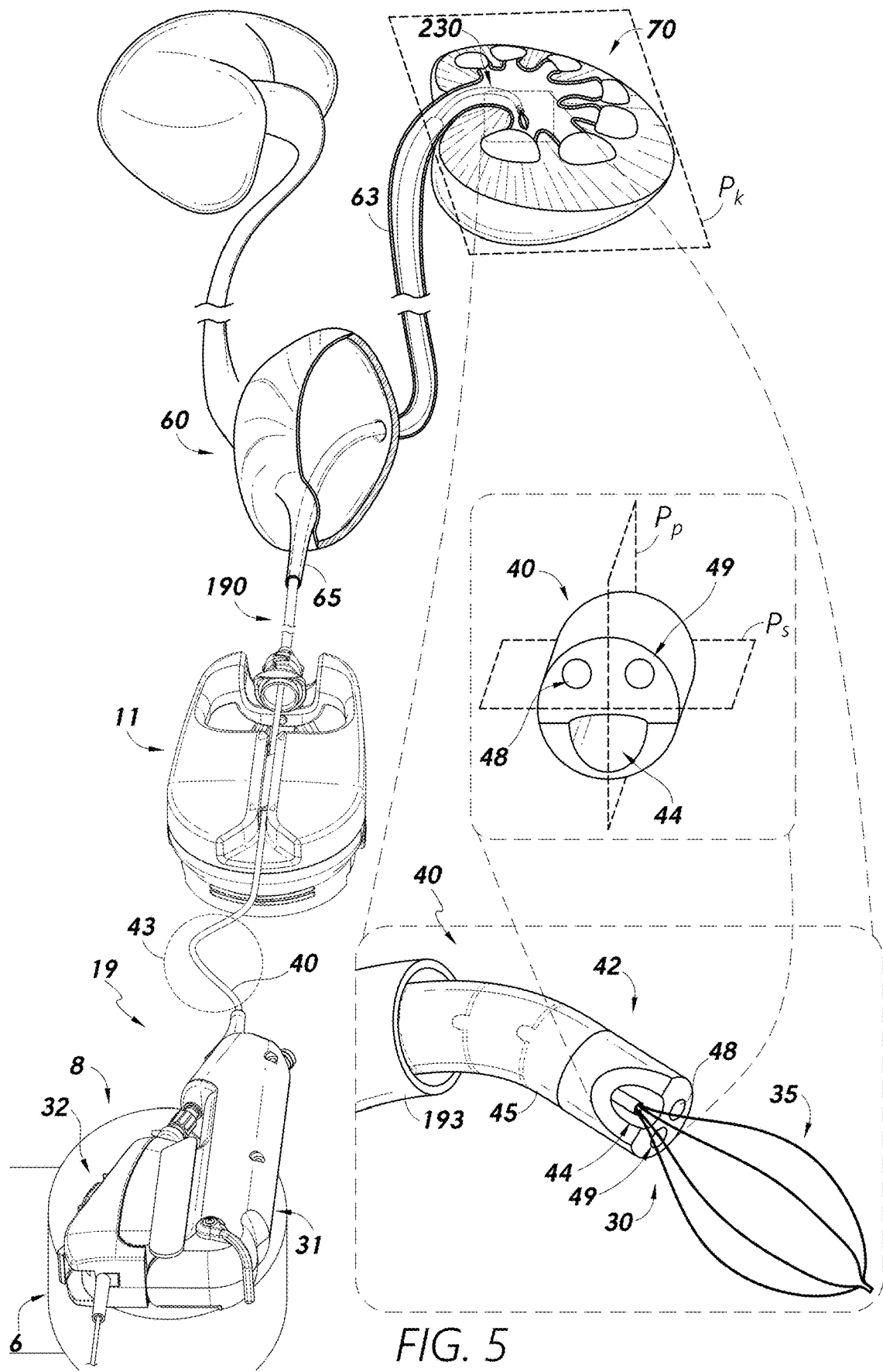
FIG. 5 illustrates a shaft-type instrument disposed in portions of the urinary system of a patient in accordance with one or more embodiments.

FIG. 5 illustrates a ureteroscope 40 disposed in portions of the urinary system of a patient in accordance with one or more embodiments. As referenced above, ureteroscopic procedures can be implemented for investigating abnormalities in human ureters and/or treating the same. For example, ureteroscope procedures can be implemented to treat and/or remove kidney stones. Such procedures may be implemented manually at least in part and/or may be performed using robotic technologies at least in part. For example, use of robotic devices and/or systems for certain endoscopic procedures can provide relatively greater precision, control, and/or coordination compared to strictly manual procedures. In some embodiments, the scope 40 includes a working channel 44 for deploying a basketing device 30 (e.g., basket component 35) to an operative region at a distal end of the scope 40.

The scope/shaft (e.g., endoscope/ureteroscope) 40 may comprise a tubular and flexible medical shaft/instrument that is configured to be inserted into the anatomy of a patient to capture images of the anatomy and to perform certain tasks using one or more working channels thereof. In some embodiments, the scope 40 can accommodate wires and/or optical fibers to transfer signals to/from an optical assembly and a distal end 42 of the scope 40, which can include an imaging device 48, such as an optical camera. The scope 40 can further include a light source 49, such as an LED or fiber-optic light source/lens.

The scope shaft 40 can be advanced to the target location through an access sheath 190. The access sheath 190 may be advanced through the ureter 63 to a position near the renal pelvis 71 and/or ureteropelvic junction 71. The distal end of the access sheath 190 may be parked at a position in the ureter 63 and/or renal pelvis 71. The access sheath 190 may be placed as far into the renal anatomy as possible, as permitted by the urinary tract path, which may be somewhat tortuous in certain portions thereof. Generally, the access sheath 190 may not be articulable to the degree that the scope 40 can be articulated, and therefore it may not be practical to navigate/drive the access sheath 190 into the kidney.

The scope 40 can be articulable, such as with respect to at least a distal portion 230 of the scope 40, so that the scope 40 can be steered within the human anatomy. In some embodiments, the scope 40 is configured to be articulated with, for example, six degrees of freedom, including XYZ coordinate movement, as well as pitch, yaw, and roll. Certain position sensor(s) (e.g., electromagnetic sensors) of the scope 40, where implemented, may likewise have similar degrees of freedom with respect to the positional information they generate/provide.

For robotic implementations, robotic arms of a robotic system can be configured/configurable to manipulate the scope 40. For example, an instrument device manipulator (e.g., scope handle) can be coupled to an end effector of a robot arm and can manipulate the scope 40 using elongate movement members. The elongate movement members may include one or more pull wires (e.g., pull or push wires), cables, fibers, and/or flexible shafts. For example, the robotic end effector may be configured to actuate multiple pull wires (not shown) coupled to the scope 40 to deflect the tip 42 of the scope 40. Pull wires may include any suitable or desirable materials, such as metallic and non-metallic materials such as stainless steel, Kevlar, tungsten, carbon fiber, and the like. In some embodiments, the scope 40 is configured to exhibit nonlinear behavior in response to forces applied by the elongate movement members. The nonlinear behavior may be based on stiffness and compressibility of the scope, as well as variability in slack or stiffness between different elongate movement members.

The camera/imaging device 48 can be used to capture images of an internal anatomical space, such as internal calyces of the kidney 70. The scope 40 may further be configured to accommodate optical fibers to carry light from proximally-located light sources, such as light-emitting diodes, to the distal end 42 of the scope. In some embodiments, the scope 40 is configured to be controlled by a robotic system similar in one or more respects to the robotic systems 100, 101, and 104 shown in FIGS. 1, 2, and 3, respectively.

In some embodiments, the shaft (e.g., scope) 40 includes a sensor that is configured to generate and/or send sensor position data to another device or produce a detectable distortion or signature in an electromagnetic field. The sensor position data can indicate a position and/or orientation of the medical instrument 40 (e.g., the distal end 42 thereof) and/or can be used to determine/infer a position/orientation of the medical instrument. For example, a sensor (sometimes referred to as a "position sensor") can include an electromagnetic (EM) sensor with a coil of conductive material or other form/embodiment of an antenna.

Embodiments of the present disclosure relate to the implementation of robotically-controlled shaft roll and the locking of shaft roll functionality when the instrument is undocked from the robotic system. Such robotic shaft roll can be restricted to a limited angle of rotation, which can prevent instrument damage. When a medical instrument and/or handle thereof is unlatched, undocked, or otherwise decoupled from a robotic end effector and/or adapter (e.g., sterile adapter) component associated therewith, the medical instrument and/or handle may be considered to be "off-robot," whereas when the medical instrument and/or handle thereof is latched, docked, or otherwise coupled to a robotic end effector and/or adapter (e.g., sterile adapter) component associated therewith, the medical instrument and/or handle may be considered to be "on-robot."

The instrument base/handle 31 can be configured to attach, mount, or otherwise be connected or coupled to the robotic end effector 6. For example, a robotic arm can include an instrument drive mechanism/assembly comprising an end effector and/or sterile adapter and the instrument base/handle 31 can be attached to the instrument drive mechanism/assembly. The instrument drive mechanism can include drive outputs configured to engage with and actuate corresponding drive input(s) on the instrument base/handle 31 to manipulate the medical instrument 19. For example, one or more drive outputs of the robotic end effector 6 can be configured to control shaft roll, as described in detail herein. The drive outputs of the end effector can be coupled to one or more drive couples of an adapter (e.g., sterile adapter) that are configured to transfer drive torque from the drive output(s) of the end effector to drive output(s) of the adapter. References herein to a robotic end effector and/or drive output(s) or other features thereof can be understood to refer to an adapter (e.g., sterile adapter) coupled to an end effector and/or drive output(s) of the adapter. For example, description of docking of an instrument on an end effector should be understood to refer to docking the instrument on an adapter when an adapter is coupled to the end effector.

In some configurations, the elongated shaft 40 of the medical instrument 19 is arranged to form a service loop 43 between the instrument handle 31 and the instrument feeder 11 and/or between the associated robotic arms. The service loop 43 may comprise a length of the shaft 40 between the instrument base/handle 31 and the feeder device 11. When the length of the shaft 40 exceeds the distance $D_a$ (see FIG. 1) between the instrument base/handle 31 and the feeder device 11, the shaft 40 may hang down (and/or to the side), forming the service loop 43 between the instrument base/handle 31 and the feeder device 11. The service loop 43 can provide slack in the shaft 40 that can be used to allow for faster insertion and/or retraction of the shaft 40. For example, during insertion, the slack in the service loop 49 can be taken up (shortening or contracting the service loop 49). During retraction, the service loop 49 can be generated (increasing in length or expanding).

The scope 40 can be deflectable in one or two directions within a first/primary plane $P_p$. The scope 40 can also be deflectable in one or two directions in a second/secondary plane $P_s$, which may be orthogonal to the primary plane $P_p$. For example, it can be desirable for the at least the distal section 230 of the scope 40 to be deflectable in more than one plane to reach the desired area, such as the specific anteriorly or posteriorly pointing calyx. Although the primary $P_p$ and secondary $P_s$ deflection planes are shown in a particular configuration, it should be understood that the illustrated secondary plane $P_s$ may be the primary plane $P_p$ and vice versa.

In some embodiments, the scope 40 comprises a distal articulation section 230. One or more cables, pull wires, or pull wire segments can run along the outer surface of the shaft 40. Additionally, the one or more cables can run along a central lumen of the shaft 40. Manipulation of the one or more cables results in actuation or deflection of the articulation section 230. Manipulation of the one or more cables can be controlled via one or more instrument drivers positioned within or connected to the instrument base/handle 31.

The instrument base/handle 31 can generally include an attachment interface having one or more mechanical inputs (e.g., receptacles, pulleys, spools, female inputs, etc.) that are designed to be reciprocally mated with one or more torque couplers on an attachment surface of an instrument driver. The instrument handle 31 can include a plurality of drive inputs. The plurality of control cables can be coupled to the plurality of drive inputs and extend along the flexible shaft 40. The plurality of drive inputs can be configured to control or apply tension to the plurality of pull wires or control cables in response to drive outputs from the medical robotic system.

In order to navigate the scope 40 through the anatomy, the articulation section 230 of the scope 40 can be deflectable in in the primary plane $P_p$. A distal section of the articulation section 230 may further be deflectable in two directions within the secondary plane $P_s$. Therefore, the distal portion of the articulation section 230 can be deflectable in two planes and four directions (e.g., left/right and up/down). The bend radius of the scope 40 may be greater in the primary plane $P_p$ (e.g., up to 270° or more in either direction) than in the secondary plane $P_s$ (e.g., 180° or less in either direction). Therefore, it may be desirable for the primary plane $P_p$ to be aligned with the plane of the kidney $P_k$ in order to maximize the reach of the articulation portion 230 of the scope 40 within the calyx network of the kidney 70. The physician may seek to achieve such alignment manually through manual manipulation of the handle 31 prior to docking on the end effector 6. After manual alignment, the physician may dock the handle 31 on the end effector 6, which may result in a roll/rotation of the shaft by about, for example, 90°. Embodiments of the present disclosure allow for compensation for such out-of-alignment rotation/roll through robotic roll control, which may be performed automatically after docking of the handle 31 in some implementations.

Robotic roll control in accordance with aspects of the present disclosure can involve rotation of the elongate shaft 40 relative to the instrument handle 31 about the longitudinal axis of the elongate shaft 40, at least at the proximal end thereof. Description herein or shaft roll/rotation about an axis thereof should be understood to refer to rotation of the shaft about an axis thereof at least at a proximal end or portion of the shaft. The rotation of the shaft 40 relative to the handle 31 can be operable to align the shaft 40 within the plane $P_k$ of the kidney, which may be an inferior-superior plane of the patient. For example, although the kidney 70 can be variable in shape, size, and configuration, it is roughly generalizable as a generally planar structure with an upper, middle, and lower pole. From each of these poles stem a series of calyces that point anteriorly or posteriorly.

The scope 40 can be rotated/rolled to align the articulation section 230 with the direction of the target calyces.

Figure 6:
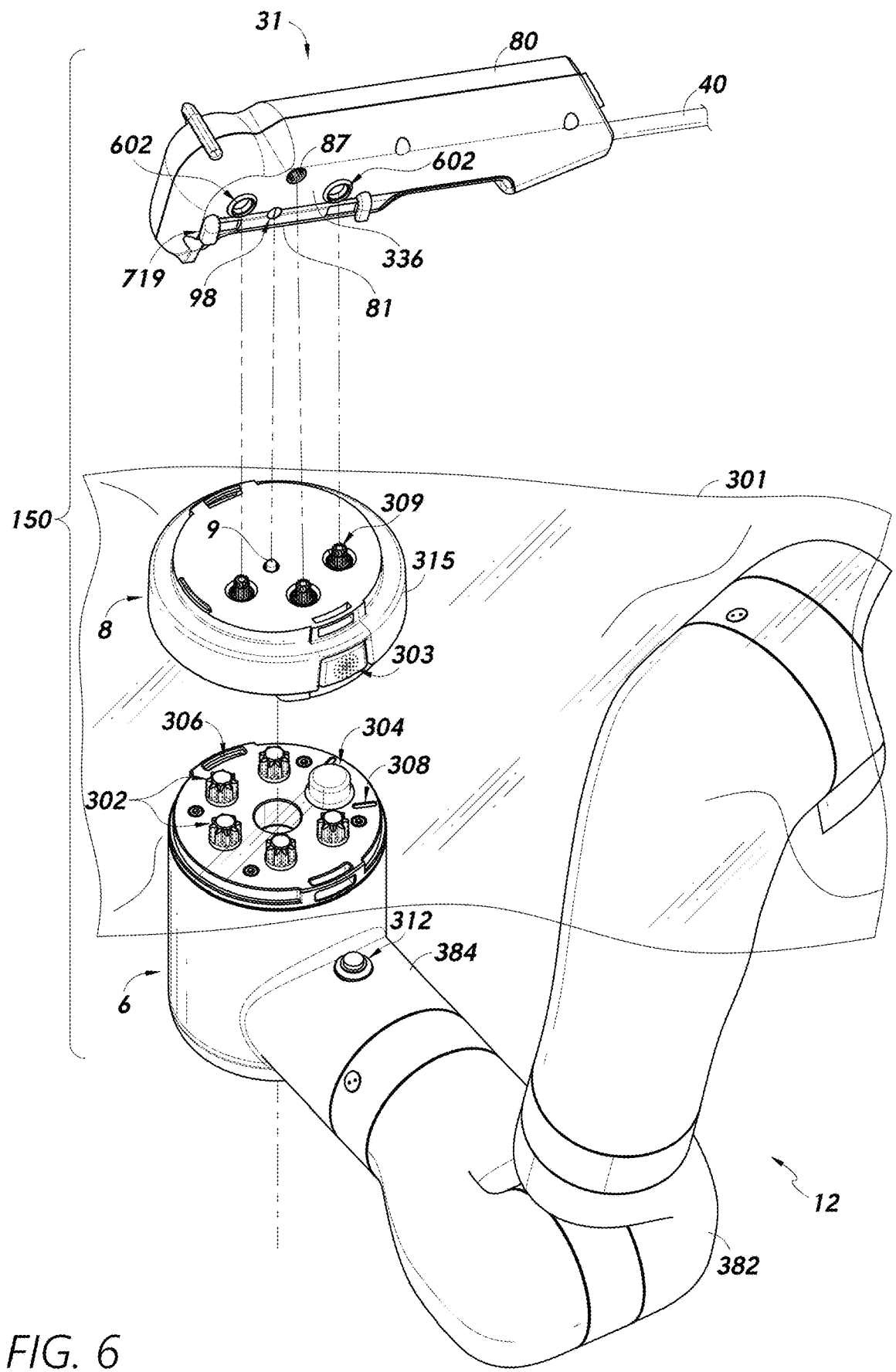
FIG. 6 shows an exploded view of an instrument manipulator assembly associated with a robotic arm in accordance with one or more embodiments.

FIG. 6 shows an exploded view of an instrument device manipulator assembly 150 associated with a robotic arm 12 in accordance with one or more embodiments. The instrument device manipulator assembly 150 includes an end effector 6 associated with a distal end of the robotic arm 12. The instrument manipulator assembly 150 further includes a handle 31 of a shaft-type instrument 19. The instrument handle 31 can incorporate mechanical (and/or electrical) means for rolling/rotating a shaft component associated therewith, such as an endoscope or other shaft-type instrument. Description herein of upward-facing and downward-facing surfaces, plates, faces, components, and/or other features or structures may be understood with reference to the particular orientation of the instrument device manipulator assembly 150 shown in FIG. 6, as assembled (rather than the tilted, exploded orientations shown). That is, although the end effector 6 may generally be configurable to face and/or be oriented in a range of directions and orientations, for convenience, description of such components (and components/devices attached/latched thereto directly or indirectly) herein may be in the context of the generally vertical facing orientation of the end effector 6 shown in FIG. 6.

In some embodiments, the instrument device manipulator assembly 150 further includes an adapter component 8 that is mountable to the end effector 6 and configured to provide a driver interface between the end effector 6 and the instrument handle 31. The adapter 8 and/or the instrument handle 31 may be removable or detachable from the robotic arm 12 and may be devoid of any electro-mechanical components, such as motors, in some embodiments. This dichotomy may be driven by the need to sterilize medical instruments used in medical procedures and the inability to adequately sterilize expensive capital equipment due to their intricate mechanical assemblies and sensitive electronics. Accordingly, the instrument handle 31 and/or adapter 8 may be designed to be detached, removed, and interchanged from the end effector 6 (and thus the system) for individual sterilization or disposal. In contrast, the end effector 6 need not be changed or sterilized in some cases and may be draped (e.g., using drape 301) for protection.

In some embodiments, the adapter 8 can include connectors to transfer pneumatic pressure, electrical power, electrical signals, and/or optical signals from the robotic arm 12 and/or end effector 6 to the instrument handle 31. The robotic arm 12 can advance/insert or retract the coupled instrument handle 31 into or out of the treatment site. In some embodiments, the instrument handle 31 can be removed and replaced with a different type of instrument. The end effector 6 of the robotic arm 12 can include various components/elements configured to connect to and/or align with components of the adapter 8, instrument handle, and/or shaft 40. For example, the end effector 6 can include drive outputs 302 (e.g., drive splines, gears, or rotatable disks with engagement features) to control/articulate a medical instrument, a reader 304 to read data from a medical instrument (e.g., radio-frequency identification (RFID) reader to read a serial number from a medical instrument), one or more fasteners 306 to attach the instrument handle 31 and/or adapter 8 to the end effector 6, marker(s) 308 to align with an instrument that is manually attached to a patient (e.g., access sheath) and/or to define a front surface of the device manipulator assembly 150. In some embodiments, a portion (e.g., plate) 315 of the adapter 8 can be configured to rotate/spin independently of one or more other components of the adapter 8 and/or end effector 6 when coupled to the end effector 6. The adapter 8 can include one or more outputs 309 configured to mate/couple with corresponding input(s) 602 of the handle 31.

In some configurations, a sterile drape 301, such as a plastic sheet or the like, may be disposed between the end effector 6 and the adapter 8 to provide a sterile barrier between the robot arm 12 and the instrument handle 31. For example, the drape 301 may be coupled to the adapter 8 in such a way as to allow for translation of mechanical torque from the end effector 6 to the adapter 8. The adapter 8 may generally be configured to maintain a seal around the actuating components thereof, such that the adapter 8 provides a sterile barrier itself. The use of a drape 301 coupled to the adapter 8 and/or more other component(s) of the device manipulator assembly (i.e., "robotic manipulator" or "robotic manipulator assembly") 150 may provide a sterile barrier between the robotic arm 12 and the surgical field, thereby allowing for the use of the robotic cart associated with the arm 12 in the sterile surgical field. The end effector 6 may be configured to be coupled to various types of sterile adapters that may be loaded onto and/or removed from the end effector 6 of the robotic arm 12. With the arm 12 draped in plastic, the physician and/or other technician(s) may interact with the arm 12 and/or other components of the robotic cart (e.g., screen) during a procedure. Draping may further protect against equipment biohazard contamination and/or minimize clean-up after procedure.

The instrument handle 31 can include a plurality of drive inputs 602, 87 on a lower surface 336 of the housing 80 of the instrument handle 31. In the illustrated embodiment, the instrument handle 31 includes three drive inputs 602, 87, although other numbers of drive inputs can be included in other embodiments. The drive inputs can be in fixed positions spaced apart along the lower mating surface 336 of the instrument handle 31, which facilitates coupling the drive inputs 602, 87 to the corresponding drive outputs 302 of the end effector 6, which may be in fixed positions spaced apart along a corresponding mating surface designed for modular use and attachment to a variety of other instruments. The handle 31 can include latching clips 719 or other latching features/means for physically coupling to corresponding structure of the adapter 8 and/or end effector 6.

A mechanical assembly within the instrument handle 31 can allow the drive inputs 602 to be used to drive articulation of the shaft 40, whereas the drive input 87 can be used to drive roll of the shaft 40. Each of the drive inputs 602, 87 can be configured to engage with a corresponding drive output 302 on the end effector 6. For example, each drive input can comprise a receptacle configured to mate with a drive output that is configured as a spline. The drive inputs and drive outputs can be configured to engage to transfer motion therebetween. Thus, the drive outputs can be rotated to cause corresponding rotation of the drive inputs to control various functionality of the instrument handle 31.

References herein to an "instrument device manipulator assembly," "instrument manipulator assembly," "manipulator," "manipulator assembly," as well as other variations thereof, can refer to any subset of the components of the assembly 150 shown in FIG. 6, including a robot arm, an end effector of a robot arm, an adapter configured to be coupled to a robotic end effector, an instrument base/handle configured to be coupled to an end effector and/or adapter, and/or other actuator component(s), means, and/or mechanism associated with an instrument base/handle. Furthermore, it should be understood that references herein to an "actuator" can refer to any component of the assembly 150 shown in FIG. 6 that affects or causes, either directly or indirectly, movement of an instrument/component engaged with, coupled to, or otherwise actuatable by, a component of the assembly 150. For example, in accordance with embodiments disclosed here, an "actuator" may comprise any set or subset of the following devices or components: feed roller(s), shaft-actuating wheel(s)/roller(s), feed roller channel(s), instrument feeder drive input(s), adapter drive output(s), adapter drive input(s), pulleys, belts, gears, pegs, pins, end effector drive output(s), and/or structures and/or control circuitry configured to cause actuation of the same. For example, an actuator may be any component, device, or structure configured such that movement thereof causes corresponding movement in another component, device, or structure, whether integrated with or separate from the actuator.

Figure 7A:
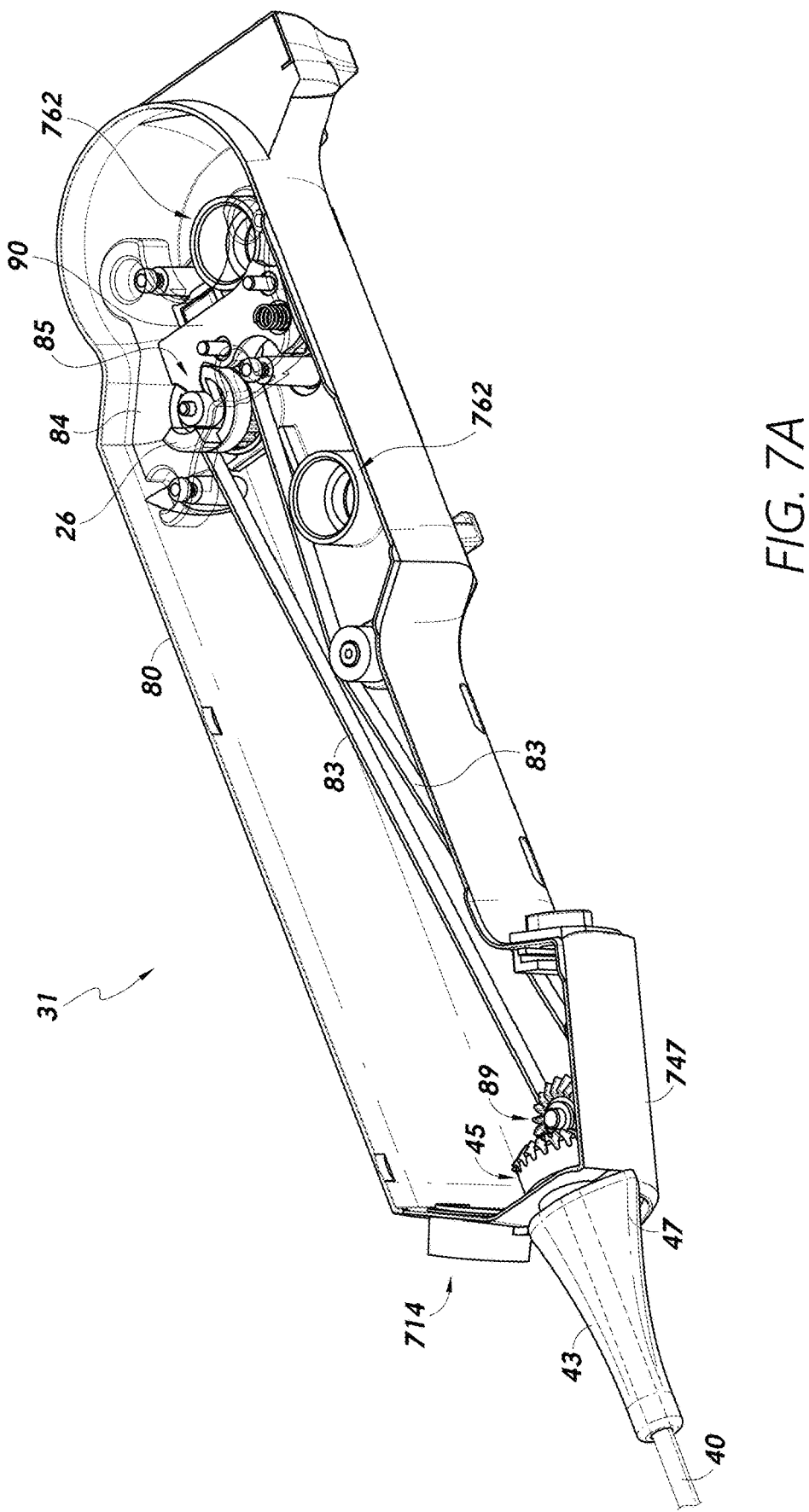
FIGS. 7A and 7B show cut-away perspective views of an instrument handle in accordance with one or more embodiments.
Figure 7B:
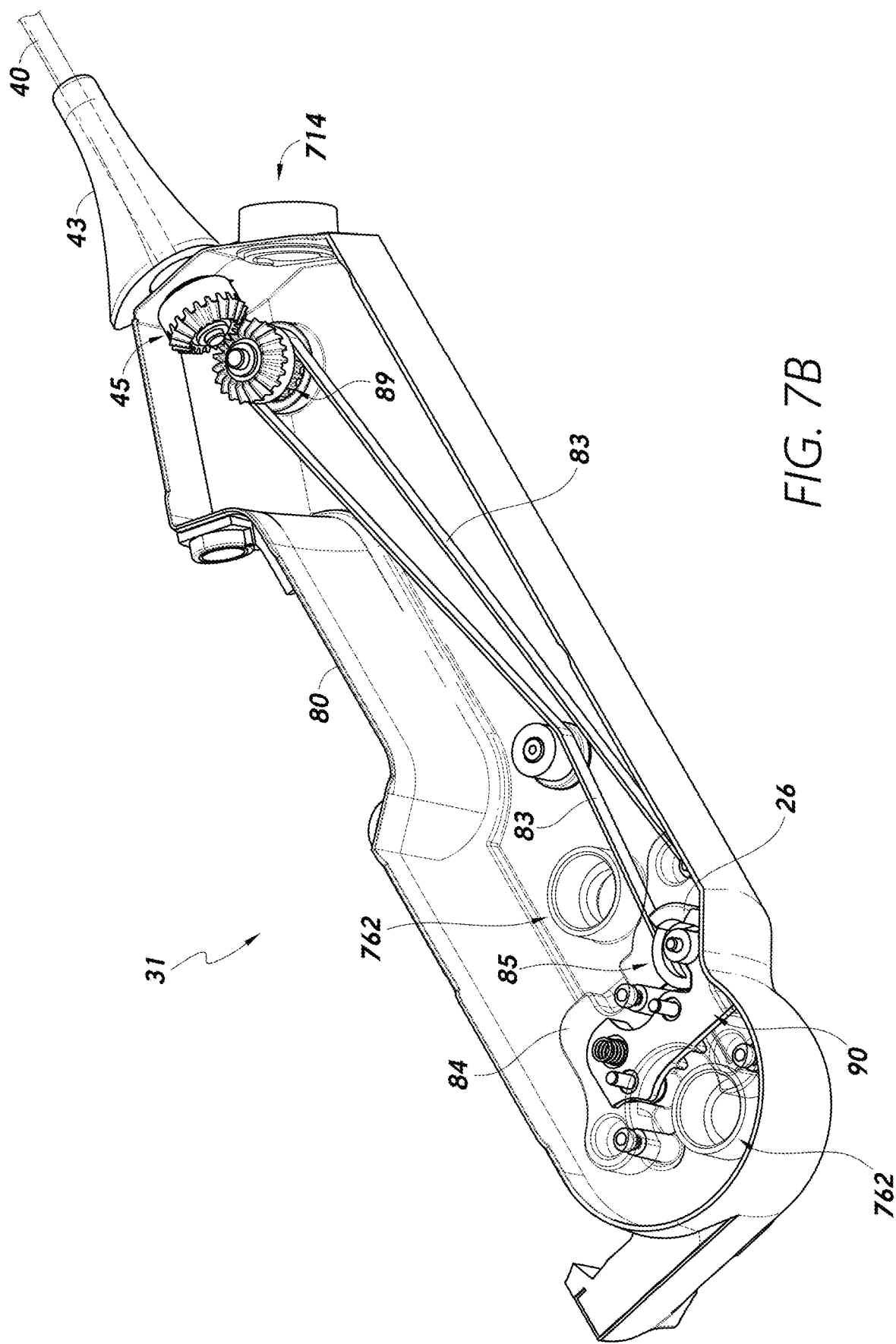

FIGS. 7A, 7B show cut-away perspective views of an instrument handle configured to implement robotic shaft roll in accordance with one or more embodiments of the present disclosure. Unlike certain solutions in which shaft roll is limited to manual rolling of the shaft and/or handle, some embodiments of the present disclosure advantageously allow for robotic shaft roll control, which may be implemented using one or more mechanical gears and/or other rotation-translation means/mechanisms.

The handle 31 has associated therewith one or more mechanism(s) that allows the shaft 40 of the instrument to be rolled/rotated robotically. For example, such mechanism(s) can be configured to transmit rotation of a robotic end effector output drive to the handle/base 31, and further to a base (e.g., proximal end) 45 of the shaft 40 via a belt 83 or other rotation translator component(s). In some embodiments, a bevel gear or other angle-transform gear/component 89 may be attached to the belt 83, and thereby to at least one of the roll axle/gear 85 and/or the shaft gear 45. The bevel gear 89 may convert the rotation of the axle/belt gear 85 by 90°, or some other angle, to allow for mesh engagement with the shaft gear 45 to rotate the shaft gear 45, thereby rolling the shaft 40.

The proximal end of the elongated shaft 40 extends from the instrument handle/base 31. In some embodiments, the elongated shaft 40 comprises a flexible shaft and/or an articulating shaft. As described above, pull wires (not shown) can be included in or on the handle 31 and elongate shaft 40 to control articulation of the elongate shaft 40. The handle 31 is configured to allow both manual control and robotic control of the shaft 40. For example, the instrument handle 31 can be configured to be physically held and manually manipulated to provide manual control, and to couple to an instrument drive mechanism to provide robotic control. In some embodiments, a sterile adapter can be positioned between the handle 31 and the instrument drive mechanism (e.g., robotic end effector or other robotic manipulator) to maintain a sterile field during a medical procedure.

As illustrated, the instrument handle 31 includes a housing 80, which may contain one or more of the roll control components/mechanisms described herein. The housing 80 of the instrument handle 31 can be shaped to provide an ergonomic fit for the instrument handle in a hand of a user/practitioner and/or for allowing for coupling thereto of another instrument. For example, the housing 80 shape can allow the instrument handle 31 to be more easily or comfortably held during manual control, such as for manually rolling the shaft 40 according to aspects of the present disclosure. Furthermore, the housing 80 shape can provide access to (e.g., not block) one or more robotic drive outputs associated with an adapter and/or end effector to which the handle 31 is physically coupled/latched for use by another instrument/device (e.g., basketing or lasing cartridge). The instrument handle 31 can include a power access port 714 for connecting to a power unit to power the one or more instruments (e.g., internal control circuitry) of a medical instrument system. The power access port 714 can be configured to provide electrical and/or visual connections to the shaft 40.

In some embodiments, the instrument handle 31 includes a manual roll input controllable by the shaft strain-relief form 43. In some embodiments, the elongate shaft 40 extends through the shaft outlet strain-relief form 43 and into the housing 80 of the handle 31. The shaft outlet strain-relief form 43 can be configured to allow the elongated shaft to rotate relative to the instrument handle 31. As illustrated, the shaft outlet strain-relief form 43 can be a twistable or rotatable handle or grip that can rotate relative to the housing 80. For example, the shaft strain-relief form 43 can rotate in a clockwise and/or counterclockwise motion. The shaft 40 can be rotationally fixed relative to the shaft outlet strain-relief form 43, such that rotation of the shaft strain-relief form 43 causes rotation of the shaft 40. Rotation of the shaft 40 can be in the same direction and equal/commensurate to corresponding motion of the strain-relief form 43, although this need not be the case in all embodiments. The shaft 40 may be permitted to rotate (e.g., roll) in both rotational directions by at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, or at least 360 degrees. Such roll may be limited by roll axle rotation limitation feature(s)/mechanism(s) described in detail below with respect to FIGS. 10-1, 10-2, 10-3, and 10-4.

The strain-relief feature 43 may comprise a rubber or other at least partially elastic/flexible material in the shape of a tapered cone, as shown. Such a cone may have a circumferential apex 47, which may provide a visual indication and or manual/tactile engagement feature that indicates a roll position of the shaft 40. For example, the apex 47 may rotate about the axis of the shaft as the shaft rotates. The form of the cone, such as may be provided at least in part by the apex feature, can provide a manipulation surface for manual manipulation by the user to manually rotate the shaft 40. Generally, alignment of the apex 47 of the cone 43 with, for example, a side portion 747 or other portion of the handle 31 can be associated with the shaft 40 being rotationally aligned in a home (e.g., zero/locked) position. In some embodiments, the apex 47 may be aligned with a camera and/or working channel of the shaft 40. In some embodiments, visual indication of the roll position of the shaft 40 may be indicated by one or more other visual markers in addition to the apex and/or as an alternative thereto. For example, a band, notch, or other visual marking(s) on the shaft 40, strain-relief form, and/or side 747 or other portion of the handle 31 may indicate a roll orientation of the shaft 40.

With reference to FIGS. 6, 7A, and 7B, the handle 31 can include a plurality of robotic drive inputs 87, 602 (not shown in FIGS. 7A, 7B; see FIG. 6), which may be accessible via one or more input ports 762. The robotic drive outputs of the end effector and/or adapter (see FIG. 6) can engage and transfer torque to (e.g., rotate) the robotic endoscope drive inputs 87, 602. For example, the drive input 87 may be associated with the roll axle 85. Any of the drive inputs may be rotatable in both the clockwise and counterclockwise directions. The drive inputs 87, 602 can be configured as grooved or keyed recesses and can be configured to engage robotic drive outputs 302 (see FIG. 6) that are configured as protruding/projecting splines. The robotic drive outputs 302 can be driven by motors to rotate in clockwise and counterclockwise directions. When the robotic drive outputs are engaged with the respective robotic endoscope drive inputs, the robotic drive outputs may generally transfer rotational motion to the robotic endoscope drive inputs. Each of the drive inputs 602 and input ports 762 may be associated with one or more pulley, gears, and/or other mechanism(s) configured to cause articulation of the shaft 40.

The orientation of the shaft 40 may be rotated about 90° in the process of manually docking the handle 31 on an end effector 6 and/or adapter 8. When manually rolling the shaft 40, the physician may hold the handle 31 and rotate the entire handle to cause the desired rotation/roll of the shaft 40 to align the plane of articulation $P_p$ of the shaft 40 with the plane of the kidney $P_k$ (e.g., plane generally bisecting the calyx network). When the instrument handle 31 is docked to the robotic end effector 6, embodiments of the present disclosure may include a mechanism to align the plane of articulation $P_p$ of the shaft 40 with the plane of the kidney $P_k$, wherein such alignment may compensate for and/or be necessitated at least in part by the rotation of the handle 31 for the purpose of docking to the end effector 6.

Robotic shaft roll may be achieved by a first bevel gear 89 and a second bevel gear 45. That is, in some embodiments, the shaft gear 45 may be a bevel gear. The first bevel gear 89 can be coupled to the robotic drive input 87 and/or roll axle 85, such that rotation of the drive input 87 and/or roll axle 85 causes rotation of the first bevel gear 89. The first bevel gear can serve as an angle-transform gear for transforming a torque/rotation axis of the gear 89, roll axle 85, and/or roll drive input 87 to an axis that is parallel and/or co-axial with the base of the shaft 40 and/or shaft gear 45. The shaft gear 45 (e.g., bevel gear) can be attached to the proximal end of the shaft 40 such that rotation of the shaft gear 45 can cause rotation of the elongate shaft 40 relative to the instrument handle 31.

The first and second bevel gears 89, 45 can be engaged/meshed to transfer rotational movement of the roll axle 85 to the shaft 40. For example, as shown, a drive belt 83 or other rotation translator means/mechanism may be used to operatively couple the first bevel gear 89 to the roll axle 85 from a distance. The roll axle 85 and drive input feature 87 thereof, or associated therewith, may be proximal of the angle-transform bevel gear 89, and may be disposed between the shaft articulation inputs 602/762 in some embodiments. Other methods and mechanisms for transferring rotational motion of the roll axle 85 to the shaft 40 are also possible. In some embodiments, as the shaft 40 is rolled, the internal components (e.g., one or more coil pipes, pull wires, electrical wires, and/or fiber optics) may be inclined to twist due to fixation to both the proximal and distal ends of the shaft 40. Twisting of the internal components can occur throughout much of the length of the elongate shaft 40, minimizing the resultant force/torque applied to the proximal and distal terminations thereof.

With further reference to FIGS. 7A and 7B, as well as FIG. 5, implementation of shaft roll in accordance with aspects of the present disclosure may be desirable as a means or mechanism for aligning a deflection plane of the shaft 40 with the plane $P_k$ of a kidney 70. For example, it may be desirable for a primary deflection plane $P_p$ associated with the shaft 40 to be aligned with the plane $P_k$ of the calyx network of the kidney 70. Furthermore, shaft roll can be implemented to align a working channel 44 of the shaft 40 in a position that facilitates utilization of a working instrument disposed within the working channel 44. That is, as shown in the detailed image of FIG. 5, the working channel 44 may generally not be at an axial center of the shaft 40, but rather may be radially offset to one side, at least in part. Therefore, if the working channel 44 is misaligned, the ability to utilize an instrument disposed therein for an intended purpose may be constrained. Generally, the plane $P_k$ of the kidney 70 may correspond to a bisectional plane of the kidney, as shown in FIG. 5. However, it should be understood that based on the particular patient anatomy, one or more of the calyces may be slightly off-plane. However, such calyces may be accessible from a position from the primary plane $P_k$ of the kidney. Alignment of the primary deflection plane $P_p$ of the shaft 40 with the plane $P_k$ of the kidney can advantageously provide a maximum/high degree of reach of the shaft 40 within the kidney.

As described above, in some embodiments, the shaft 40 may be configured such that articulation thereof in one or more planes may be implemented. For example, in some embodiments, the shaft 40 may be configured to articulate in a primary deflection plane $P_p$ in an amount greater than 180°, such as about 270° or more, whereas the scope can articulate in a secondary deflection plane $P_s$ to a degree that is equal to or less than the degree to which the shaft 40 can articulate the primary articulation plane $P_p$. For example, the shaft 40 may be configured to articulate only up to 90° or less in one or more planes in some embodiments. Shaft roll control in accordance with aspects of the present disclosure can advantageously allow for robotic alignment of the primary articulation plane $P_p$ of the shaft 40 with the area of the calyces within the calyx network to allow for navigation to target kidney stone(s) or other specimen(s) to be extracted. Such described articulation in the primary $P_p$ and secondary $P_s$ plane(s) may advantageously be in both/two directions within the given articulation plane. Generally, the degree of deflection/articulation in a given deflection plane of the shaft 40 may be limited based on the amount of freedom that the individual structural links of the articulation portion 230 of the shaft 40 provide. In some embodiments, a proximal portion of the shaft 40 at, within, and/or near the handle 31 is configured to bend in only 2 directions, whereas a distal portion of the shaft 40 may be configured to bend in 4 directions, or vice versa.

In some implementations, after some amount of manual rotation/manipulation, the handle 31 may be placed on a robotic manipulator 6 (see FIG. 6). In such transition between the manual held position and the docked position on the end robotic manipulator (e.g., effector 6 and/or adapter 8), the orientation of the instrument handle 31 and/or shaft 40 may be rotated by about 90°, such that the shaft 40 rolls an amount that is commensurate with the rotation of the handle 31. Therefore, robotic roll adjustment may be desirable after docking of the handle 31 in some cases. For example, the system control circuitry may be configured to drive the relevant actuators/mechanics of the handle 31 to roll of the shaft 40 to compensate for the 90° (or other) change in shaft roll resulting from the docking of the handle 31. Such automatic roll correction may be based at least in part on the position of the patient. Although automatic shaft roll correction is described, it should be understood that such shaft roll correction may be implemented by the operator using certain user input controls (e.g., control device 55 in FIG. 1), as described herein.

Figure 8:
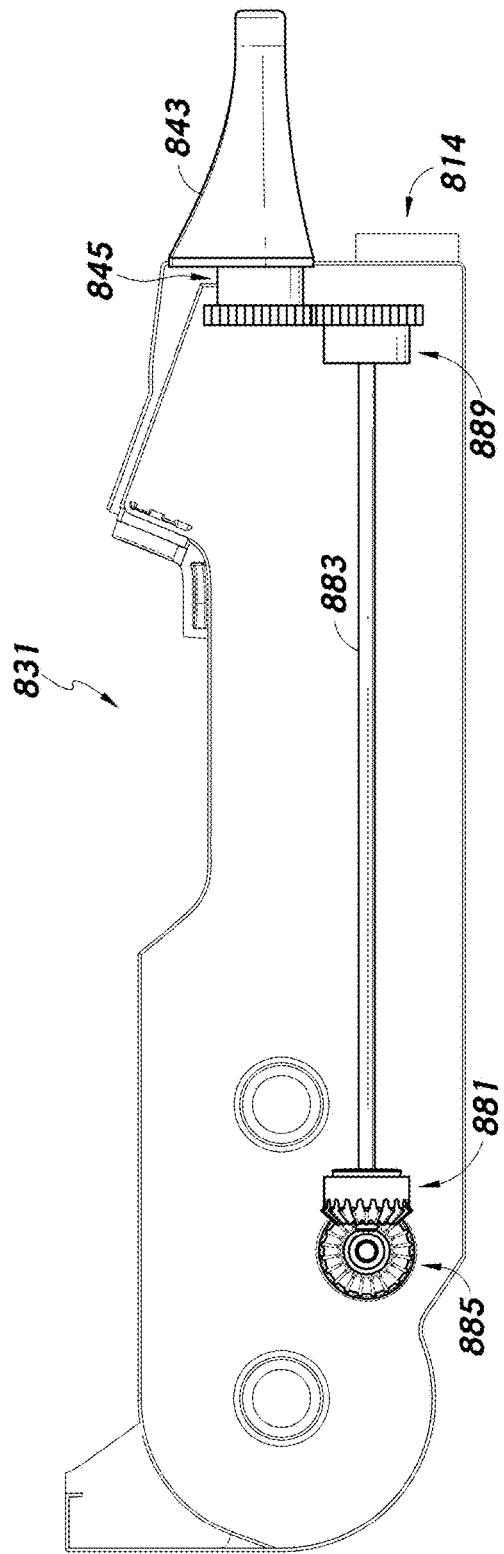
FIG. 8 shows a cut-away view of an instrument handle in accordance with one or more embodiments.

FIG. 8 shows a cut-away view of an instrument handle 831 in accordance with one or more embodiments of the present disclosure. The embodiment of FIG. 8 provides an alternative rotation translation mechanism compared to the embodiment of FIGS. 7A and 7B for translating rotation of a roll axle 885 of a handle 831 with a shaft base/gear 845. For example, the embodiment of FIG. 8 shows an axle-based transmission of rotational force from the roll axle 885 and associated output drive of the robotic end effector/adapter to which the handle 831 is coupled to the shaft hear 845, wherein rotation of the axle 885 transmits rotation to a transverse-axis rod 883 via a bevel gear 881 or other angle-transform gear.

The rotation translation mechanism of FIG. 8 includes a direct-drive rod 883, which may be mechanically coupled to the roll axle 885 via a mesh engagement between the roll axle 85 and the bevel gear 881 coupled to the rod 883. The rod 883 can be coupled to a distal shaft-actuating gear 889. Generally, compared to a belt or other solution, the use of a rod for driving the shaft roll can advantageously provide relatively less loss. That is, a higher percentage of rotation of the driving gear(s) 885, 881 may generally be translated to a working gear 845 than with respect to certain other solutions, such as certain belt-type solutions.

The distal drive gear 889 and the shaft gear 845 may be spur gears in some embodiments. In some embodiments, the proximal drive gear 881 is a bevel gear configured to allow for meshing of the proximal drive gear 881 with a bevel-type roll axle 885, wherein the roll axle 885 is orthogonal/transverse relative to the proximal drive gear 881. Implementing spur gears for one or more of the roll axle 885, proximal drive gear 881, distal drive gear 889, and/or shaft gear 845 can be desirable due to the relatively secure meshing of teeth of spur gears relative to bevel gears in some cases. That is, positioning and engagement of bevel gears may require relatively greater precision compared to spur gears due to the tendency thereof to bind and/or split. Therefore, use of spur gears for one or more of the gears of the device can provide a higher degree of freedom with respect to position and/or angle of the gears compared to bevel gears and/or other solutions.

The distal drive gear 889 may advantageously be positioned in a location that allows for a distal cable (e.g., power cable/wire(s)) to pass thereby and through the port 814. Compared to a belt-type roll control system as shown in FIGS. 7A and 7B, a cable or rod-based mechanism may have less play/give, but may be relatively more difficult to install and/or assemble. Furthermore, for a belt-based system, such system may be more or less inclined to lose tension over time.

Figure 9:
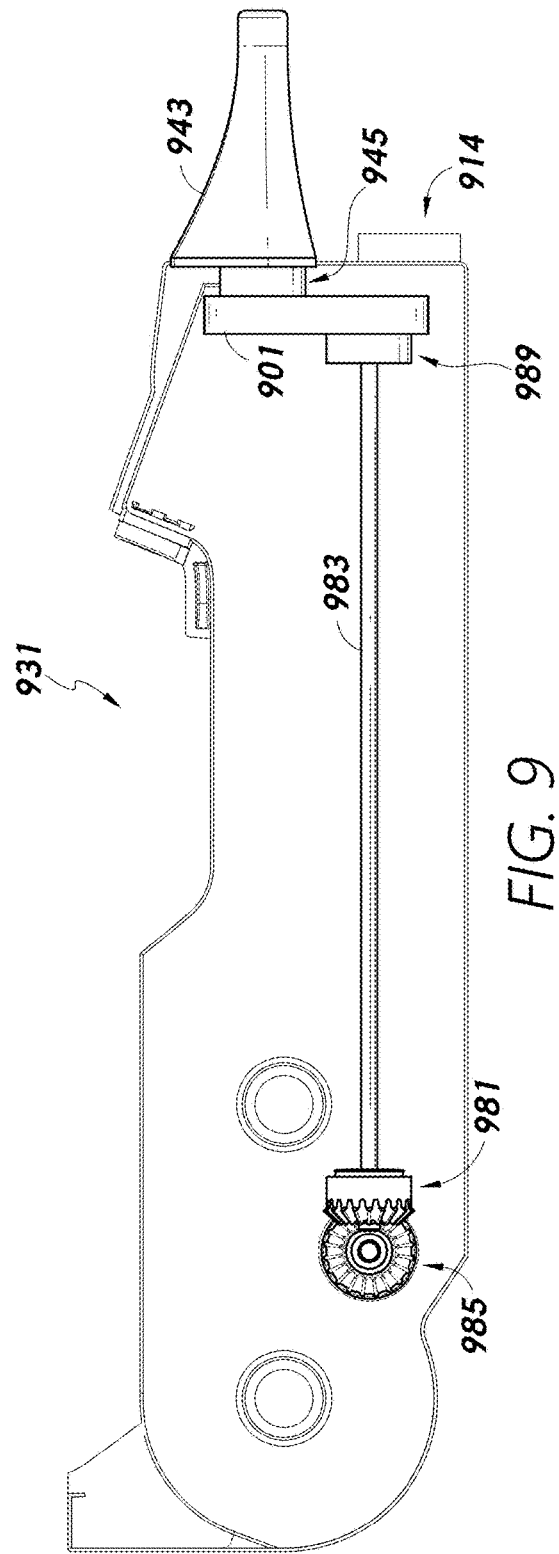
FIG. 9 shows a cut-away view of an instrument handle in accordance with one or more embodiments.

FIG. 9 shows a cut-away view of an instrument handle 931 having a rod-based rotation translation mechanism, which may be similar in certain respects to the embodiment shown in FIG. 8, in accordance with one or more embodiments of the present disclosure. In the embodiment of FIG. 9, the distal drive gear 989 is configured to transmit rotation of the rod 983 to the shaft gear 945 via a belt 901 or other rotation translator engaged with both of the gears 989, 945.

Figures 4, 10:
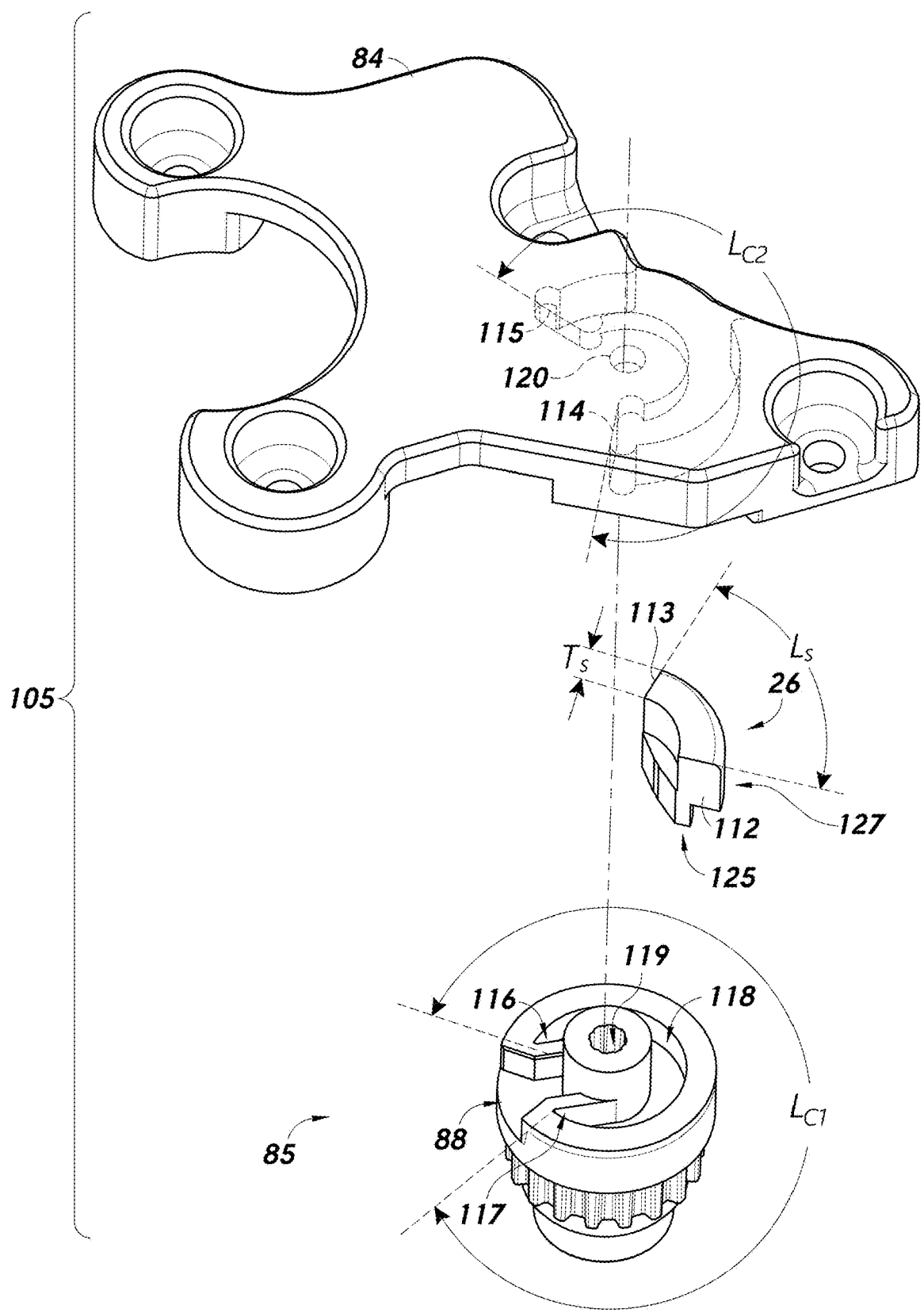

FIG. 10 shows a cut-away perspective view of an instrument handle 31 including a roll axle assembly. FIGS. 10-1, 10-2, and 10-3 show perspective views of the roll axle assembly 105 of the instrument handle 31 in accordance with one or more embodiments of the present disclosure. FIG. 10-4 shows an exploded view of the roll axle assembly 105 shown in FIGS. 10-1, 10-2, and 10-3. The roll axle assembly 105 includes a roll axle 85, which may represent an embodiment of any of the roll axles disclosed herein. The roll axle assembly 105 includes the roll axle 85, as well as a rotation-limiting slider component/portion 26, and an axle-retention structure 84 having certain rotation-limitation features according to aspects of the present disclosure.

Generally, a full 360°, or more, of rotation of a shaft of a medical instrument in either/both direction(s) (i.e., clockwise and counterclockwise) may be desirable. However, with respect to robotically controlled shaft roll, it may not be desirable to permit infinite roll, as such rolling beyond 360° can cause damage to wires and other components associated with the shaft from twisting due to over-rolling. Therefore, it may be desirable to limit the rotation of the axle 85 in order to avoid twisting and/or damage of/to certain pull wires, camera wires, and/or other wires, cables, or other components that may emanate from the proximal end of the shaft and/or shaft gear. That is, it may be desirable to limit the rotation of the axle 85 to prevent the axle 85 and/or shaft gear 45 from rotating more than about 360° in either direction (e.g., less than 720° in total rotation).

Limitation of rotation of the axle 85 may be achieved using an open annular channel 118 of the axle 85 and/or an open annular channel 111 of the axle-retention structure 84, wherein such channels may be open towards one another in some embodiments. Although annular channels are shown as being associated with both the axle 85 and the retention structure 84, it should be understood that axle rotation limitation may be implemented using an annular channel in either, but not both, of the axle 85 and retention structure 84. For example, the axle 85 may generally be a rotating component, whereas the axle-retention structure 84 may generally be a static/stationary component, wherein rotation of the axle 85 in one or both directions may be stopped by direct or indirect contact between a stopper contact surface/face 116, 117 of the axle 85 that is exposed within the channel 118 and a stopper contact surface/face 114, 115 of the axle-retention structure 84 that is exposed within the annular channel 111 of the retention structure 84. Such contact between the axle 85 and the axle-retention structure 84 may be made indirectly via the slider structure/component 26, which may translate contact within the annular channel 118 of the axle 85 to the contact surface(s) 114, 115 of the annular channel 111 of the sensor-retention structure 84. For example, the slider 26 may include a lower engagement feature 125 configured to fit at least partially within the annular channel 118 of the axle 85 and slidably move therein. The slider 26 may further include an upper engagement feature 127 configured to fit at least partially within the annular channel 111 of the axle-retention structure 84 and slidably move therein.

The rotation of the axle 85 may be limited by contact with the slider 26 on either annular end thereof with stopper surfaces of the axle and the axle retention structure, respectively. For example, such stopper surfaces may be exposed within the open annular channels 111, 118 of the axle 85 and axle-retention structure 84, respectively. That is, as the axle 85 rotates in a given direction, the lower portion 125 of the slider 26 may be configured to sit within the open annular channel 118 of the axle 85 and may slide within the channel until it contacts a stopper surface of, and exposed within, the channel 118. With the slider in contact with the stopper surface within the open annular channel 118 of the axle 85, the axle may be permitted to continue to rotate until the upper portion 127 of the slider 26 reaches a hard stop against a stopper surface of, and exposed within, the channel 111 of the axle-retention structure 84.

The slider 26 can advantageously extend the rotation range of the axle 85 through sliding movement within the annular channel 111 of the sensor-retention structure 84. For example, when rotating the axle 85 in a given direction, such rotation may be stopped by a hard stop caused by contact surfaces of the slider 26 and axle channel 118 coming into contact with one another, wherein, after contacting the stopper surface of the axle channel 118 and after further rotation of the axle in the same direction, a contact surface on an opposite end of the slider may also come into contact with a hard stop surface of the open channel 111 of the axle-retention structure 84. As an example use case, FIG. 10-1 shows the roll axle 85 at its furthest permitted clockwise rotation. FIG. 10-2 shows the roll axle 85 rotated counterclockwise (compared to the configuration of FIG. 10-1) to a contact position with the an opposite end of the slider 26; a side 112 and/or inside 129 surface of the slider 26 in an area associated with the lower portion 125 of the slider 26 is in contact with the stopper surface 117 inside the channel 118 of the axle 85. In FIG. 10-2, the axle 85 can continue to rotate counterclockwise until the side surface 113 of the upper portion 127 of the slider 26 is stopped by the inside stopper contact surface 115 of the annular channel 111 of the retention structure 84, which configuration is shown in FIG. 10-3.

The slider 26 can advantageously extend the permitted rotation of the axle beyond the limits of the axle channel 118 by extending the effective contact of the axle 85 into the annular channel 111 of the axle-retention structure 84, and allowing the axle 85 to rotate an additional amount equivalent to the arclength $L_{c1}$ of the channel 111 minus the arc length $L_s$ of the slider 26. Therefore, the total amount of permitted rotation of the axle 85 may be about equal to (or proportional to) the sum, in degrees, of the arclength $L_{c1}$ of the axle channel 118 and the arclength $L_2$ of the retention structure channel 111, minus two-times the arclength $L_s$ of the slider; the arclength $L_s$ of the slider may need to be accounted for with respect to its space occupied in both the axle channel 118 and the retention structure channel 111. In some embodiments, while the axle channel 118 may allow for an amount of rotation that is less than 360°, the additional engagement of the slider 26 with the axle channel 111 of the retention structure 84 can extend the rotation range of the axle, even beyond 360°.

The annular/arc length $L_{c1}$ of the slider channel 118 of the axle 85 may be restricted at least in part by the presence of the mating feature/channel 88, which may provide a keyway/locking aspect/area for the axle 85, as described in detail below. That is, in some embodiments, the size of the mating feature/channel 88 occupies space that takes away from the usable annular length of the channel 118 of the axle 85.

The range of rotation of the roll axle 85 may be determined at least in part by the arclength $L_s$ of the slider 26. That is, the longer the arc length $L_s$ of the slider 26 with respect to the amount of annular length within the channel 118 of the axle 85 and the channel 111 of the retention structure 84 occupied by the respective portions of the slider, the smaller the range of rotation permitted.

Generally, the radial thickness $T_s$ and arc length $L_s$ of the slider 26 may be determined to provide a desired structural stability for the slider 26 with respect to the propensity of the slider 26 to bind within one or more channels and/or withstand hard stop forces against the respective stopper surfaces. For example, if the slider 26 is too narrow with respect to annular length $L_s$ and/or too narrow with respect to radial thickness $T_s$, breaking and/or sheering can result from hard stop forces thereon. However, such dimensions can limit the rotation of the axle 85 and/or require greater size/space. Therefore, the design of the slider involves a trade-off between structural stability and size. For example, it may be desirable to design the slider 26 to be relatively robust for the purpose of facilitating the sliding thereof within the annular channel 118 of the axle 85 and the annular channel 111 of the retention structure 84 and for providing convenient fit therein. Furthermore, relatively longer annular length $L_s$ of the slider 26 can facilitate sliding in the respective channels and reduce the risk of the slider 26 tipping over and binding or otherwise becoming askew within the channel(s).

The axle 85, slider 26, and retention structure 84 assembly 105 shown in FIGS. 10-1 through 10-4 provides a solution for increasing a rotation range of a rotation-limited axle that may be suitable in certain applications. Additional solutions may be implemented to increase rotation range of roll axles in connection with embodiments of the present disclosure, such as by varying the gear diameter(s) associated with one or more of the roll-control gears associated with the relevant handle/instrument. For example, reducing the gear diameter of a shaft gear associated with a proximal end of an instrument shaft can increase the permitted rotation of the shaft. Additionally, increasing the diameter of a distal drive gear can increase rotation of the shaft relative to rotation of the roll axle, thereby increasing an operable range of roll. The particular assembly shown in FIGS. 10-1 through 10-4 can be suitable for providing the desired shaft roll range in environments limited by space constraints, such as within a handle, as shown in various figures of the present disclosure.

In some implementations, embodiments of the present disclosure allow for a shaft-type instrument be used both manually and robotically. As may be desirable in such implementations, certain embodiments of the present disclosure relate to instrument handles configured to lock or fix shaft rotation in place automatically when the handle is manually manipulated. For example, such instrument handles may be configured such that when the handle is docked to a robotic end effector, rotation/roll of the shaft is automatically unlocked and allowed to be robotically controlled via the end effector (and/or attached adapter) and one or more components associated with the handle of the instrument. It should be understood that any reference herein to an end effector and/or component(s) or feature(s) thereof can refer to similar component(s) or feature(s) associated with an adapter coupled to an end effector, rather than to the end effector itself.

Figure 11A:
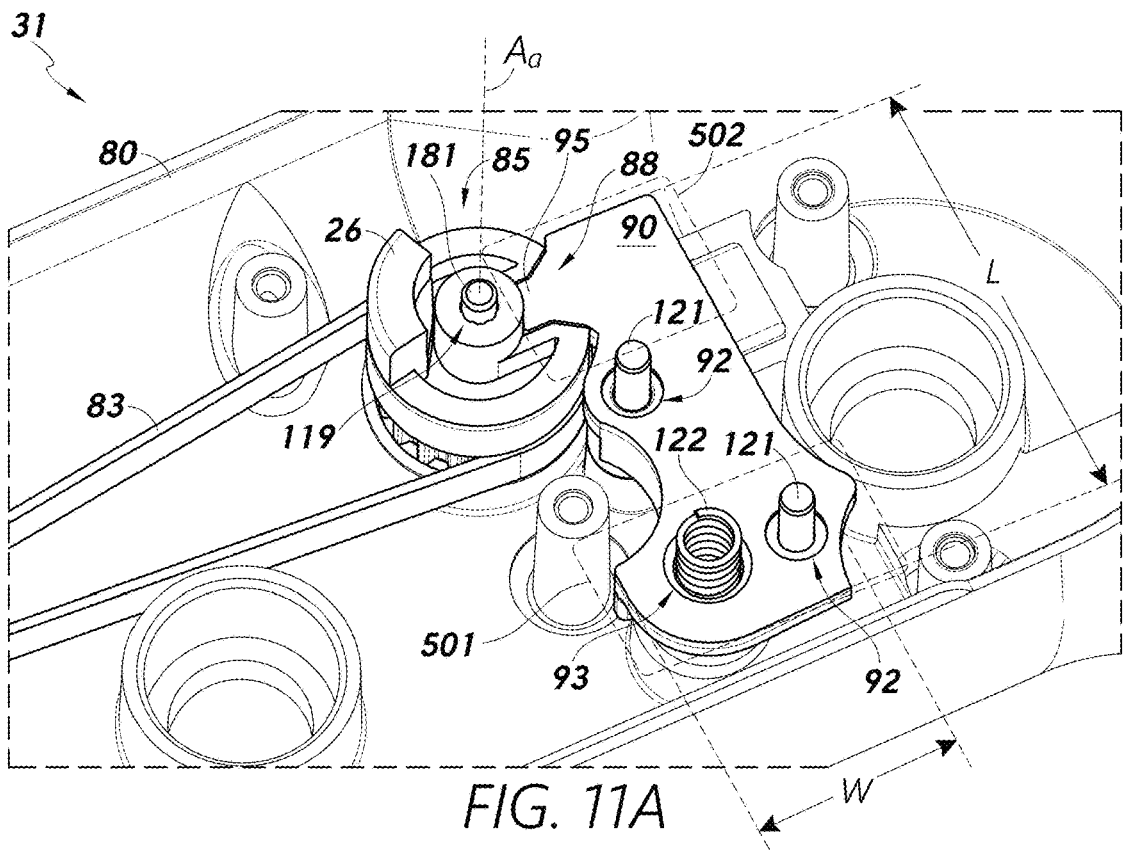
FIGS. 11A, 11B, and 11C show perspective views of certain instrument handle components, including an axle catch in a locked position, in accordance with one or more embodiments.
Figure 11B:
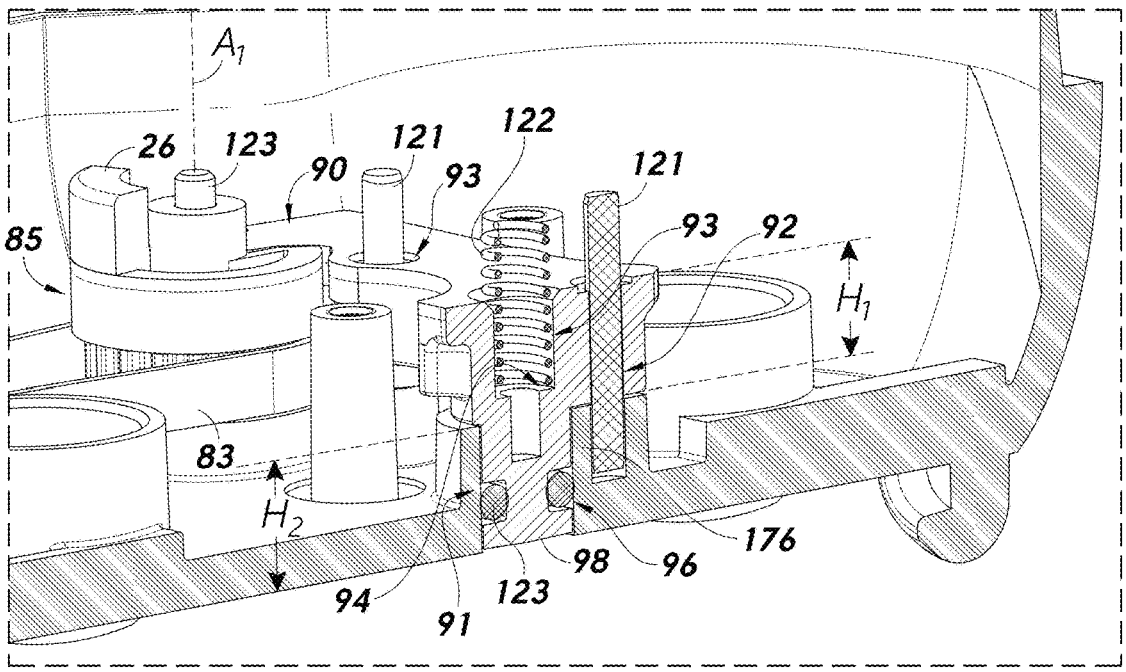
Figure 11C:
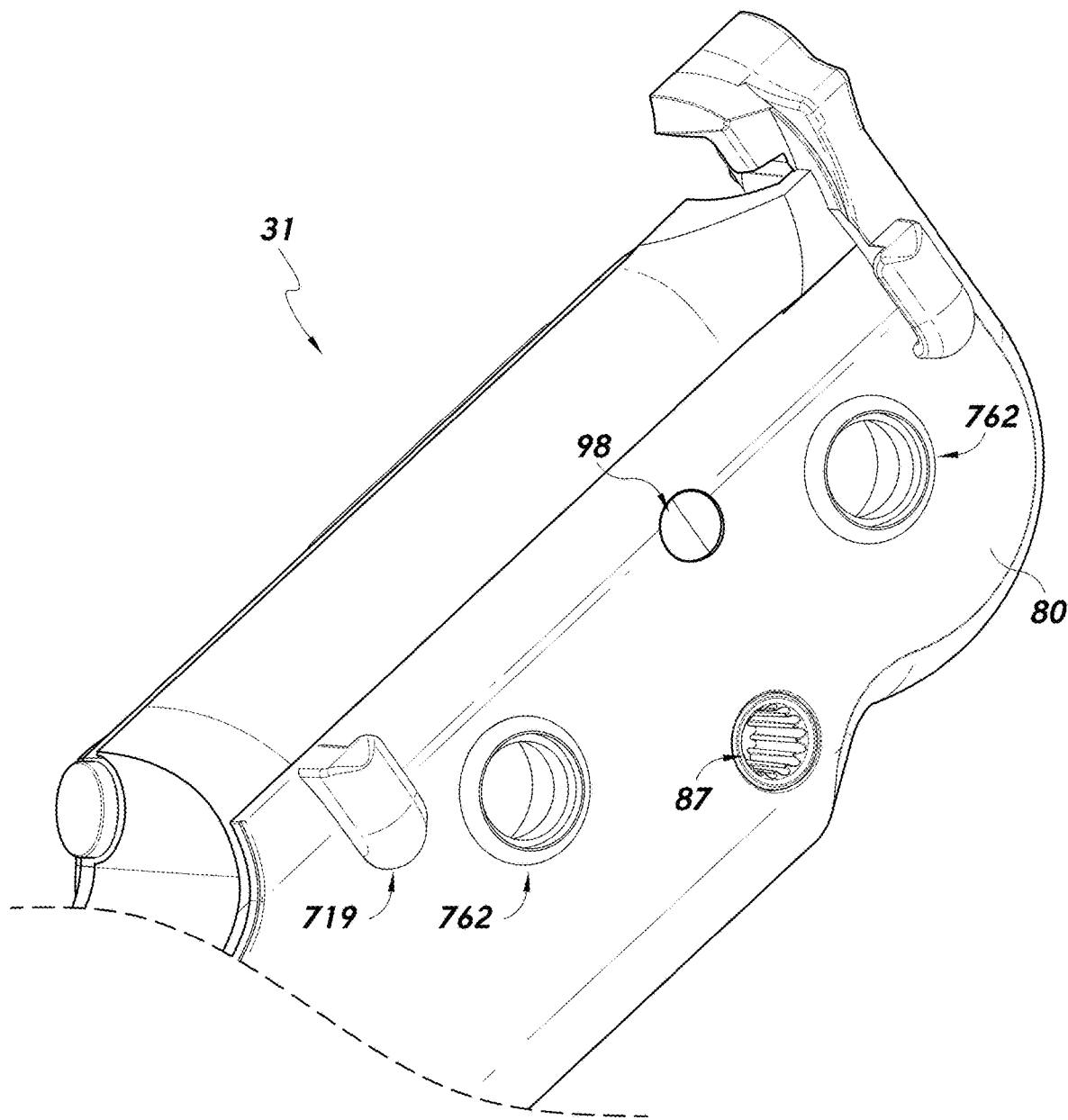
Figure 12A:
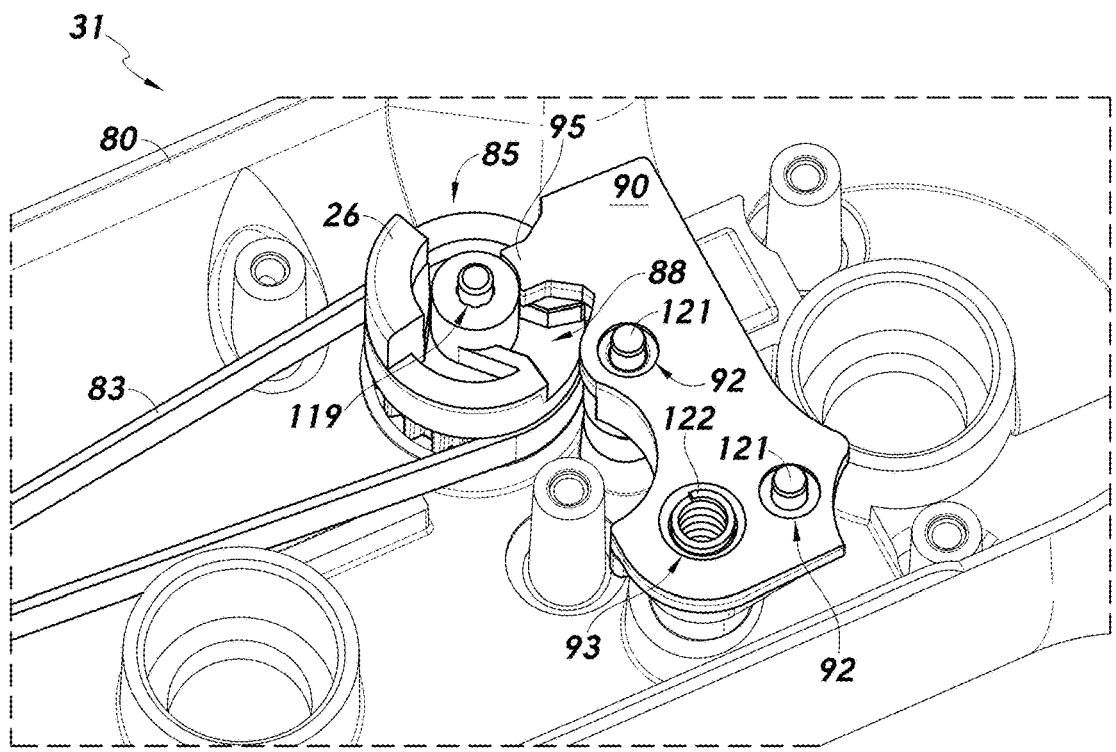
FIGS. 12A, 12B, and 12C show perspective views of certain instrument handle components, including an axle catch in an unlocked position, in accordance with one or more embodiments.
Figure 12B:
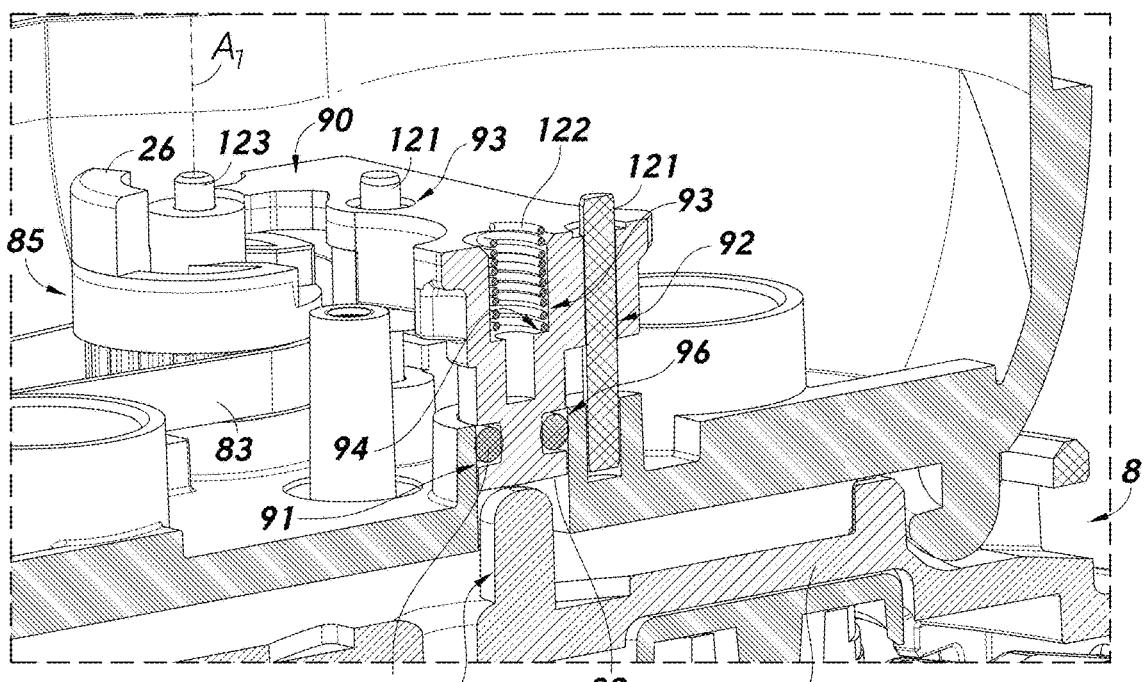
Figure 12C:
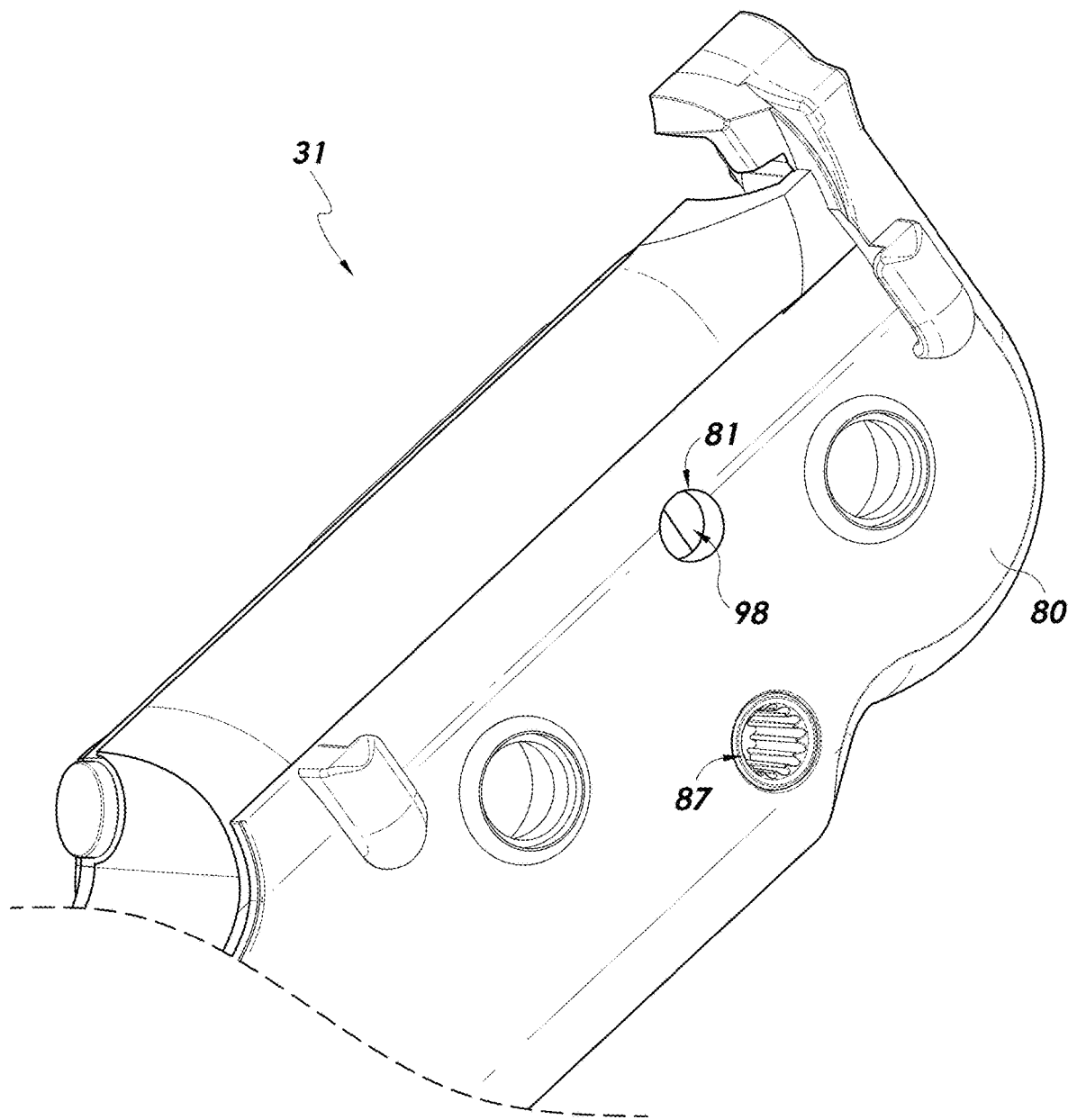

FIGS. 11A, 11B, and 11C show perspective views of certain instrument handle components, including an axle catch 90 in a locked position in which rotation of a roll axle 85 is limited/restricted by the axle catch 90, in accordance with one or more embodiments of the present disclosure. FIGS. 12A, 12B, and 12C show perspective views of the instrument handle components shown in FIGS. 11A-11C, wherein the axle catch is in an unlocked position in which an actuator-engagement boss 9 of an adapter or end effector device has engaged, and caused vertical translation of, the catch 90 to thereby lift/move the key feature 95 of the catch 90 out of the mating feature 88 of the roll axle 85, thereby allowing the roll axle 85 to freely rotate in response to drive input. Any of the description below may be understood with respect to FIGS. 11A-11C and/or 12A-12C.

As described above, in some cases, physicians or other operators/technicians may execute instrument shaft roll by holding a handle of an instrument in their hand and rotating their arm and/or hand to rotate the handle and shaft coupled thereto together as a unit. That is, with respect to any of the figures/embodiments of the present disclosure, when manually rolling a shaft 40 of an instrument 19, it may be necessary or desirable for the roll of the shaft 40 relative to the handle 31 thereof to be restricted/locked to allow rotation of the handle 31 to be translated to the shaft 40. Generally, implementation of hand-held manual roll/rotation may allow for about 180° of rotation, wherein such rotation is limited by the physical constraints of the arm and/or hand/wrist, which may vary to some degree across users.

The instrument handle 31 of FIGS. 11A-11C and 12A-12C includes a roll axle locking structure/catch 90 that may be configured to translate and key with the roll axle 85. The term "catch" is used herein according to its broad and ordinary meaning, and may refer to any type of locking, stopping, blocking, impeding, or interfering structure, which may be understood with respect to a rotating axle component, feature, or device. When the instrument is used manually, such that the handle 31 is manually held/manipulated by the user, a spring or other biasing feature 93 may bias the catch structure 90 towards the roll axle 85 in a manner as to engage a key component 95 of the catch 90 with a mating feature 88 (e.g., keyway) of the roll axle 85. For example, when the user manually rotates the shaft 40 (not shown in FIGS. 11A-11C) to align a meeting feature of the roll axle 85 with the key feature 95 of the axle catch 90, the biasing of the catch 90 towards the plane of the roll axle 85 can cause the key feature 95 to engage with the keyway mating feature 88, thereby locking the rotation of the roll axle 85 in place. In such a locked state, the shaft 40 may not be permitted to freely rotate and/or be actuated through robotic driving.

In FIGS. 11A-11B and 12A-12B, the roll axle 85 is rotated to a home/zero position in which the mating feature 88 is rotationally aligned with the key feature 95, such that the key feature 95 can move into and out of the mating feature 88. If the roll axle 85 is not in the home rotational position, which may be associated with a predefined angular position with respect to the shaft 40 about a roll axis thereof and/or the roll axle 85 about a rotational axis thereof, it may not be possible to implement shaft roll lock as described herein. Therefore, prior to latching or unlatching the handle 31 from the robotic system, it may be necessary or desirable to rotate the shaft 40 and/or axle 85 to the home position to enable shaft roll lock. For example, if the shaft 40 and/or axle 85 are rotated to the home position prior to unlatching/undocking of the handle 31, such unlatching/undocking may automatically cause the catch 90 to lock the axle 85. In some implementations, system control circuitry is configured to automatically roll the shaft 40 and/or axle 85 to the home position prior to undocking of the handle 31. In some implementations, unlatching/undocking may be restricted/locked unless and until the shaft 40 and/or axle 85 is/are in the home position. Whether the shaft roll is in the home position may be determined electronically and/or mechanically.

With reference back to FIG. 6, the robotic end effector 6 and/or adapter component 8 associated therewith may include a catch actuation boss 9 or other feature configured to depress an actuator feature 91 of the catch 90 when the handle 31 is docked on the end effector/adapter 8, wherein such actuator engagement can serve to disengage the lockout mechanism of the catch 90 by translating the key feature 95 of the catch 90 out of the mating feature (e.g., keyway) 88 of the axle 85. That is, by pushing the handle 31 down onto the adapter 8 to latch the handle 31 to the adapter 8, the catch-actuating projection/boss 9 may automatically press against the actuator contact surface 98 to dislodge/translate the axle catch 90 vertically (with respect to the orientation shown) from its locked position, removing the key 95 from the mating feature 88 of the axle 85. Therefore, embodiments of the present disclosure provide solutions that allow a user to unlock a shaft roll control mechanism associated with an instrument handle by docking the handle on an end effector and/or adapter 8 (or other type of robotic manipulator). In such unlocked state, the handle may be free to operate to cause the shaft of the instrument to roll in response to certain control signals and/or drive input.

The key feature 95 provides a locking feature for the axle 85. In some embodiments, the key feature 95 keys into the mating feature 88 of the axle 85 in a locked position in which rotation of the axle 85 is restricted. The fit of the key 95 in the mating feature 88 may advantageously be tight enough to prevent backlash/ejection of the key feature 95 when restricting roll/rotation of the axle, but not too tight to cause binding friction when actuating the catch into and/or out of mating engagement with the mating feature 88. For example, the catch actuator component 91 may be positioned at a separate end 501 of the catch 90 relative to the key feature 95, such that actuation of the catch actuator 91 (e.g., vertical translation thereof) may result in a tendency of the catch 90 to bind due to the uneven application of force to the catch 90. Therefore, some amount of clearance around the key feature 95 may be desirable. However, any amounts of clearance between the key feature 95 within the mating feature 88 may translate to allowable rotation of the axle 85 when the key 95 is in the locked position. Therefore, the key 95 may fit relatively snuggly within the mating feature 88 in some embodiments.

In some embodiments, with respect to an axis $A_a$ of the axle 85, the axle catch 90 may be configured to translate vertically in parallel with the axis $A_a$, such that the key 95 rises out of the mating feature 88. The axle-retention structure 84 (not shown in FIGS. 11A-11C and 12A-12B for clarity) can present a limit on how far the catch 90 can translate vertically. With reference also to FIGS. 10-1 through 10-4, the axle cover/retention feature 84 can serve to align the roll axle 85 with the drive input associated therewith. In some embodiments, a pin 181 is disposed in an axial cup 119 of the axle 85 and within a corresponding opposite-facing cup 120 of the axle-retention structure 84. Alternatively, the alignment pin 181 may be an integrated form with the cover 94. The pin 181 may advantageously allow for rotation thereabout by the axle 85.

The axle 85 may be biased in the locked position shown in FIGS. 11A-11C, wherein the axle catch 90 is positioned such that the key 95 is engaged with the mating feature 88 of the axle 85. In some embodiments, such biasing may be implemented using one or more springs 122 or other biasing features. For example, the spring 122 may push downward (with respect to the shown orientation) on the axle catch 90 to bias the key feature 95 down into the mating feature/channel 88. In some embodiments, the spring 122 presses against an underside/surface of one or more components of the handle housing, such as the underside of the axle-retention structure 84 or other structure. In some embodiments, the axle catch 90 includes a spring-retention feature 93, such as a cup or recess feature, as shown in FIGS. 11A and 11B. For example, the spring-retention feature 93 may have an open cylindrical form, with a seating 94 on which the spring 122 can apply biasing force. Although a cup-type spring retention feature is shown, it should be understood that any type of spring-retention form or structure may be implemented, such as an attachment means or mechanism for securing the spring 122 to the catch 90 (e.g., one or more hooks, clips, adhesives, or the like).

One or more alignment pins 121 may be utilized to facilitate translation of the catch 90 that is generally parallel with the axis $A_a$ of the axle 50. That is, the pin(s) 121 can be configured to control/guide the direction and/or orientation of travel of the catch 90 to thereby keep the catch 90 in-plane when translating (e.g., with respect to a flat top surface of the catch 90). For example, embodiments in which the biasing component (e.g., spring) 122 is disposed relatively close to one end 501 of the catch 90, the biasing force provided thereby may be inclined to cause the catch 90 to tip and/or bind when translating. The pins 121 may prevent/reduce such tipping/binding. In some embodiments, the catch 90 includes one or more apertures or other features 92 configured to have the pin(s) 121 disposed therein to provide a track/guide for the catch 90 about the pin(s) 121. The pin(s) 121 may be secured to the housing 80 in some manner, and may be integrated with other structure of the handle or may be separate components that are secured in place by being nested with one or more retention features of the housing and/or axle retention structure 84.

With reference also back to FIG. 6, the adapter component 8 includes a catch actuator engagement feature/boss 9, which is configured to engage with the actuator 91 when the handle 31 is latched to the adapter 8 and/or end effector 6. For example, when the handle 31 is latched/docked to the adapter 8 and/or end effector 6, the boss 9 can be configured to press against the engagement surface 98 of the actuator 91, thereby causing the catch actuator 91 and coupled/integrated catch 90 to translate in a direction generally parallel with an axis of the boss 9, actuator 91, and/or catch actuator access channel 176. By such means, the boss 9 may be configured to unlock the axle 85 by causing the catch 90 to translate such that the key 95 moves out of the mating feature 88 of the axle 85. Such unlocking may be performed from outside of the housing 30 of the handle 31. In some embodiments, the axle actuator 91 is axially aligned with the spring-retention cup 93, as shown in FIG. 11C.

In some embodiments, the catch actuator 91 (e.g., plug, pin, button, peg, plunger, or other actuator means or form) projects into and/or through the actuator access channel 176 of the handle housing 80. In some embodiments, the actuator 91 includes an annular gap or space 96, which may accommodate an O-ring or other type of sealing component configured to prevent fluid ingress into the handle housing 80 through the actuator channel 176. In some embodiments, the annular gap/channel 96 does not have a sealing feature disposed therein, but rather provides an airgap in which any fluid passing around the actuator periphery may generally collect in the gap space 96.

The catch 90 may have a height dimension $H_1$ corresponding to a height of an area of the catch including the alignment pin channels 92, wherein the height dimension $H_1$ provides surface area around the alignment pins 121 to facilitate alignment thereof and to keep the alignment channels 92 substantially parallel with the alignment pins. For example, it may be advantageous to prevent the catch 90 from being permitted to rock/tip when translating, wherein such inclination to rock/tip may be dependent at least in part on the height dimension $H_1$ and/or the clearance around the pins within the alignment channel(s) 92. Therefore, to reduce rocking/tipping, the alignment channel 92 may advantageously fit relatively closely around the alignment pins 121 with little clearance, while allowing some amount of clearance to avoid frictional restraint on the catch 90 around the pins when axially translating. Furthermore, the height of the catch $H_1$ in the area of the alignment channel(s) 92 may be made as great as possible in view of the relevant space constraints within the housing 80. For example, pulleys, wires, and/or other components of the handle 31 may be disposed at least partially above the catch 90 within the housing 80, wherein the catch 90 does not occupy such space during the unlocked or locked configurations. The topology of the underside of the catch 90 may advantageously fill available space within the housing 80 to provide one or more bearing surfaces in which the catch 90 contacts structural component(s) of the base of the housing 80 on bottom surface(s) thereof when the catch 90 is in the locked position to allow the catch 90 to rest in the locked position. The catch 90 may have a total height $H_2$ including the actuator 91 that is greater than the height $H_1$ of the body of the catch 90.

The actuator-engagement boss 9 of the adapter 8 (and/or end effector 6) may be limited in height to avoid contacting instrument components when other instruments other than the handle 31 are latched thereto. For example, the adapter 8 may be configured to have various types of instruments attached thereto, including catheter-type instruments and/or the like. In some embodiments, the pin has a height of about 2.2 mm, or less. In some embodiments, the pin is more than 2.2 mm tall.

The catch 90 may have a length dimension L and a width dimension W, as shown, wherein the length dimension L is greater than the width dimension W. For example, the width dimension W may generally be parallel with a projection dimension of the key 95, whereas the length dimension L may be transverse/orthogonal to the width dimension W. The ends 501, 502 of the catch 90 may be considered to be lengthwise halves or thirds of the catch 90; in some embodiments, the key 95 may be part of, or otherwise associated with, an opposite lengthwise side/end 502 of the catch 90 from the actuator 91 and/or the spring 122 and spring-retention cup 93. At least one alignment pin 121 and/or associated alignment pin channel 92 may be associated with a medial lengthwise portion of the catch 90 between the opposite ends 501, 502.

Although a single actuator peg/form 91, channel 176, and actuator boss 9 are shown and described above, it should be understood that the catch 90, housing 80, and/or adapter 8 may be implemented with any number of actuator, actuator access channel, and/or actuator pin components. For example, by including two catch actuators, the stability of the catch 90 during translation can be improved. For example, such multiple actuators and associated components/features may be associated with separate sides/ends 501, 502 of the catch 90, and/or between the ends/sides 501, 502. Generally, the position of the actuator 91 in the end region 501 may not be ideal from a translation alignment standpoint. However, due to certain physical/positional constraints associated with the handle housing 80, the configuration illustrated in FIGS. 11A-11C and 12A-12C may be necessary or desirable, wherein any alignment deficiencies presented by the position/location of the actuator 91 may be compensated for using one or more of the alignment pin channel(s) 92, spring-retention cup(s) 93, height/thickness dimensions $H_1$, $H_2$, and key-axle engagement features.

Figures 1, 13:
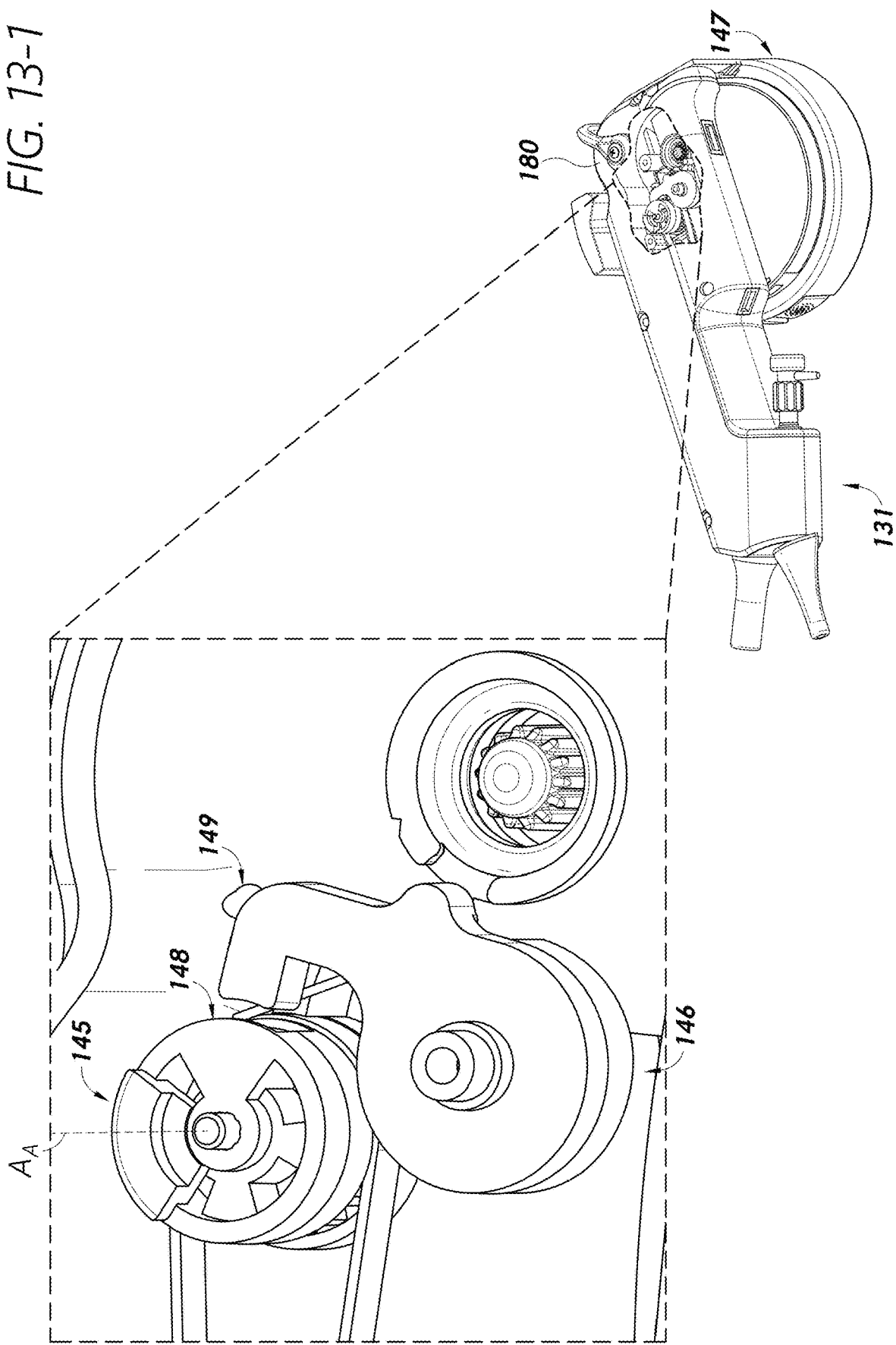
Figures 2, 13:
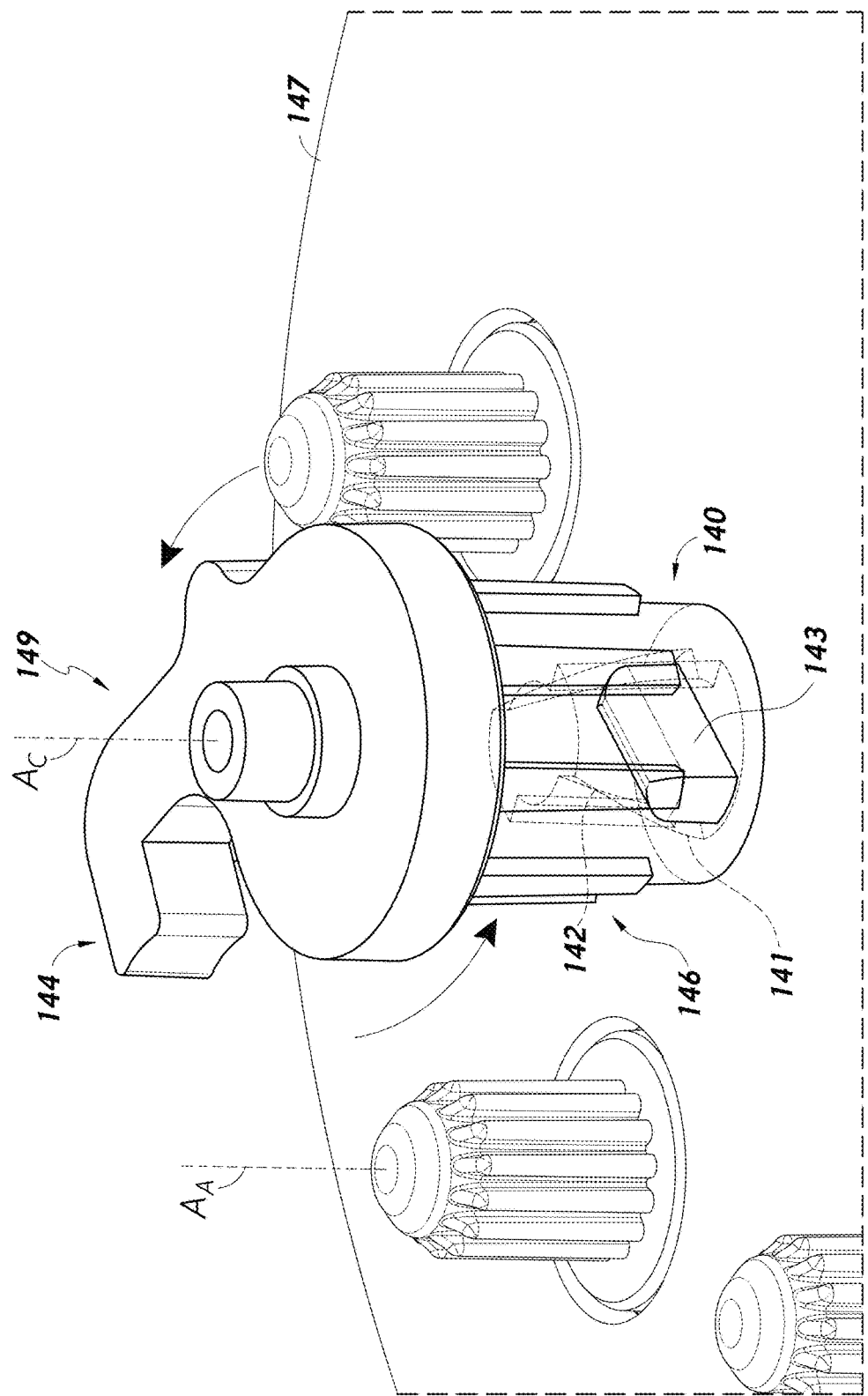

FIGS. 13-1 and 13-2 show perspective views of certain instrument handle components including an axle catch 146 in accordance with one or more embodiments. Compared to the embodiment shown in FIGS. 11A-11C and 12A-12C, use of a rotating catch rather than a vertically-translating catch can provide certain benefits. For example, with respect to vertically-translating catch structures, certain contaminants can become trapped within the actuator channel associated therewith, which may be relatively difficult to sanitize/clean.

For example, with respect to the plug-type actuator embodiment of FIGS. 11A-11C and 12A-12C, the area between the actuator contact surface 98 and the base of the actuator plug 91 may be difficult to clean and/or access. With respect to the rotating actuator of FIGS. 13A-13C, the actuator 140 thereof may not be prone to have contaminants pass around the actuator 140 due to the actuator merely rotating in place as opposed to physically translating along an axis and/or into the housing of the handle.

In some embodiments, the actuator 140 of the catch 146 is a cam actuator. In such a system, the adapter and/or end effector 147 to which the handle 131 is attached can include an actuator-engagement projection/boss 143, which can have any suitable or desirable shape or configured to actuate the cam socket 141 of the actuator 140. For example, the actuator-engagement projection/boss 143 may have a rectangular/oblong cross-sectional shape, as shown. By pushing the actuator-engagement projection/boss 143 into the cam socket 141, the angled/curved cam surfaces/grooves 142 of the cam socket 141 may cause the axle catch 146 to rotate about the axis $A_c$ of the actuator 140, thereby causing the bent projection 149 of the catch 146 rotate out of the mating feature 148 of the axle 145. The catch 146 may be biased in a locked position in which the end 144 of the bent projection 149 protrudes into the mating feature 148 associated with the side of the axle 145, thereby locking the rotation of the axle.

The catch 146 may be biased toward the roll axle 145 via a torsion spring or some other biasing device/mechanism, wherein the catch 146 is configured to automatically rotate away from the roll axle 145 when docked on the end effector and/or adapter associated therewith.

With respect to the cam actuator 140, the more aggressive the angle of the angled/curved cam surfaces/grooves 142, the more rotation is translated to the catch 146 per unit of distance projected into the cam socket 141 of the actuator 140 by the actuator-engagement boss 143, which may increase the probability that successful unlatching/unlocking may be achieved when the handle 131 is docked on the adapter/end effector 147. Generally, the actuator-engagement boss 143 may need to overcome the biasing force (e.g., spring force) in order to effect rotation of the cam catch 146.

The rotating axle catch 146 is configured to rotate to engage with the keyed feature 148 of the axle 145, rather than translating vertically to engage and disengage with/from the mating feature of the axle. Rotation may be achieved using a cam feature formed in the catch 146 and/or associated therewith in some manner. The rotating catch embodiment of FIGS. 13-1 and 13-2 may be suitable to prevent fluid ingress.

Figures 1, 14:
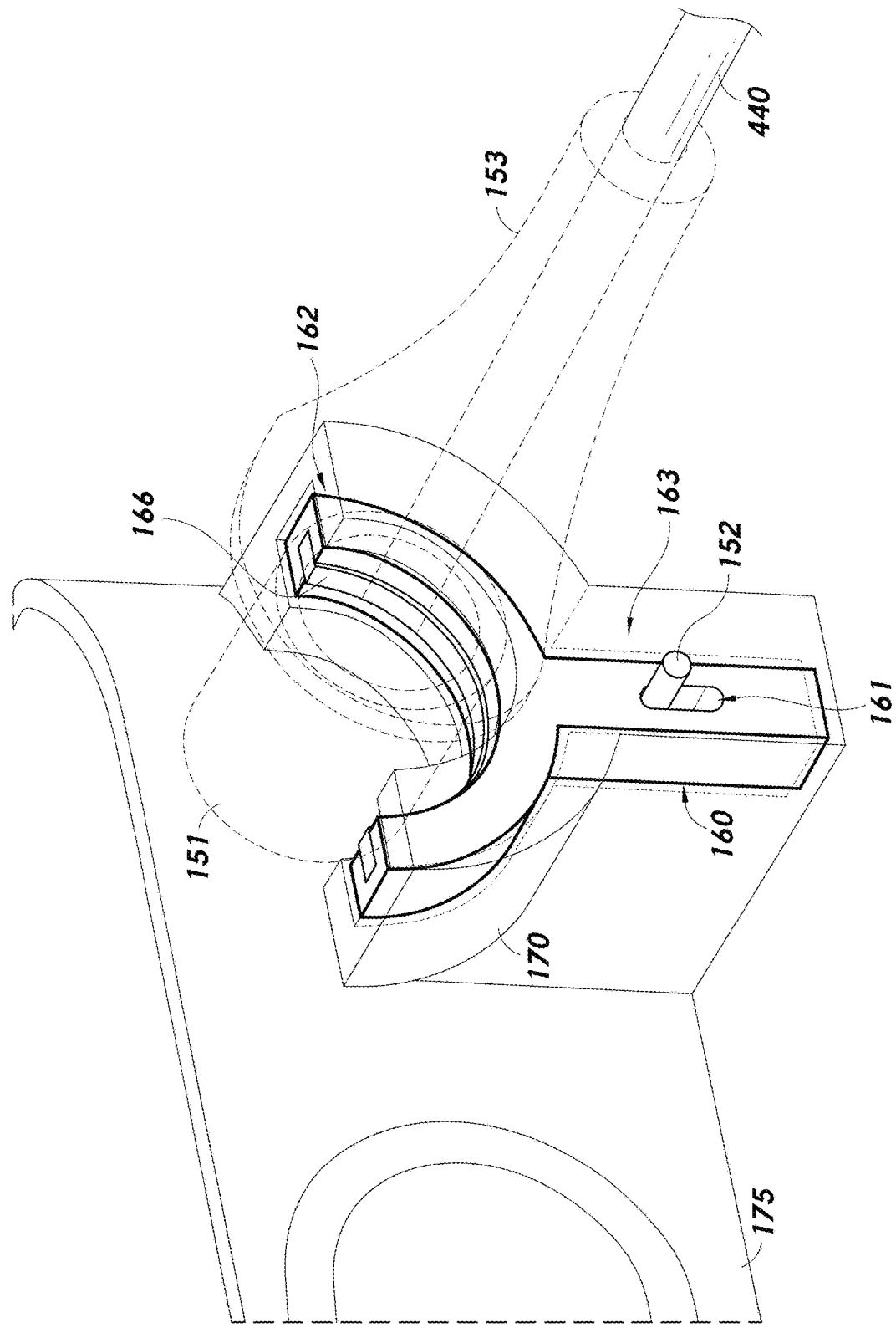
Figures 2, 14:
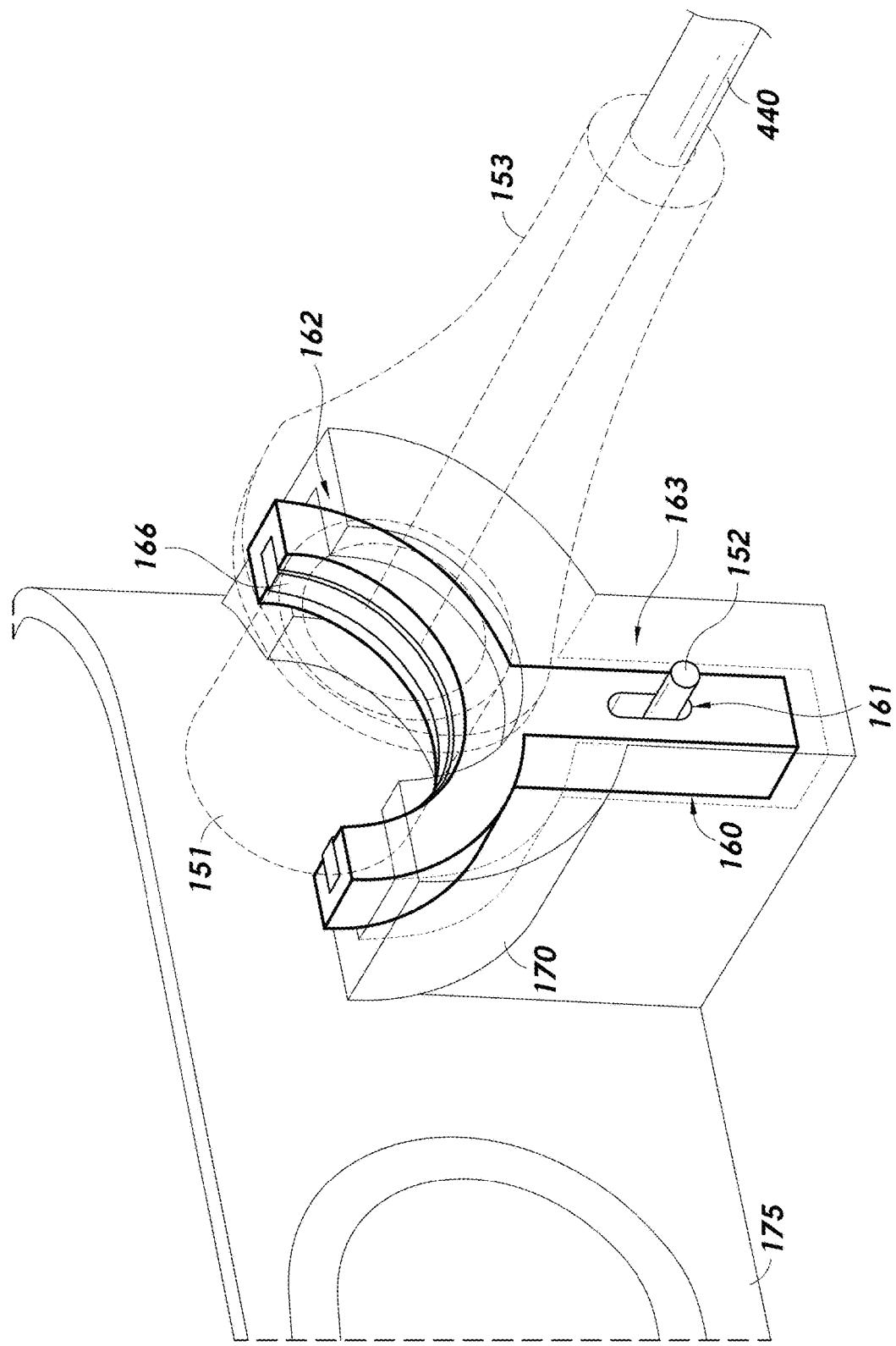

FIGS. 14-1 and 14-2 show a roll-lock feature 163 for an instrument having an instrument handle 175 and a shaft 40 component in accordance with one or more embodiments. The roll-lock feature 163 can comprise a forked shaft rotation stopper that may be disposed generally radially outside of the adapter and/or end effector component(s) to which the instrument handle 175 is attached in some embodiments. The stopper 163 may be configured to lock the shaft 440 by directly contacting the shaft 440 and/or base 151 or strain-relief form 153 associated therewith. The shaft roll stopper 163 can extend out distally from a distal portion of the handle 175 of the instrument.

The stopper 163 may include a strip 166 or area having high-friction-coefficient material configured to increase the roll resistance when the strip 166 and a component/portion of the shaft 440 are in contact. References herein to the shaft 440 can refer to the elongate tubular shaft portion 440 itself and/or to either or both of the shaft base 151 and the strain-relief form 153. In some embodiments, the stopper feature 163 includes a key feature (not shown) that is configured to key into a corresponding engagement feature associated with the shaft 440, strain-relief form 153, and/or base 151 thereof.

The base 151 of the shaft 440 can be coupled to and/or integrated with the shaft 440 in a manner such that the shaft 440 and base rotate together. In some embodiments, the base 151 comprises a rigid cylindrical base structure 151 of the shaft 440, which may be proximal to the strain-relief feature 153 (where present) in some embodiment, and may provide the engagement surface for the stopper feature 163. For example, the forked portion 162 of the stopper 163 can be configured to engage/contact the exterior surface of the base portion 151 to provide roll-stopping resistance/traction for the shaft 440.

The stopper 163 may include a base portion 160, which may be generally straight and/or elongate as shown in FIGS. 14-1 and 14-2, or may have any other suitable or desirable shape configured to permit vertical sliding or other movement (e.g., rotation) of the stopper 163 to bring the contact surface 166 thereof into contact with a portion of the shaft 440 (e.g., shaft base 151). In some embodiments, the base portion 160 includes a slot 161 or other feature configured to facilitate translation/sliding of the stopper 163. For example, a pin 152 or other form/component may be inserted/disposed at least partially within the slot 161 to retain the stopper 163 while allowing for translation of the stopper 163 corresponding to movement of the stopper such that the pin 152 slides within the slot 161 between locked and unlocked positions. For example, for the unlocked position (FIG. 14-1), the pin 152 may be at or near the top of the slot 161, whereas for the locked position (FIG. 14-2), the pin 152 may be at or near the bottom of the slot 161. FIG. 14-1 shows the stopper 163 in the unlocked position, in which the stopper sits within a housing 170 such that the contact area/strip 166 is not in contact with the shaft 440 or component(s) associated therewith (e.g., shaft base 151).

FIG. 14-2 shows the stopper 163 in the locked position in which the stopper 163 has been vertically translated/actuated to exert force at the contact area 166 against a component of the shaft 440, such as the shaft base 151, strain-relief component 153, and/or shaft body 440. Actuation of the stopper 163 between the locked and unlocked positions may be achieved using any suitable or desirable actuator means or mechanism. In some embodiments, the stopper 163 is biased such as through the use of one or more springs or other biasing devices, in either the locked or unlocked position. In some embodiments, the stopper 163 is configured to be robotically actuated in some manner. Although the forked portion 162 of the stopper 163 is illustrated as having a semicircular shape/form, it should be understood that such components/portions may have any suitable or desirable shape and/or contact surface/area.

Shaft Roll Processes

FIGS. 15-1, 15-2, and 15-3 provide a flow diagram for a process 1500 for rolling an instrument shaft 154 in accordance with one or more embodiments. FIGS. 16-1, 16-2, and 16-3 show certain images corresponding to various blocks, states, and/or operations associated with the process 1500 of FIGS. 15-1, 15-2, and 15-3, respectively, in accordance with one or more embodiments. The process 1500 may be performed at least in part by certain robotic system control circuitry, as described herein.

The process 1500 may be implemented in connection with a medical procedure, such as a kidney stone removal procedure, or other procedure that may be implemented using a shaft-type medical instrument 159, such as an endoscope, ureteroscope, or the like. That is, the process 1500 may be implemented at least in part following placement of a distal end of a shaft 154 of the shaft-type medical instrument 159 (e.g., endoscope) within certain target anatomy of a patient, such as a calyx network of a kidney of the patient. One or more operations of the process 1500 may be implemented prior to access of the target anatomy by the distal end of the shaft of the medical instrument.

At block 1502, the process 1500 involves manually rotating a shaft 154 of a medical instrument 159 relative to a handle 151 thereof to bring the shaft 154 into a home position, wherein a shaft roll locking mechanism of the handle 151 may be configured to engage/lock when the shaft is rotated manually to the home position, as shown in image 1602. For example, the handle 151 may have associated therewith one or more markings or features indicating an alignment of the shaft 154 relative to the handle 151. For example, a strain relief form 153, such as a cone-type form as described in detail herein, may have one or more features, such as a circumferential apex or other feature, indicating the orientation of the shaft 154. For example, the marker/indicator may be aligned with a working channel of the shaft 154, or other feature(s). In some implementations, the operation(s) associated with block 1502 of the process 1500 involve manually holding or grabbing the strain-relief feature 153 associated with a proximal end portion of the shaft 154 and rotating such form/feature 153 into an indicated home position, which may thereby cause a roll lock catch or other feature to engage a roll axle of the handle 151, thereby locking relative roll between the shaft 154 and the handle 151 of the medical instrument 159.

At block 1504, the process 1500 involves manually rolling/rotating the shaft 154 of the medical instrument 159 by manually rotating the handle 151 with the shaft 154 in a relative locked roll configuration implemented by shaft roll lock biasing (e.g., spring-loading on an axle lock/catch biasing the axle lock/catch in a locked configuration), as described herein. For example, the shaft 154 may be associated with the handle 151, which may be coupled to a proximal portion of the shaft 154. Due to the automatic roll locking, the medical instrument 159 may be configured such that rotation of the handle 151 translates to rotation of the shaft 154. That is, the shaft 154 may not be free to rotate relative to the handle 151, but rather may have a locked rotation relative to the handle 151. For example, the handle 151 may have associated therewith a roll-locking catch feature, as described in detail herein, wherein such feature may be biased in the locked position to prevent relative rotation between the shaft 154 and the handle 151 when the instrument 159 is manually manipulated/operated. Manually rolling the handle 151 of the medical instrument 159 in connection with block 1504 may be performed to bring a deflection plane of the shaft 154 and/or a distal end portion thereof into alignment with a plane of the particular anatomy in which the shaft is disposed. For example, manual handling and rotating of the handle 159 of the medical instrument may be performed to bring the shaft 154 into alignment with a kidney of the patient with respect to a renal operation.

At block 1506, the process 1500 involves docking the handle 151 of the medical instrument 159 on a robotic end effector/system 158. For example, the handle 151 may be docked on an adapter, such as a sterile adapter as described in detail herein, which may in turn be physically coupled to the end effector of a robot arm of a robotic system (e.g., cart system). Docking the handle 151 can involve rotating the handle lengthwise by about 90° to align the handle 31 with the engagement surface of the robotic instrument manipulator assembly 158 (e.g., adapter and/or end effector).

At block 1508, the process 1500 involves unlocking a roll axle of (e.g., within) the handle 151 of the medical instrument 159. For example, such unlocking may happen substantially automatically when the handle 151 is latched on the end effector/adapter 158. For example, one or more features of the end effector/adapter 158 may be configured to actuate an axle catch component of the handle 151 when the handle 151 is placed on and/or pressed against the end effector/adapter 158.

At block of 1510, the process 1500 involves robotically rolling the shaft 154 relative to the handle 151 of the medical instrument 159. For example, one or more drive outputs of the robotic system 158 may be implemented to cause shaft roll through engagement with drive input(s) of the instrument handle 151. At block 1512, the process 1500 may involve returning the shaft 154 to the home position with respect to roll orientation thereof relative to the handle. Such action may be performed robotically or manually, and may occur before or after undocking of the handle/instrument 151 from the robotic system 158.

At block 1514, the process 1500 involves unlatching/undocking the handle 151 from the end effector/adapter 158, thereby locking the rotation of the shaft 154 relative to the handle 151. In the event that the shaft 154 has not been brought into the home position yet, it may be necessary to manually rotate the shaft 154 relative to the handle 151 to bring the shaft 154 into the home roll position, thereby enabling locking of the shaft 154 roll through biasing of the axle catch of the handle 151.

Described herein are systems, devices, and methods to facilitate the robotic rolling of shafts of medical instruments, as well as the limiting and/or restriction of such rolling, in connection with certain medical procedures. In particular, systems, devices, and methods in accordance with one or more aspects of the present disclosure can facilitate the locking of robotic shaft roll, which may be implemented automatically in connection with undocking of the instrument from a robotic end effector or other system component. Robotic shaft roll, shaft roll locking, and shaft roll restriction/limitation in accordance with the various embodiments disclosed herein can advantageously reduce certain risks and/or inefficiencies associated with rolling of an instrument.

In some implementations, the present disclosure relates to a medical instrument comprising an elongate shaft defining a roll axis and a handle coupled to the elongate shaft. The handle comprises a robotic drive input operable to rotate the elongate shaft with respect to the handle about the roll axis and a lockout mechanism movable between an engaged position in which the lockout mechanism impedes rotation of the elongate shaft with respect to the handle about the roll axis, and a disengaged position in which the lockout mechanism permits rotation of the elongate shaft with respect to the handle about the roll axis.

The lockout mechanism can be configured to move to the engaged position in a configuration where the handle is off-robot. In some embodiments, the lockout mechanism is configured to move to the engaged position in a configuration where the handle is off-robot and the elongate shaft is at a predefined angular position about the roll axis.

The medical instrument can further comprise an axle having a first axis, a shaft gear associated with a proximal end of the elongate shaft, the shaft gear having a second axis that is transverse with respect to the first axis, and a bevel gear having a third axis that is parallel with the first axis, the bevel gear being in a mesh configuration with the shaft gear. The bevel gear can be coupled to the axle by a belt configured to translate rotational movement of the axle to the bevel gear.

The medical instrument can further comprise an axle having a first axis, a shaft gear associated with a proximal end of the elongate shaft, the shaft gear having a second axis that is transverse with respect to the first axis, a bevel gear disposed in the handle in a mesh configuration with the axle, the bevel gear being configured to rotate about a third axis that is parallel to the second axis, and a rod coupled to, and coaxial with, the bevel gear. The rod can be configured to cause rotation of the shaft gear.

The medical instrument can further comprise an axle actuatable by the robotic drive input, and an axle-retention structure disposed at least partially over the axle, the axle-retention structure being configured to limit rotation of the axle. In some embodiments, the axle-retention structure includes a first open annular channel and one or more first stopper surfaces exposed within the first open annular channel and configured to limit rotation of the axle. For example, the axle can include a second open annular channel that is open to the first open annular channel at least in part and one or more second stopper surfaces exposed within the second open annular channel and configured to limit rotation of the axle. The medical instrument can further comprise a slider form comprising a first portion configured to be disposed at least partially within the first open annular channel and contact the one or more first stopper surfaces and a second portion configured to be disposed at least partially within the second open annular channel and contact the one or more second stopper surfaces.

In some implementations, the present disclosure relates to a robotic medical system comprising a robotic manipulator comprising a plurality of drive outputs and a boss. The robotic medical system further comprises a medical instrument comprising a handle mountable to the adapter and an elongate shaft insertable into a patient, the handle comprising a plurality of drive inputs and a lockout mechanism configured to selectively permit or impede rotation of the elongate shaft with respect to the handle. The boss is configured to disengage the lockout mechanism upon mounting the handle to the adapter.

In some embodiments, the robotic manipulator assembly comprises a robotic end effector including a plurality of drive outputs and an adapter mountable on the robotic end effector and comprising a plurality of drive couplers and the boss. The boss can be configured to vertically translate at least a portion of the lockout mechanism. In some embodiments, the boss is configured to rotate at least a portion of the lockout mechanism.

In some implementations, the present disclosure relates to a medical instrument comprising an elongate shaft, a handle coupled to a proximal portion of the elongate shaft, an axle associated with the handle, the axle being configured such that rotation of the axle causes the elongate shaft to rotate about an axis of the elongate shaft, and an axle catch disposed at least partially within the handle and configured to be actuated to impede rotation of the axle.

In some embodiments, the axle catch comprises a key configured to engage with a mating feature of the axle. For example, when the key is disposed at least partially within the mating feature of the axle, rotation of the axle can be restricted. The key of the axle catch can be configured to enter the mating feature of the axle in an axial direction with respect to an axis of the axle. In some embodiments, the axle catch is configured to be actuated in a direction parallel to an axis of the axle. For example, the axle catch can include one or more alignment pin channels that have axes that are parallel with the axis of the axle and are configured to have respective alignment pins disposed at least partially therein, the respective alignment pins guiding actuation of the axle catch in the direction parallel to the axis of the axle. The key of the axle catch can be configured to enter the mating feature of the axle through a side portion of the axle. For example, the axle catch can be configured to rotate about an axis that is parallel with an axis of the axle. In some embodiments, the key comprises a bent projection.

The axle catch can comprise a catch actuator. For example, the catch actuator may be a unitary form with the axle catch. In some embodiments, the catch actuator is associated with a first longitudinal end of the axle catch and the catch actuator is associated with a second longitudinal end of the axle catch. In some embodiments, the catch actuator is accessible from outside of the handle. For example, the catch actuator can comprise a plug configured to be disposed at least partially in an aperture form of the handle. Alternatively, the catch actuator can comprise a cam structure configure to rotate about an axis of the cam structure.

In some implementations, the present disclosure relates to the axle catch is biased in a locked configuration in which rotation of the axle is impeded. The medical instrument can further comprise a spring disposed at least partially within a cup form of the axle catch and configured to exert force on the axle catch biasing the axle catch in the locked configuration. In some embodiments, the medical instrument further comprises an axle retainer structure disposed within the handle, wherein the axle retainer structure axially secures the axle in place and the spring is configured to push against an underside of the axle retainer structure when disposed at least partially within the cup form.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A medical instrument comprising:
   an elongate shaft defining a roll axis; and
   a handle coupled to the elongate shaft, the handle comprising:
      a robotic drive input operable to rotate the elongate shaft with respect to the handle about the roll axis;
      an axle actuatable by the robotic drive input; and
      an axle-retention structure disposed at least partially over the axle and configured to limit rotation of the axle, the axle-retention structure comprising:
         a first open annular channel; and
         one or more first stopper surfaces exposed within the first open annular channel and configured to limit rotation of the axle.

2. The medical instrument of claim 1, wherein:
   the axle includes a second open annular channel that faces the first open annular channel of the axle-retention structure, the second open annular channel comprising two second stopper surfaces;
   the axle includes a radial lock mating channel disposed between the two second stopper surfaces; and
   the medical instrument further comprises a lock mechanism configured to mate with the radial lock mating channel of the axle.

3. The medical instrument of claim 2, wherein the lock mechanism is configured to automatically move from a disengaged position to an engaged position with the radial lock mating channel when the elongate shaft is manually rotated to a predefined angular position about the roll axis.

4. The medical instrument of claim 1, further comprising:
   a shaft gear coupled with a proximal end of the elongate shaft, the shaft gear having a first axis that is transverse with respect to a second axis of the axle; and
   a bevel gear having a third axis that is parallel with the second first axis, the bevel gear being in a mesh configuration with the shaft gear;
   wherein the bevel gear is coupled to the axle by a belt configured to translate rotational movement of the axle to the bevel gear.

5. The medical instrument of claim 1, further comprising:
   a shaft gear coupled with a proximal end of the elongate shaft, the shaft gear having a first axis that is transverse with respect to a second axis of the axle;
   a bevel gear disposed in the handle in a mesh configuration with the axle, the bevel gear being configured to rotate about a third axis that is parallel to the first axis; and
   a rod coupled to, and coaxial with, the bevel gear;
   wherein the rod is configured to cause rotation of the shaft gear.

6. The medical instrument of claim 1, wherein the axle-retention structure is fixed to the handle, whereas the axle is rotatable relative to the handle.

7. The medical instrument of claim 1, wherein the axle includes:
   a second open annular channel that is open to the first open annular channel at least in part; and
   one or more second stopper surfaces exposed within the second open annular channel and configured to limit rotation of the axle.

8. The medical instrument of claim 7, further comprising a slider form comprising:
   a first portion configured to be slidingly disposed at least partially within the first open annular channel and contact the one or more first stopper surfaces; and
   a second portion configured to be slidingly disposed at least partially within the second open annular channel and contact the one or more second stopper surfaces.

9. A robotic system comprising:
   a robotic manipulator assembly comprising one or more drive outputs and a boss; and
   an instrument comprising a handle mountable to the robotic manipulator assembly and an elongate shaft insertable into a patient, the handle comprising:
      a plurality of drive inputs;
      an axle actuatable by one of the plurality of drive inputs; and
      an axle-retention structure disposed at least partially over the axle and configured to limit rotation of the axle, the axle-retention structure comprising:
         a first open annular channel; and
         one or more first stopper surfaces exposed within the first open annular channel and configured to limit rotation of the axle.

10. The robotic system of claim 9, wherein the robotic manipulator assembly comprises:
    a robotic end effector including a plurality of drive outputs; and
    an adapter mountable on the robotic end effector and comprising a plurality of drive couplers and the boss.

11. The robotic system of claim 9, wherein the boss is configured actuate a lock configured to mate with the axle and restrict rotation of the axle.

12. A medical instrument comprising:
    an elongate shaft;
    a handle coupled to a proximal portion of the elongate shaft;
    an axle coupled with the handle, the axle being configured such that rotation of the axle causes the elongate shaft to rotate about an axis of the elongate shaft; and
    an axle-retention structure disposed at least partially over the axle and configured to limit rotation of the axle, the axle-retention structure comprising:
       a first open annular channel; and
       one or more first stopper surfaces exposed within the first open annular channel and configured to limit rotation of the axle.

13. A medical instrument of claim 12, further comprising and axle catch disposed at least partially within the handle and configured to move between an unlocked position in which the axle catch permits rotation of the axle and a locked position in which the axle catch restricts rotation of the axle, wherein
    the axle catch comprises a key configured to engage with a mating feature of the axle; and
    when the key is disposed at least partially within the mating feature of the axle, rotation of the axle is restricted.

14. The medical instrument of claim 13, wherein the key of the axle catch is configured to enter the mating feature of the axle in an axial direction with respect to an axis of the axle.

15. The medical instrument of claim 13, wherein the axle catch is configured to be actuated in a direction parallel to an axis of the axle.

16. The medical instrument of claim 15, wherein the axle catch includes one or more alignment pin channels that have axes that are parallel with the axis of the axle and are configured to have respective alignment pins disposed at least partially therein, the respective alignment pins guiding linear translation the axle catch in the direction parallel to the axis of the axle.

17. The medical instrument of claim 13, wherein the key of the axle catch is configured to enter the mating feature of the axle through a side portion of the axle.

18. The medical instrument of claim 17, wherein the axle catch is configured to rotate about an axis that is parallel with an axis of the axle.

19. The medical instrument of claim 12, wherein;
the axle includes a second open annular channel that is open towards the first open annular channel of the axle-retention structure; and
the medical instrument includes an arcuate slider including a first portion configured to slide within the first open annular channel and a second portion configured to slide within the second open annular channel.

\* \* \* \* \*